US011306087B2

(12) United States Patent
Lanman et al.

(10) Patent No.: US 11,306,087 B2
(45) Date of Patent: *Apr. 19, 2022

(54) INHIBITORS OF KRAS G12C AND METHODS OF USING THE SAME

(71) Applicant: Amgen Inc., Thousand Oaks, CA (US)

(72) Inventors: Brian Alan Lanman, Thousand Oaks, CA (US); Shon Booker, Thousand Oaks, CA (US); Clifford Goodman, Thousand Oaks, CA (US); Anthony B. Reed, Thousand Oaks, CA (US); Jonathan D. Low, Thousand Oaks, CA (US); Hui-Ling Wang, Thousand Oaks, CA (US); Ning Chen, Thousand Oaks, CA (US); Ana Elena Minatti, Thousand Oaks, CA (US); Ryan Wurz, Thousand Oaks, CA (US); Victor J. Cee, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/817,109

(22) Filed: Mar. 12, 2020

(65) Prior Publication Data

US 2020/0207766 A1 Jul. 2, 2020

Related U.S. Application Data

(63) Continuation of application No. 16/125,359, filed on Sep. 7, 2018, now Pat. No. 10,640,504.

(60) Provisional application No. 62/556,223, filed on Sep. 8, 2017.

(51) Int. Cl.
C07D 471/04 (2006.01)
A61P 35/00 (2006.01)
A61K 31/519 (2006.01)
A61K 31/7068 (2006.01)
A61K 38/07 (2006.01)

(52) U.S. Cl.
CPC .......... C07D 471/04 (2013.01); A61K 31/519 (2013.01); A61P 35/00 (2018.01); A61K 31/7068 (2013.01); A61K 38/07 (2013.01); A61K 2300/00 (2013.01)

(58) Field of Classification Search
CPC .................................................. C07D 471/04
See application file for complete search history.

(56) References Cited

U.S. PATENT DOCUMENTS

| 4,232,027 | A | 11/1980 | Turk et al. |
|---|---|---|---|
| 5,100,883 | A | 3/1992 | Schiehser |
| 5,118,677 | A | 6/1992 | Caufield |
| 5,118,678 | A | 6/1992 | Kao et al. |
| 5,120,842 | A | 6/1992 | Failli et al. |
| 5,151,413 | A | 9/1992 | Caufield et al. |
| 5,256,790 | A | 10/1993 | Nelson |
| 5,258,389 | A | 11/1993 | Goulet et al. |
| 5,521,184 | A | 5/1996 | Zimmermann |
| 5,650,415 | A | 7/1997 | Tang et al. |
| 5,656,643 | A | 8/1997 | Spada et al. |
| 5,712,291 | A | 1/1998 | D'Amato |
| 5,728,813 | A | 3/1998 | Lyman et al. |
| 5,747,498 | A | 5/1998 | Schnur et al. |
| 5,770,599 | A | 6/1998 | Gibson |
| 5,789,427 | A | 8/1998 | Chen et al. |
| 5,792,783 | A | 8/1998 | Tang et al. |
| 5,861,510 | A | 1/1999 | Piscopio et al. |
| 5,863,949 | A | 1/1999 | Robinson et al. |
| 5,892,112 | A | 4/1999 | Levy et al. |
| 5,969,110 | A | 10/1999 | Beckmann et al. |
| 5,981,245 | A | 11/1999 | Fox et al. |
| 5,990,141 | A | 11/1999 | Hirth et al. |
| 6,057,124 | A | 5/2000 | Bartley et al. |
| 6,111,090 | A | 8/2000 | Gorman et al. |
| 6,232,447 | B1 | 5/2001 | Cerretti |
| 6,235,764 | B1 | 5/2001 | Larson et al. |
| 6,258,812 | B1 | 7/2001 | Bold et al. |
| 6,413,932 | B1 | 7/2002 | Cerretti et al. |
| 6,515,004 | B1 | 2/2003 | Misra et al. |
| 6,596,852 | B2 | 7/2003 | Cerretti et al. |
| 6,630,500 | B2 | 10/2003 | Gingrich et al. |
| 6,656,963 | B2 | 12/2003 | Firestone et al. |
| 6,713,485 | B2 | 3/2004 | Carter et al. |
| 6,727,225 | B2 | 4/2004 | Wiley |
| 7,025,962 | B1 | 4/2006 | Gorman et al. |
| 7,361,760 | B2 | 4/2008 | Sircar et al. |
| 7,618,632 | B2 | 11/2009 | Collins et al. |
| 7,812,135 | B2 | 10/2010 | Smith et al. |

(Continued)

FOREIGN PATENT DOCUMENTS

| DE | 19629652 A1 | 1/1998 |
|---|---|---|
| EP | 0090505 A2 | 10/1983 |

(Continued)

OTHER PUBLICATIONS

"KRASG12C Inhibitor," Mirati Therapeutics, retrieved on Nov. 27, 2018, from https://www.mirati.com/mrtx849/, 5 pages.
Ahmadian, et al., "Guanosine triphosphatase stimulation of oncogenic Ras mutants," PNAS, 96: 7065-7070, 1999.
Airoldi, et al., "Glucose-Derived Ras Pathway Inhibitors: Evidence of Ras—Ligand Binding and Ras—GEF (Cdc25) Interaction Inhibition," ChemBioChem, 8: 1376-1379 (2007).
Attc "Organism: Mus musculus (B cell); Mus musculus (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.
Barnett, et al., "Identification and characterization of pleckstrin-holomogy-domain-dependent and isoenzyme specific Akt inhibitors," Biochem. J.,385 (2): 399-408 (2005).

(Continued)

Primary Examiner — John S Kenyon
(74) Attorney, Agent, or Firm — Markus Bergauer

(57) ABSTRACT

Provided herein are methods of using KRAS G12C inhibitors. These methods of using the inhibitors are useful for treating a number of disorders, including pancreatic, colorectal, and lung cancers.

55 Claims, No Drawings
Specification includes a Sequence Listing.

(56) References Cited

U.S. PATENT DOCUMENTS

| | | | |
|---|---|---|---|
| 8,388,967 | B2 | 3/2013 | Smith et al. |
| 8,586,023 | B2 | 11/2013 | Shiku et al. |
| 8,591,886 | B2 | 11/2013 | Ponath et al. |
| 10,519,146 | B2 | 12/2019 | Lanman et al. |
| 10,532,042 | B2 | 1/2020 | Lanman et al. |
| 10,640,504 | B2* | 5/2020 | Lanman .............. C07D 471/04 |
| 10,988,485 | B2 | 4/2021 | Minatti et al. |
| 11,045,484 | B2 | 6/2021 | Wurz et al. |
| 11,053,226 | B2 | 7/2021 | Shin et al. |
| 11,090,304 | B2 | 8/2021 | Allen et al. |
| 11,096,939 | B2 | 8/2021 | Booker et al. |
| 2002/0042368 | A1 | 4/2002 | Fanslow, III et al. |
| 2003/0105091 | A1 | 6/2003 | Riedl et al. |
| 2003/0162712 | A1 | 8/2003 | Cerretti et al. |
| 2009/0012085 | A1 | 1/2009 | Baum et al. |
| 2014/0288045 | A1 | 9/2014 | Ren et al. |
| 2015/0239900 | A1 | 8/2015 | Li et al. |
| 2016/0159738 | A1 | 6/2016 | Ren et al. |
| 2016/0166571 | A1 | 6/2016 | Janes et al. |
| 2016/0297774 | A1 | 10/2016 | Li et al. |
| 2018/0015087 | A1 | 1/2018 | Liu et al. |
| 2018/0072723 | A1 | 3/2018 | Blake et al. |
| 2018/0177767 | A1 | 6/2018 | Lanman et al. |
| 2018/0334454 | A1 | 11/2018 | Lanman et al. |
| 2019/0077801 | A1 | 3/2019 | Lanman et al. |
| 2019/0336514 | A1 | 11/2019 | Wurz et al. |
| 2019/0343838 | A1* | 11/2019 | Allen .................... C07D 487/04 |
| 2019/0345169 | A1 | 11/2019 | Minatti et al. |
| 2019/0374542 | A1* | 12/2019 | Allen .............. A61K 39/39558 |
| 2019/0375749 | A1 | 12/2019 | Chen et al. |
| 2020/0030324 | A1 | 1/2020 | Booker et al. |
| 2020/0055845 | A1 | 2/2020 | Lanman et al. |
| 2020/0069657 | A1 | 3/2020 | Lanman et al. |
| 2020/0165231 | A1 | 5/2020 | Shin et al. |
| 2020/0216446 | A1 | 7/2020 | Parsons et al. |
| 2020/0222407 | A1 | 7/2020 | Lipford et al. |
| 2020/0360374 | A1 | 11/2020 | Henary et al. |
| 2020/0369662 | A1* | 11/2020 | Chaves ................ C07D 471/04 |
| 2021/0009577 | A1 | 1/2021 | Lanman et al. |

FOREIGN PATENT DOCUMENTS

| | | |
|---|---|---|
| EP | 0520722 A1 | 12/1992 |
| EP | 0566226 A1 | 10/1993 |
| EP | 0606046 A1 | 7/1994 |
| EP | 0682027 A1 | 11/1995 |
| EP | 0407122 A1 | 10/1996 |
| EP | 0770622 A2 | 5/1997 |
| EP | 0780386 A1 | 6/1997 |
| EP | 0787772 A2 | 8/1997 |
| EP | 0818442 A2 | 1/1998 |
| EP | 0837063 A1 | 4/1998 |
| EP | 0931788 A2 | 7/1999 |
| EP | 0970070 B1 | 1/2000 |
| EP | 1004578 A2 | 5/2000 |
| EP | 1181017 B1 | 2/2002 |
| EP | 1786785 B9 | 5/2007 |
| EP | 1866339 B1 | 12/2007 |
| EP | 1947183 A1 | 7/2008 |
| EP | 3401314 A1 | 11/2019 |
| EP | 3055290 B1 | 12/2019 |
| JP | 02233610 A | 9/1990 |
| JP | 2019031476 A | 2/2019 |
| WO | 1990005719 A1 | 5/1990 |
| WO | 1992005179 A1 | 4/1992 |
| WO | 1992020642 A1 | 11/1992 |
| WO | 1993011130 A1 | 6/1993 |
| WO | 1994002136 A1 | 2/1994 |
| WO | 1994002485 A1 | 2/1994 |
| WO | 1994009010 A1 | 4/1994 |
| WO | 1995009847 A1 | 4/1995 |
| WO | 1995014023 A1 | 5/1995 |
| WO | 1995016691 A1 | 6/1995 |
| WO | 1995019774 A1 | 7/1995 |
| WO | 1995019970 A1 | 7/1995 |
| WO | 1996027583 A1 | 9/1996 |
| WO | 1996030347 A1 | 10/1996 |
| WO | 1996031510 A1 | 10/1996 |
| WO | 1996033172 A1 | 10/1996 |
| WO | 1996033980 A1 | 10/1996 |
| WO | 1996041807 A1 | 12/1996 |
| WO | 1997002266 A1 | 1/1997 |
| WO | 1997013771 A1 | 4/1997 |
| WO | 1997019065 A1 | 5/1997 |
| WO | 1997027199 A1 | 7/1997 |
| WO | 1997030034 A1 | 8/1997 |
| WO | 1997030044 A1 | 8/1997 |
| WO | 1997032880 A1 | 9/1997 |
| WO | 1997032881 A1 | 9/1997 |
| WO | 1997034895 A1 | 9/1997 |
| WO | 1997038983 A1 | 10/1997 |
| WO | 1997038994 A1 | 10/1997 |
| WO | 1997049688 A1 | 12/1997 |
| WO | 1998002434 A1 | 1/1998 |
| WO | 1998002437 A1 | 1/1998 |
| WO | 1998002438 A1 | 1/1998 |
| WO | 1998002441 A2 | 1/1998 |
| WO | 1998003516 A1 | 1/1998 |
| WO | 1998007697 A1 | 2/1998 |
| WO | 1998007726 A1 | 2/1998 |
| WO | 1998014449 A1 | 4/1998 |
| WO | 1998014450 A1 | 4/1998 |
| WO | 1998014451 A1 | 4/1998 |
| WO | 1998017662 A1 | 4/1998 |
| WO | 1998030566 A1 | 7/1998 |
| WO | 1998033768 A1 | 8/1998 |
| WO | 1998033798 A2 | 8/1998 |
| WO | 1998034915 A1 | 8/1998 |
| WO | 1998034918 A1 | 8/1998 |
| WO | 1999007675 A1 | 2/1999 |
| WO | 1999007701 A1 | 2/1999 |
| WO | 1999020758 A1 | 4/1999 |
| WO | 1999029667 A1 | 6/1999 |
| WO | 1999035132 A1 | 7/1999 |
| WO | 1999035146 A1 | 7/1999 |
| WO | 1999040196 A1 | 8/1999 |
| WO | 1999045009 A1 | 9/1999 |
| WO | 1999052889 A1 | 10/1999 |
| WO | 1999052910 A1 | 10/1999 |
| WO | 1999061422 A1 | 12/1999 |
| WO | 2000002871 A1 | 1/2000 |
| WO | 2000012089 A1 | 3/2000 |
| WO | 2000059509 A1 | 10/2000 |
| WO | 2001003720 A2 | 1/2001 |
| WO | 2001014387 A1 | 3/2001 |
| WO | 2001032651 A1 | 5/2001 |
| WO | 2001037820 A2 | 5/2001 |
| WO | 2002055501 A2 | 7/2002 |
| WO | 2002059110 A1 | 8/2002 |
| WO | 2002066470 A1 | 8/2002 |
| WO | 2002068406 A2 | 9/2002 |
| WO | 2004005279 A2 | 1/2004 |
| WO | 2004007458 A1 | 1/2004 |
| WO | 2004007481 A2 | 1/2004 |
| WO | 2004009784 A2 | 1/2004 |
| WO | 2005005434 A1 | 1/2005 |
| WO | 2005007190 A1 | 1/2005 |
| WO | 2005011700 A1 | 2/2005 |
| WO | 2005016252 A2 | 2/2005 |
| WO | 2005021546 A1 | 3/2005 |
| WO | 2005055808 A2 | 6/2005 |
| WO | 2005115451 A1 | 12/2005 |
| WO | 2006044453 A1 | 4/2006 |
| WO | 2006083289 A2 | 8/2006 |
| WO | 2006121168 A1 | 11/2006 |
| WO | 2006122806 A2 | 11/2006 |
| WO | 2007133822 A1 | 11/2007 |
| WO | 2008070740 A1 | 6/2008 |
| WO | 2009036082 A2 | 3/2009 |
| WO | 2009055730 A1 | 4/2009 |
| WO | 2010003118 A1 | 1/2010 |
| WO | 2011028683 A1 | 3/2011 |
| WO | 2011051726 A2 | 5/2011 |
| WO | 2011090754 A1 | 6/2011 |

(56) References Cited

FOREIGN PATENT DOCUMENTS

| | | | |
|---|---|---|---|
| WO | 2012142498 A2 | 10/2012 | |
| WO | 2013039954 A1 | 3/2013 | |
| WO | 2013155223 A1 | 10/2013 | |
| WO | 2014143659 A1 | 9/2014 | |
| WO | 2014152588 A1 | 9/2014 | |
| WO | 2015001076 A1 | 1/2015 | |
| WO | 2015054572 A1 | 4/2015 | |
| WO | 2015075483 A1 | 5/2015 | |
| WO | 2016044772 A1 | 3/2016 | |
| WO | 2016049524 A1 | 3/2016 | |
| WO | 2016049565 A1 | 3/2016 | |
| WO | 2016049568 A1 | 3/2016 | |
| WO | 2016164675 A1 | 10/2016 | |
| WO | 2016168540 A1 | 10/2016 | |
| WO | 2017015562 A1 | 1/2017 | |
| WO | 2017058728 A1 | 4/2017 | |
| WO | 2017058768 A1 | 4/2017 | |
| WO | 2017058792 A1 | 4/2017 | |
| WO | 2017058805 A1 | 4/2017 | |
| WO | 2017058807 A1 | 4/2017 | |
| WO | 2017058902 A1 | 4/2017 | |
| WO | 2017058915 A1 | 4/2017 | |
| WO | 2017087528 A1 | 5/2017 | |
| WO | 2017100546 A1 | 6/2017 | |
| WO | 2017172979 A1 | 10/2017 | |
| WO | 2017201161 A1 | 11/2017 | |
| WO | 2018064510 A1 | 4/2018 | |
| WO | 2018068017 A1 | 4/2018 | |
| WO | 2018119183 A3 | 6/2018 | |
| WO | WO-2018119183 A2 * | 6/2018 | ........... A61K 31/502 |
| WO | 2018140598 A1 | 8/2018 | |
| WO | 2018217651 A1 | 11/2018 | |
| WO | 2018218069 A1 | 11/2018 | |
| WO | 2019051291 A1 | 3/2019 | |
| WO | 2019213516 A1 | 11/2019 | |
| WO | 2019213526 A1 | 11/2019 | |
| WO | 2019217691 A1 | 11/2019 | |
| WO | 2019232419 A1 | 12/2019 | |
| WO | 2019241157 A1 | 12/2019 | |
| WO | 2019243533 A1 | 12/2019 | |
| WO | 2019243535 A1 | 12/2019 | |
| WO | 2020050890 A2 | 3/2020 | |
| WO | 2020102730 A1 | 5/2020 | |
| WO | 2020106640 A1 | 5/2020 | |
| WO | 2020156285 A1 | 8/2020 | |
| WO | 2020232130 A1 | 11/2020 | |
| WO | 2020236947 A1 | 11/2020 | |
| WO | 2020236948 A1 | 11/2020 | |
| WO | 2021081212 A1 | 4/2021 | |
| WO | 2021126816 A1 | 6/2021 | |

OTHER PUBLICATIONS

Bull, et al., "Isoquino[2,1-c][1,3,2] Benzodiazaphosphorine Derivatives: New Potential Agents for Cancer Chemotherapy," *Phosphorus, Sulfur, and Silicon*, 162:231-243 (2000).
Campillo, et al., "Novel Bronchodilators: Synthesis, Transamination Reactions, and Pharmacology of a Series of Pyrazino[2,3-c][1,2,6]thiadiazine 2,2-Dioxides," *J. Med. Chem.*, 43: 4219-4227 (2000).
Cecil Textbook of Medicine, edited by Bennett, J.C., and Plum, F., $20^{th}$ edition, vol. 1: 1004-1010 (1996).
Cowen Slide deck—Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).
Dasmahapatra, et al., "In vitro Combination Treatment with Perifosine and UCN-01 Demonstrates Synergism Against Prostate (PC-3) and Lung (A549) Epithelial Adenocarcinoma Cell Lines," *Clin. Cancer Res.* 10(15): 5242-5252 (2004).
Dermer, et al., "Another Anniversary for the War on Cancer," *Bio/Technology*, 12: 320 (1994).
Douelle, et al., "Highly Diastereoselective Synthesis of vicinal Quaternary and Tertiary Stereocenters Using the Iodo-aldol Cyclization," *Org. Lett.*, 9 (10): 1931-1934 (2007).
Erkkilä, et al., "Mild Organocatalytic α-Methylenation of Aldehydes," *J. Org. Chem.*,71 (6), 2538-2541 (2006).
Freshney, et al., Culture of Animal Cells, *A Manual of Basic Technique*, Alan R. Liss, Inc, New York, p4 (1983).
Gentile, et al., "Discovery and Structural Investigation of Novel Binders to the Ras Switch II Pocket," NCI Initiative Symposium Poster (2015).
Gills and Dennis, "The development of phosphatidylinositol ether lipid analogues as inhibitors of the serine/threonine kinase, Akt," *Expert. Opin. Investig. Drugs*, 13: 787-797 (2004).
Goldberg, et al., "Role of PD-1 and its ligand, B7-H1, in early fate decisions of CD8 T cells," *Blood*,110(1): 186-192 (2007).
Goldstein, et al., "Biological efficacy of a chimeric antibody to the epidermal growth factor receptor in a human tumor xenograft model," *Clin. Cancer Res.*, 1: 1311-1318 (1995).
Hansen, et al., "Abstract 686: Drugging an undruggable pocket: the biochemical mechanism of covalent $KRAS^{G12C}$ inhibitors," Proceedings of the American Association for Cancer Research Annual Meeting 2018; Apr. 14-18, 2018; Chicago, IL; AACR; *Cancer Res.*, 78(13 Suppl): Abstract 686 (2018).
Hichri, et al., "A Convenient Synthesis of 1,3,2-Benzodiazaphophorine-2-Oxide," *Phosphorus, Sulfur*, and *Silicon*, 190: 29-35 (2015).
Hocker, et al., "Andrographolide derivatives inhibit guanine nucleotide exchange and abrogate oncogenic Ras function," *PNAS*, 110(25): 10201-10206 (2013).
Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).
International Search Report for PCT/US2017/067801, dated Jul. 25, 2018, 6 pages.
International Search Report for PCT/US2018/033714, dated Jul. 17, 2018, 3 pages.
Janes, et al., "Targeting KRAS Mutant Cancers with a Covalent G12C-Specific Inhibitor," *Cell*, 172: 578-589 (2018).
Jin, et al., "Inhibition of AKT survival pathway by a small molecule inhibitor in human endometrial cancer cells," *Br. J. Cancer*, 91: 1808-1812 (2004).
Lim, et al., "Therapeutic Targeting of Oncogenic K-Ras by a Covalent Catalytic Site Inhibitor," *Angew. Chem. Int. Ed*, 53: 199-204 (2014).
Liu, Y., "Session SY28—Transformative Small Molecule Therapies—Targeting KRAS mutant cancers with a covalent G12C—specific inhibitor," Presentation on Apr. 4, 2017, AACR Annual Meeting Presentation, Apr. 1-5, 2017, Washington, D.C. (2017).
Lu, et al., "KRAS G12C Drug Development: Discrimination between Switch II Pocket Configurations Using Hydrogen/Deuterium-Exchange Mass Spectrometry," *Structure*, 25: 1-7 (2017).
Maurer, et al., "Small-molecule ligands bind to a distinct pocket in Rad and inhibit SOS-mediated nucleotide exchange activity," *PNAS*, 109(14): 5299-5304 (2012).
McGregor, et al., "Expanding the Scope of Electrophiles Capable of Targeting K-Ras Oncogenes," *ACS Bio. Chem.*, 56: 3179-3183 (2017).
Mirati Therapeutics, "Corporate Presentation Nov. 2017," Slides 1-41 (2017).
Modjtahedi, et al., "The human EGF receptor as a target for cancer therapy: six new rat mAbs AGainst the receptor on the breast carcinoma MDA-MB 468," *Br. J. Cancer*, 67(2): 247-253 (1993).
National Cancer Institute identifier: NSC 154020, retrieved on Nov. 29, 2018, from https://cactus.nci.nih.gov/ncidb2.2/.
NCBI Reference Sequence, "GTPase KRas isoform a [*Homo sapiens*]," GenBank Accession No. NM_203524.1, Retrieved on Nov. 29, 2018 from https://www.ncbi.nlm.nih.gov/protein/15718763?sat=4&satkey=234448549, 4 pages.
Ostrem, et al., "Development of mutant-specific small molecule inhibitors of K-Ras," Poster, AACR 104th Annual Meeting 2013; Apr. 6-10, 2013; Washington, D.C. (2013).
Ostrem, et al., "K-Ras(G12C) inhibitors allosterically control GTP affinity and effector interactions," *Nature*, 503: 548-551 (2013).

(56) References Cited

OTHER PUBLICATIONS

Paez, et al., "*EGFR* Mutations in Lung Cancer Correlation with Clinical Response to Gefitinib Therapy," *Science*, 304(5676): 1497-500 (2004).
Palmioli, et al., "First experimental identification of Ras-inhibitor binding interface using a water-soluble Ras ligand," *Bioorg. Med. Chem. Lett.*, 19: 4217-4222 (2009).
Patricelli, et al., "Selective Inhibition of Oncogenic KRAS Output with Small Molecules Targeting the Inactive State," *Cancer Discov*, 6 (3): 316-329 (2016).
Peri, et al., "Design, Synthesis and Biological Evaluation of Sugar-Derived Ras Inhibitors," *ChemBioChem*, 6: 1839-1848 (2005).
Peri, et al., "Sugar-Derived Ras Inhibitors: Group Epitope Mapping by NMR Spectroscopy and Biological Evaluation," *Eur. J. Org. Chem.*, 16: 3707-3720 (2006).
Peters, et al., "Selective inhibition of K-Ras G12C through allosteric control of GTP affinity and effector interactions," EORTC Poster (2013).
Remington's Pharmaceutical Sciences, 1435-1712 (18th ed., Mack Publishing Co, Easton, Pennsylvania, 1990 (Table of Contents Only).
Rex et al., "KRAS—AACR 2018," Amgen Collection of Information published at Proceedings of the American Association for Cancer Research Annual Meeting 2018; Apr. 14-18, 2018; Chicago, IL; AACR; slides 1-24 (2018).
Sarkar, et al., "Indole-3-Carbinol and Prostate Cancer[1-2]," *J. Nutr.*, 134(12 Suppl): 3493S-3498S (2004).
Shima, et al., "*In silico* discovery of small-molecule Ras inhibitors that display antitumor activity by blocking the Ras—effector interaction," *PNAS*, 110(20): 8182-8187 (2013).
Singh, et al., "Improving Prospects for Targeting RAS," *J. Clinc. Oncl*, 33(31): 3650-3660 (2015).
Sun, et al., "Discovery of Small Molecules that Bind to K-Ras and Inhibit Sos-Mediated Activation," *Angew. Chem. Int. Ed.*, 51: 6140-6143 (2012).
Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.,*, 5(1): 125-133 (1997).
Teramoto, et al., 1996, Cancer 77 (4):639-645.
Thompson, et al., "PD-1 Is Expressed by Tumor-Infiltrating Immune Cells and Is Associated with Poor Outcome for Patients with Renal Cell Carcinoma," *Clin. Cancer Res.*, 13(6): 1757-1761 (2007).
Traxler, "Tyrosine kinase inhibitors in cancer treatment (Part Ii)," *Exp. Opin. Ther. Patents*, 8(12): 1599-1625 (1998).
Wang, et al., "Ras inhibition via direct Ras binding—is there a path forward?," *Bioorg. Med. Chem. Lett.*, 22: 5766-5776 (2012).
Written Opinion for PCT/US2017/067801, dated Jul. 25, 2018, 10 pages.
Written Opinion for PCT/US2018/033714, dated Jul. 17, 2018, 5 pages.
Xiong, et al., "Covalent Guanosine Mimetic Inhibitors of G12C KRAS," *ACS Med. Chem. Lett.*, 8: 61-66 (2017).
Yan, et al., "Pharmacogenetics and pharmacogenomics in oncology therapeutic antibody development," *BioTechniques*, 29(4): 565-568 (2005).
Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).
Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).
Zeng, et al., "Potent and Selective Covalent Quinazoline Inhibitors of KRAS G12C," *Cell Chemical Biology*, 24: 1-12 (2017).
Zimmerman, et al., "Small molecule inhibition of the KRAS—PDEδ interaction impairs oncogenic KRAS signaling," *Nature*, 1-5 (2017).

"A Phase 1, Study Evaluating the Safety, Tolerability, PK, and Efficacy of AMG 510 in Subjects With Solid Tumors With a S Mutation." NCT03600883, comparison of version submitted Jul. 17, 2018 and Aug. 7, 2018 (update posted Apr. 5, 2019), for full history of changes see https://clinicaltrials.gov/ct2/history/NCT03600883 (last accessed Nov. 13, 2020), pp. 1-17.
"Acute Leukemia," The Merck Manual (Online Edition), pp. 1-6 (2013).
Bhatia, et al., "A Review on Bioisosterism: A Rational Approach for Drug Design and Molecular Modification," *Pharmacologyonline*, 1:272-299 (2011).
Cohen, "The development and therapeutic potential of protein kinase inhibitors," *Current Opinion in Chemical Biology*, 3:459-465 (1999).
Extended European Search Report for European Patent Application No. 19208193.2, dated Jun. 3, 2020, pp. 1-8.
Final Office Action for U.S. Appl. No. 15/984,855, dated Mar. 28, 2019, 7 pages.
Final Office Action for U.S. Appl. No. 16/661,907, dated Mar. 27, 2020, 29 pages.
Golub, et al., "Molecular Classification of Cancer: Class Discovery and Class Prediction by Gene Expression Monitoring," *Science*, 286: 531-537(1999).
Gura, "Cancer Models: Systems for Identifying New Drugs Are Often Faulty," Science, 278(5340):1041-1042 (1997).
Hichri, et al., CAPLUS Abstract, 162:245378 (2015).
International Search Report for PCT/US2018/050044, dated Oct. 30, 2018, 7 pages.
International Search Report for PCT/US2019/030593, dated Aug. 6, 2019, 4 pages.
International Search Report for PCT/US2019/030606, dated Jul. 23, 2019, 5 pages.
International Search Report for PCT/US2019/031535, dated Jul. 25, 2019, 7 pages.
International Search Report for PCT/US2019/034974, dated Aug. 9, 2019, 5 pages.
International Search Report for PCT/US2019/036397, dated Aug. 26, 2019, 5 pages.
International Search Report for PCT/US2019/036626, dated Jun. 2, 2020, 5 pages.
International Search Report for PCT/US2019/061815, dated Mar. 5, 2020, 6 pages.
International Search Report for PCT/US2019/062051, dated Mar. 2, 2020, 3 pages.
International Search Report for PCT/US2019/62064, dated Oct. 29, 2020, 9 pages.
International Search Report for PCT/US2020/032686, dated Aug. 14, 2020, 4 pages.
International Search Report for PCT/US2020/033831, dated Jul. 9, 2020, 6 pages.
International Search Report for PCT/US2020/033832, dated Jul. 8, 2020, 4 pages.
Johnson et al., "Relationships between drug activity in NCI preclinical in vitro and in vivo models and early clinical trials," *British Journal of Cancer*, 84(10): 1424-1431 (2001).
Morrissey et al., "Immunotherapy and Novel Combinations in Oncology: Current Landscape, Challenges, and Opportunities," *Clin. Transl. Sci.*, 9(2):89-104 (2016).
Non-Final Office Action (Corrected) for U.S. Appl. No. 16/125,359, dated Apr. 8, 2019, 13 pages.
Non-Final Office Action for U.S. Appl. No. 15/849,905, dated Mar. 20, 2019, 18 pages.
Non-Final Office Action for U.S. Appl. No. 15/984,855, dated Sep. 27, 2018, 25 pages.
Non-Final Office Action for U.S. Appl. No. 16/125,359, dated Apr. 5, 2019, 13 pages.
Non-Final Office Action for U.S. Appl. No. 16/402,538, dated Oct. 30, 2019, 12 pages.
Non-Final Office Action for U.S. Appl. No. 16/402,589, dated Mar. 6, 2020, 17 pages.
Non-Final Office Action for U.S. Appl. No. 16/407,889, dated Jul. 1, 2020, 6 pages.

(56) References Cited

OTHER PUBLICATIONS

Non-Final Office Action for U.S. Appl. No. 16/428,163, dated Sep. 15, 2020, 6 pages.
Non-Final Office Action for U.S. Appl. No. 16/436,647, dated Aug. 7, 2020, 19 pages.
Non-Final Office Action for U.S. Appl. No. 16/438,349, dated Dec. 13, 2019, 15 pages.
Non-Final Office Action for U.S. Appl. No. 16/661,907, dated Nov. 18, 2019, 20 pages.
Notice of Allowance dated Jul. 24, 2020 for U.S. Appl. No. 16/402,538, 8 pages.
Notice of Allowance dated Sep. 16, 2020 for U.S. Appl. No. 16/402,589, 5 pages.
Notice of Allowance dated Sep. 9, 2020 for U.S. Appl. No. 16/438,349, 9 pages.
Pearce, et al., "Failure modes in anticancer drug discovery and development," *Cancer Drug Design and Discovery*, Edited by Stephen Neidle, Chapter 18, pp. 424-435 (2008).
Simone, "Part XIV Oncology: Introduction," *Cecil Textbook of Medicine*, 20$^{th}$ Edition, 1:1004-1010 (1996).
Statsyuk, "Let K-Ras activate its own inhibitor," *Nature Structural & Molecular Biology*, 25:435-439 (2018).
The ASCO Post Staff, "AACR-NCI-EORTC: Investigational KRAS G12C Inhibitor for KRAS-Mutant Solid Tumors," The ASCO Post (2019).
U.S. Appl. No. 60/528,340, filed Dec. 9, 2003.
Written Opinion for PCT/US2018/050044, dated Oct. 30, 2018, 7 pages.
Written Opinion for PCT/US2019/030593, dated Aug. 6, 2019, 5 pages.
Written Opinion for PCT/US2019/030606, dated Jul. 23, 2019, 6 pages.
Written Opinion for PCT/US2019/031535, dated Jul. 25, 2019, 7 pages.
Written Opinion for PCT/US2019/034974, dated Aug. 9, 2019, 5 pages.
Written Opinion for PCT/US2019/036397, dated Aug. 26, 2019, 5 pages.
Written Opinion for PCT/US2019/036626, dated Jun. 2, 2020, 12 pages.
Written Opinion for PCT/US2019/061815, dated Mar. 5, 2020, 4 pages.
Written Opinion for PCT/US2019/062051, dated Mar. 2, 2020, 5 pages.
Written Opinion for PCT/US2019/62064, dated Oct. 29, 2020, 13 pages.
Written Opinion for PCT/US2020/032686, dated Aug. 14, 2020, 6 pages.
Written Opinion for PCT/US2020/033831, dated Jul. 9, 2020, 7 pages.
Written Opinion for PCT/US2020/033832, dated Jul. 8, 2020, 6 pages.
Notice of Allowance dated Nov. 16, 2020 for U.S. Appl. No. 16/402,538, 8 pages.
Notice of Allowance, dated Oct. 20, 2021, for U.S. Appl. No. 16/438,349, 9 pages.
Notice of Allowance, dated Sep. 22, 2021, for U.S. Appl. No. 16/878,824, 8 pages.
Notice of Allowance, dated Sep. 9, 2021, for U.S. Appl. No. 16/675,121, 7 pages.
PubChem CID 108190520, 2-isopropyl-4-methylpyridin-3-amine, available at https://pubchem.ncbi.nlm.nih.gov/compound/108190520 (last accessed Aug. 30, 2021).
AMG-510; CS-0081316; Source: AbaChemScene (CS-0081316); Deposit Date: May 13, 2019 Available Date: May 13, 2019; SID: 384060804[CID: 137278711] (available at https://pubchem.nlm.nih.gov/substance/384060804/).
AMG-510; HY-114277; Source: MedChemexpress MCE (HY-114277); Deposit Date: May 13, 2019 Available Date: May 13, 2019; SID: 384060569[CID: 137278711] (available at https://pubchem.ncbi.nlm.nih.gov/substance/384060569).
Canon, et al., "The clinical KRAS(G12C) inhibitor AMG 510 drives anti-tumour immunity," *Nature*, 575(7781): 217-223 (2019) (Supplementary Material, pp. 1-55).
Database Registry [Online], Chemical Abstracts Service, Columbus, Ohio, US; Jul. 31, 2017 (Jul. 31, 2017), XP002801805, retrieved from STN Database accession No. 2105944-09-8.
Final Office Action for U.S. Appl. No. 16/436,647, dated Mar. 24, 2021, 7 pages.
International Search Report for PCT/US2020/056874, dated Feb. 12, 2021, 7 pages.
International Search Report for PCT/US2020/065050, dated Mar. 29, 2021, 7 pages.
Meanwell, "Synopsis of Some Recent Tactical Application of Bioisosteres in Drug Design," *J. Med. Chem*. 54:2529-2591 (2011).
Non-Final Office Action for U.S. Appl. No. 16/675,121, dated Feb. 2, 2021, 10 pages.
Notice of Allowance dated Jun. 30, 2021 for U.S. Appl. No. 16/438,349, pp. 1-9.
Notice of Allowance, dated Apr. 19, 2021, for U.S. Appl. No. 16/428,163, 9 pages.
Notice of Allowance, dated Mar. 30, 2021, for U.S. Appl. No. 16/402,538, 8 pages.
Shibata et al., "A Convenient Synthesis of 3-Cyano-2-methylpyridines under Ultrasonic Irradiation," *Bull. Chem. Soc. Jpn*., 61:2199-2200 (1988).
Stanetty et al., "Synthesis of Aza Analogs of the Herbicide Sindone B," *Monatshefte Fuer Chemie*, 130:441-450 (1999).
Third Party Observation filed for PCT/US2020/033831, submitted Jan. 15, 2021, 2 pages.
Written Opinion for PCT/US2020/056874, dated Feb. 12, 2021, 10 pages.
Written Opinion for PCT/US2020/065050, dated Mar. 29, 2021, 8 pages.
4-methyl-2-(1-methylethyl)-3-pyridinamine, STN Registry, CAS RN 1698293-93-4, STN entry date May 5, 2015 (May 5, 2015).

* cited by examiner

SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Ser Tyr Asp Met Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2

Leu Ile Ser Gly Gly Gly Ser Gln Thr Tyr Tyr Ala Glu Ser Val Lys
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Pro Ser Gly His Tyr Phe Tyr Ala Met Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Arg Ala Ser Gln Gly Ile Ser Asn Trp Leu Ala
1               5                   10

<210> SEQ ID NO 5
<211> LENGTH: 7

```
<212> TYPE: PRT
<213> ORGANISM: Artificial Sequence
<220> FEATURE:
<223> OTHER INFORMATION: Synthetic peptide

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Gln Gln Ala Glu Ser Phe Pro His Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic peptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Gly Gly Ser Gln Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Ser Pro Ser Gly His Tyr Phe Tyr Ala Met Asp Val Trp Gly Gln
            100                 105                 110

Gly Thr Thr Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Synthetic peptide

<400> SEQUENCE: 8

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Glu Ser Phe Pro His
                 85                  90                  95

Thr Phe Gly Gly Gly Thr Lys Val Glu Ile Lys
            100                 105

<210> SEQ ID NO 9
<211> LENGTH: 472
<212> TYPE: PRT
<213> ORGANISM: Artificial Sequence
<220> FEATURE:
<223> OTHER INFORMATION: Synthetic peptide

<400> SEQUENCE: 9

Met Asp Met Arg Val Pro Ala Gln Leu Leu Gly Leu Leu Leu Leu Trp
 1               5                  10                  15

Leu Arg Gly Ala Arg Cys Glu Val Gln Leu Leu Glu Ser Gly Gly Gly
                 20                  25                  30

Leu Val Gln Pro Gly Gly Ser Leu Arg Leu Ser Cys Ala Ala Ser Gly
             35                  40                  45

Phe Thr Phe Ser Ser Tyr Asp Met Ser Trp Val Arg Gln Ala Pro Gly
 50                  55                  60

Lys Gly Leu Glu Trp Val Ser Leu Ile Ser Gly Gly Ser Gln Thr
 65                  70                  75                  80

Tyr Tyr Ala Glu Ser Val Lys Gly Arg Phe Thr Ile Ser Arg Asp Asn
                 85                  90                  95

Ser Lys Asn Thr Leu Tyr Leu Gln Met Asn Ser Leu Arg Ala Glu Asp
            100                 105                 110

Thr Ala Val Tyr Phe Cys Ala Ser Pro Ser Gly His Tyr Phe Tyr Ala
            115                 120                 125

Met Asp Val Trp Gly Gln Gly Thr Thr Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Cys Glu Glu Gln
305                 310                 315                 320
```

Tyr Gly Ser Thr Tyr Arg Cys Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 10
<211> LENGTH: 236
<212> TYPE: PRT
<213> ORGANISM: Artificial Sequence
<220> FEATURE:
<223> OTHER INFORMATION: Synthetic peptide

<400> SEQUENCE: 10

Met Asp Met Arg Val Pro Ala Gln Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Asn Trp Leu Ala Trp Tyr Gln Gln Lys Pro Gly Lys
    50                  55                  60

Ala Pro Lys Leu Leu Ile Phe Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Glu Ser Phe Pro His Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 11
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 11
agctatgaca tgagc                                                         15

<210> SEQ ID NO 12
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 12
cttattagtg gtggtggtag tcaaacatac tacgcagaat ccgtgaaggg c                  51

<210> SEQ ID NO 13
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 13
cccagtggcc actacttcta cgctatggac gtc                                     33

<210> SEQ ID NO 14
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 14
cgggcgagtc agggtattag caactggtta gcc                                     33

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 15
gctgcatcca gtttgcaaag t                                                  21

<210> SEQ ID NO 16
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 16
caacaggctg aaagtttccc tcacact                                            27

```
<210> SEQ ID NO 17
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 17
gaggtgcagc tgttggagtc tgggggaggc ttggtacagc ctgggggtc cctgagactc      60 tcctgtgcag cctctggatt cacctttagc agctatgaca tgagctgggt ccgccaggct    120
ccagggaagg ggctggaatg ggtctcactt attagtggtg gtggtagtca aacatactac    180
gcagaatccg tgaagggccg gttcaccatc tccagagaca attccaagaa cacgctgtat    240
ctgcaaatga acagcctgag agccgaggac acggccgtat atttctgtgc gtcccccagt    300
ggccactact tctacgctat ggacgtctgg ggccaaggga ccacggtcac cgtctcctca    360

<210> SEQ ID NO 18
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 18
gacatccaga tgacccagtc tccatcttcc gtgtctgcat ctgttggaga cagagtcacc      60
atcacttgtc gggcgagtca gggtattagc aactggttag cctggtatca gcagaaacca    120
gggaaagccc ctaagctcct gatctttgct gcatccagtt tgcaaagtgg ggtcccatca    180
aggttcagcg gcagtggatc tgggacagat ttcaccctca ccatcagcag cctgcagcct    240
gaagattttg caacttacta ttgtcaacag gctgaaagtt tccctcacac tttcggcgga    300
gggaccaagg tggagatcaa a                                              321

<210> SEQ ID NO 19
<211> LENGTH: 1416
<212> TYPE: DNA
<213> ORGANISM: Artificial Sequence
<220> FEATURE:
<223> OTHER INFORMATION: Synthetic polynucleotide

<400> SEQUENCE: 19
atggacatga gggtgcccgc tcagctcctg gggctcctgc tgctgtggct gagaggtgcg      60
cgctgtgagg tgcagctgtt ggagtctggg ggaggcttgg tacagcctgg ggggtccctg    120
agactctcct gtgcagcctc tggattcacc tttagcagct atgacatgag ctgggtccgc    180
caggctccag ggaagggct ggaatgggtc tcacttatta gtggtggtgg tagtcaaaca    240
tactacgcag aatccgtgaa gggccggttc accatctcca gagacaattc caagaacacg    300
ctgtatctgc aaatgaacag cctgagagcc gaggacacgg ccgtatattt ctgtgcgtcc    360
cccagtggcc actacttcta cgctatggac gtctggggcc aagggaccac ggtcaccgtc    420
tcctcagcct ccaccaaggg cccatcggtc ttccccctgg cacctcctc caagagcacc    480 tctgggggca cagcggccct gggctgcctg gtcaaggact acttccccga accggtgacg    540
gtgtcgtgga actcaggcgc cctgaccagc ggcgtgcaca ccttcccggc tgtcctacag    600
```

-continued

```
tcctcaggac tctactccct cagcagcgtg gtgaccgtgc cctccagcag cttgggcacc      660
cagacctaca tctgcaacgt gaatcacaag cccagcaaca ccaaggtgga caagaaagtt      720
gagcccaaat cttgtgacaa aactcacaca tgcccaccgt gcccagcacc tgaactcctg      780
gggggaccgt cagtcttcct cttccccca aaacccaagg acaccctcat gatctcccgg       840 accccctgagg tcacatgcgt ggtggtggac gtgagccacg aagaccctga ggtcaagttc     900
aactggtacg tggacggcgt ggaggtgcat aatgccaaga caaagccgtg cgaggagcag     960
tacggcagca cgtaccgttg cgtcagcgtc ctcaccgtcc tgcaccagga ctggctgaat     1020
ggcaaggagt acaagtgcaa ggtgtccaac aaagcccctcc cagcccccat cgagaaaacc    1080
atctccaaag ccaaagggca gccccgagaa ccacaggtgt acaccctgcc cccatcccgg    1140
gaggagatga ccaagaacca ggtcagcctg acctgcctgg tcaaaggctt ctatcccagc    1200
gacatcgccg tggagtggga gagcaatggg cagccggaga caactacaa gaccacgcct     1260 cccgtgctgg actccgacgg ctccttcttc ctctatagca agctcaccgt ggacaagagc    1320
aggtggcagc aggggaacgt cttctcatgc tccgtgatgc atgaggctct gcacaaccac    1380
tacacgcaga gagcctctc cctgtctccg ggtaaa                              1416
```

<210> SEQ ID NO 20
<211> LENGTH: 708
<212> TYPE: DNA
<213> ORGANISM: Artificial Sequence
<220> FEATURE:
<223> OTHER INFORMATION: Synthetic polynucleotide

<400> SEQUENCE: 20

```
atggacatga gggtgcccgc tcagctcctg gggctcctgc tgctgtggct gagaggtgcg       60
cgctgtgaca tccagatgac ccagtctcca tcttccgtgt ctgcatctgt tggagacaga      120
gtcaccatca cttgtcgggc gagtcagggt attagcaact ggttagcctg gtatcagcag      180
aaaccaggga aagcccctaa gctcctgatc tttgctgcat ccagtttgca aagtggggtc      240
ccatcaaggt tcagcggcag tggatctggg acagatttca ccctcaccat cagcagcctg      300
cagcctgaag attttgcaac ttactattgt caacaggctg aaagtttccc tcacactttc      360
ggcggaggga ccaaggtgga gatcaaacga acggtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc     600
ctgacgctga gcaaagcaga ctacgagaaa cacaaagtct acgcctgcga agtcacccat    660
cagggcctga gctcgcccgt cacaaagagc ttcaacaggg gagagtgt                 708
```

INHIBITORS OF KRAS G12C AND METHODS OF USING THE SAME

CROSS-REFERENCE TO RELATED APPLICATIONS

This application is a continuation of U.S. patent application Ser. No. 16/125,359, filed on Sep. 7, 2018 which claims the benefit of U.S. Provisional Patent Application No. 62/556,223, filed on Sep. 8, 2017, both of which are hereby incorporated by reference in their entireties.

The present application is being filed along with a sequence listing in electronic format. The sequence listing is provided as a file entitled A-2202-US-DIV_SeqList_031220_ST25.txt, created Mar. 12, 2020, which is 15.16 kb in size. The information in the electronic format of the sequence listing is incorporated herein by reference in its entirety.

FIELD OF THE INVENTION

The present invention relates to compounds capable of acting as inhibitors of the KRAS G12C mutant, and compositions that include compounds that are inhibitors of the KRAS G12C mutant. The compounds and compositions may be used to inactivate the KRAS G12C mutant and to treat various disease conditions. An example of one area where such compounds may be used is in the treatment of oncologic conditions.

BACKGROUND

KRAS gene mutations are common in pancreatic cancer, lung adenocarcinoma, colorectal cancer, gall bladder cancer, thyroid cancer, and bile duct cancer. KRAS mutations are also observed in about 25% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation, and including those who have progressed after chemotherapy.

SUMMARY

In one aspect of the present invention, one embodiment comprises a compound having a structure of formula (I)

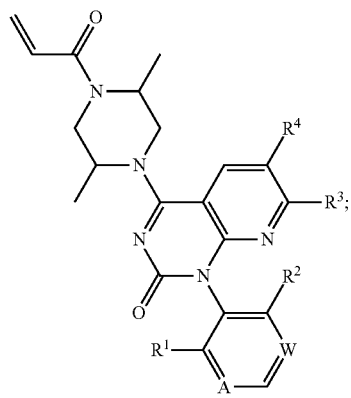

(I)

wherein
A is independently N or CH;
W is independently N or CH;
wherein one or both of A and W is N;
$R^1$ and $R^2$ are independently a branched or a linear $C_{1-6}$alkyl;
$R^3$ is phenyl substituted by 1 or 2 $R^5$ substituents;
$R^5$ is independently selected from one or more halo, —OH, or $NH_2$;
$R^4$ is halo; or
a stereoisomer thereof, a pharmaceutically acceptable salt thereof, a pharmaceutically acceptable salt of the stereoisomer thereof.

In another aspect of the present invention, another embodiment of the present invention comprises a compound of embodiment 1 having a structure of formula (Ia)

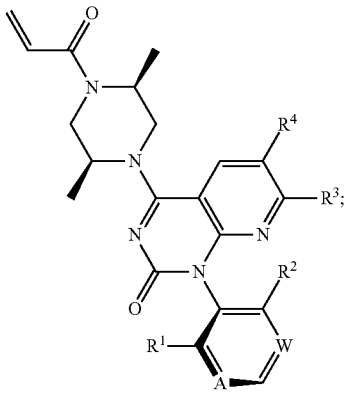

(Ia)

or
a pharmaceutically acceptable salt thereof.
The compound of embodiment 1 or 2 wherein A is N.
The compound of embodiment 1 or 2 wherein A is CH.
The compound of embodiment 1 or 2 wherein W is N.
The compound of embodiment 1 or 2 wherein W is CH.
The compound of any one of embodiments 1-6 wherein $R^1$ is $CH_3$.
The compound of any one of embodiments 1-6 wherein $R^1$ is $CH(CH_3)_2$.
The compound of any one of embodiments 1-8 wherein $R^2$ is $CH_3$.

The compound of any one of embodiments 1-8 wherein $R^2$ is $CH(CH_3)_2$.

The compound of any one of embodiments 1-10 wherein $R^5$ is halo.

The compound of embodiment 11 wherein $R^5$ is F.

The compound of any one of embodiments 1-10 wherein $R^5$ is —OH.

The compound of any one of embodiments 1-10 wherein $R^5$ is —NH$_2$.

The compound of any one of embodiments 1-10 wherein $R^3$ is

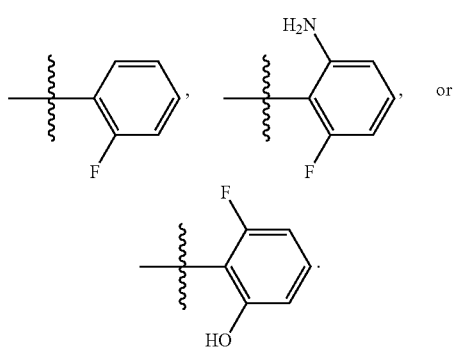

The compound of embodiment 15 wherein $R^3$ is

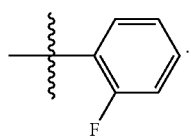 [SMILES: *c1ccccc1F]

The compound of embodiment 15 wherein $R^3$ is

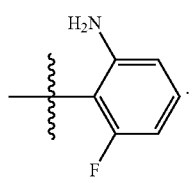

The compound of embodiment 15 wherein $R^3$ is

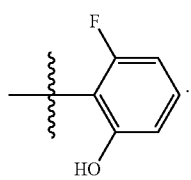 [SMILES: *c1c(O)cccc1F]

The compound of any one of embodiments 1-18 wherein $R^4$ is halo.

The compound of embodiment 19 wherein $R^4$ is Cl.

The compound of embodiment 19 wherein $R^4$ is F.

In another aspect of the present invention, another embodiment of the present invention comprises a compound having a structure of formula (II)

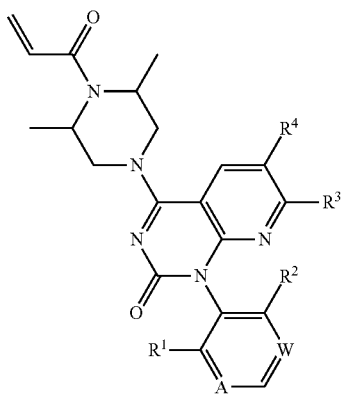

wherein
A is independently N or CH;
W is independently N or CH;
wherein one or both A and W is N;
$R^1$ and $R^2$ are independently a branched or a linear $C_{1-6}$alkyl;
$R^3$ is phenyl substituted by one or two $R^5$ substituents;
$R^5$ is independently selected from one or more halo, —OH, or NH$_2$; and
$R^4$ is halo; or
or a stereoisomer thereof; a pharmaceutically acceptable salt thereof, a pharmaceutically acceptable salt of the stereoisomer thereof.

A compound of embodiment 22 having a structure of formula (IIa)

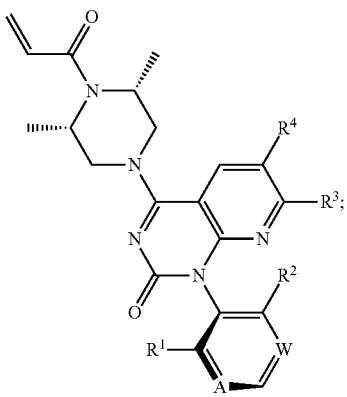

a pharmaceutically acceptable salt thereof.

The compound of embodiment 22 or 23 wherein A is N.
The compound of embodiment 22 or 23 wherein A is CH.
The compound of embodiment 22 or 23 wherein W is N.
The compound of embodiment 22 or 23 wherein W is CH.
The compound of any one of embodiments 22-27 wherein $R^1$ is $CH_3$.
The compound of any one of embodiments 22-27 wherein $R^1$ is $CH(CH_3)_2$.
The compound of any one of embodiments 22-29 wherein $R^2$ is $CH_3$.
The compound of any one of embodiments 22-29 wherein $R^2$ is $CH(CH_3)_2$.

The compound of any one of embodiments 22-31 wherein $R^5$ is halo.

The compound of embodiment 32 wherein $R^5$ is F.

The compound of any one of embodiments 22-31 wherein $R^5$ is —OH.

The compound of any one of embodiments 22-31 wherein $R^5$ is —NH$_2$.

The compound of any one of embodiments 22-31 wherein $R^3$ is

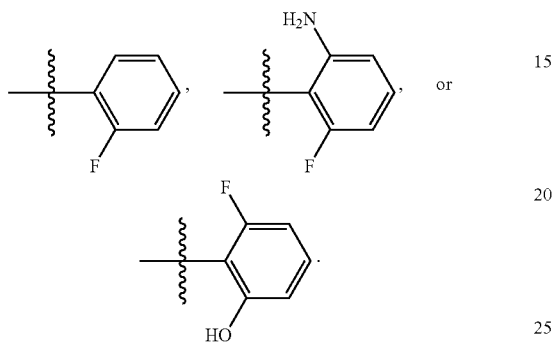

The compound of embodiment 36 wherein $R^3$ is

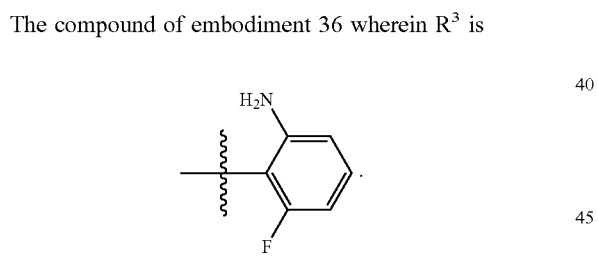

The compound of embodiment 36 wherein $R^3$ is

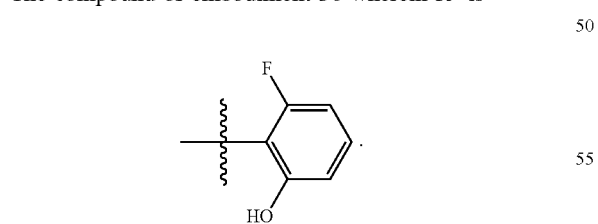

The compound of embodiment 36 wherein $R^3$ is

The compound of any one of embodiments 22-39 wherein $R^4$ is halo.

The compound of embodiment 40 wherein $R^4$ is Cl.

The compound of embodiment 40 wherein $R^4$ is F.

In another aspect of the present invention, another embodiment of the present invention comprises a compound having a structure selected from:

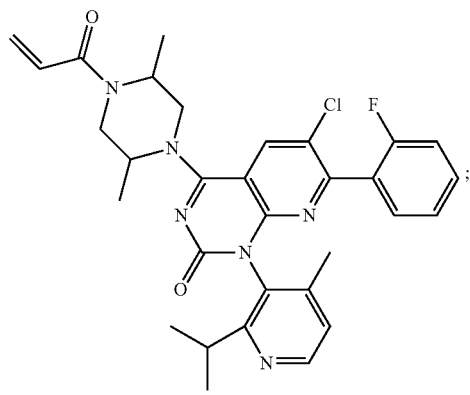

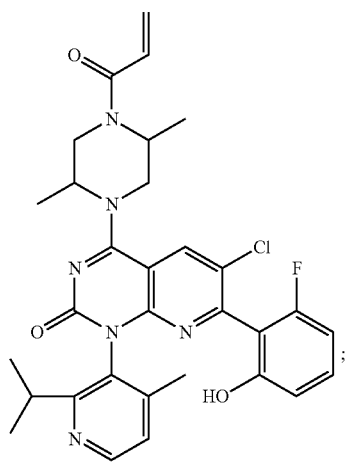

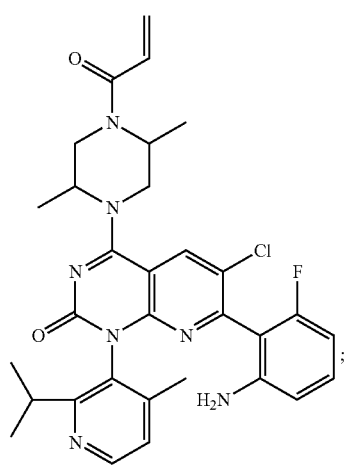

7
-continued
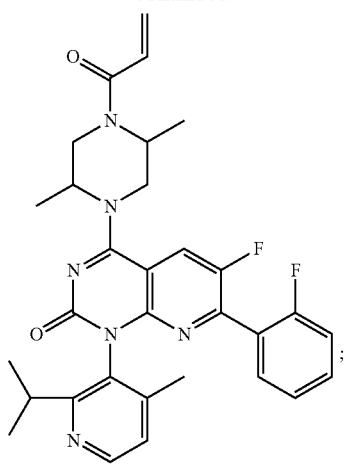
8
-continued
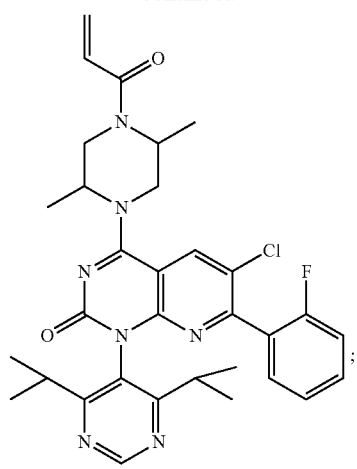
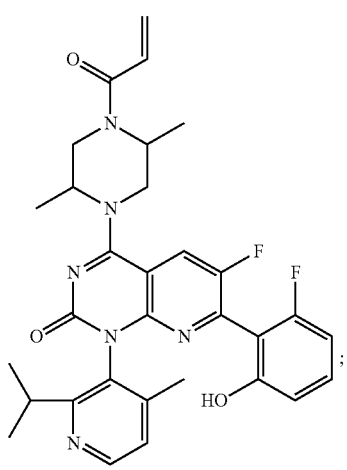
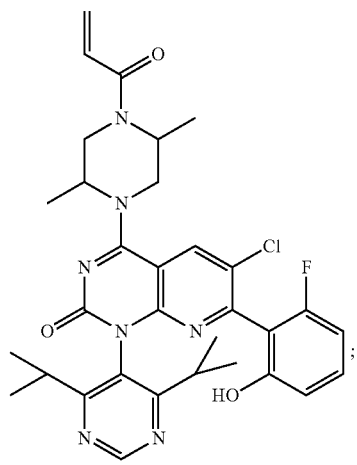
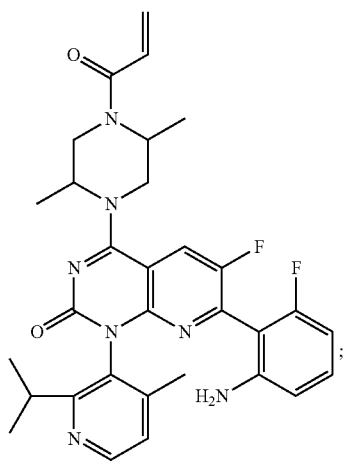
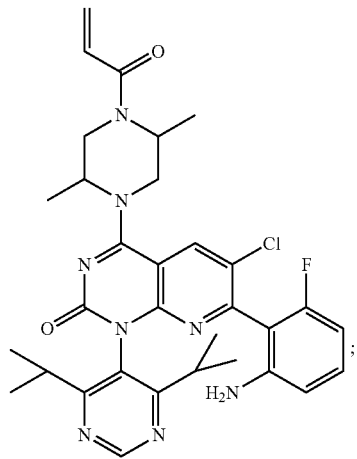

-continued
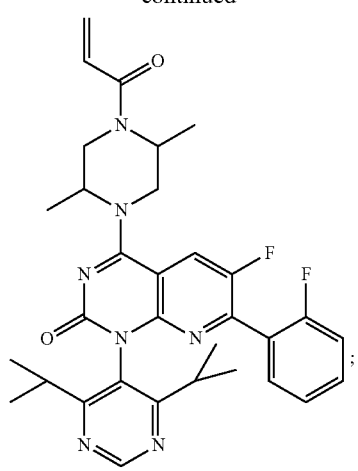
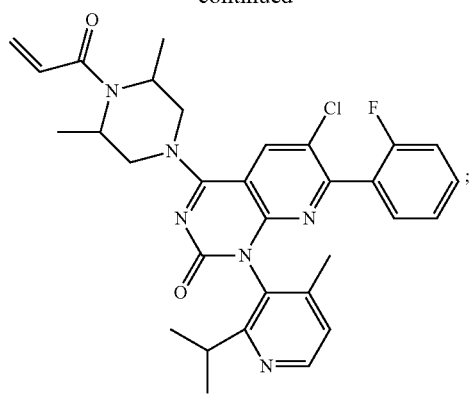
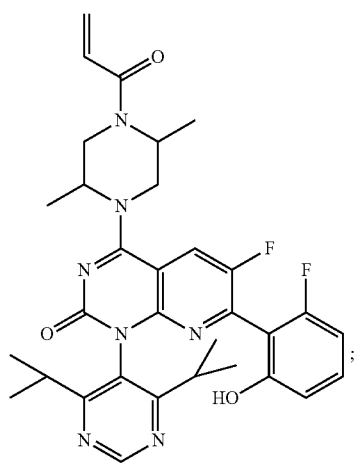
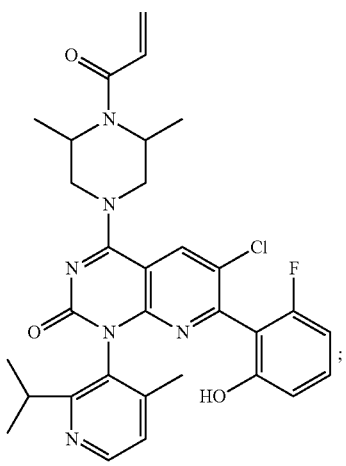
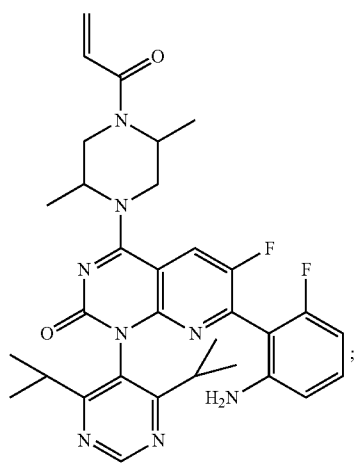
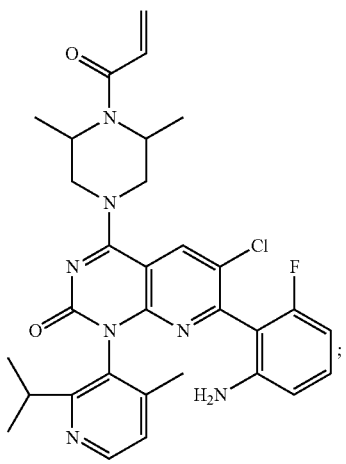

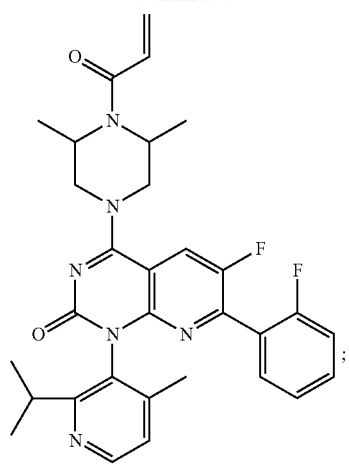
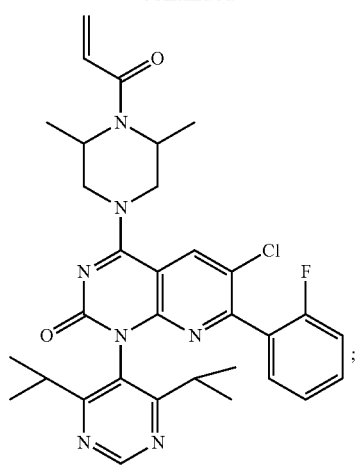
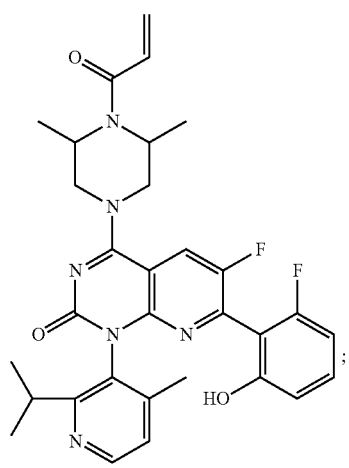
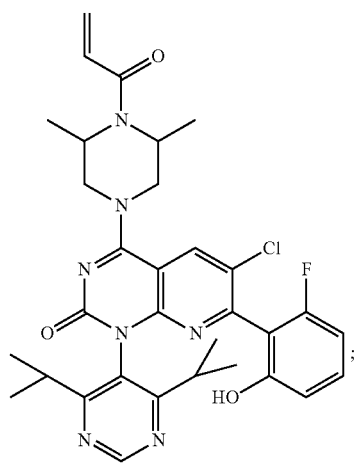
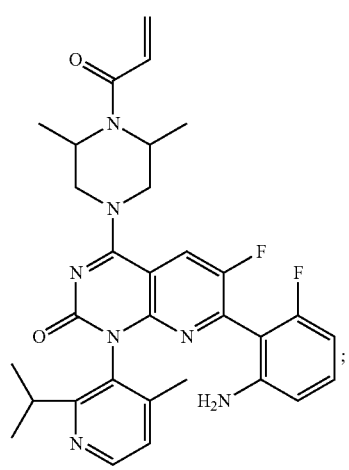
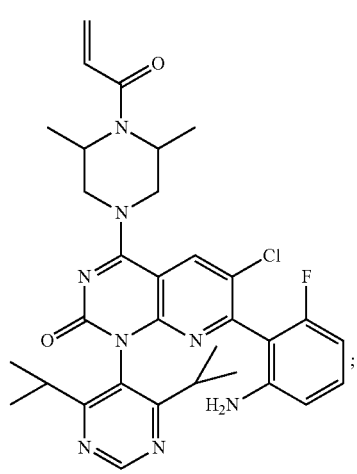

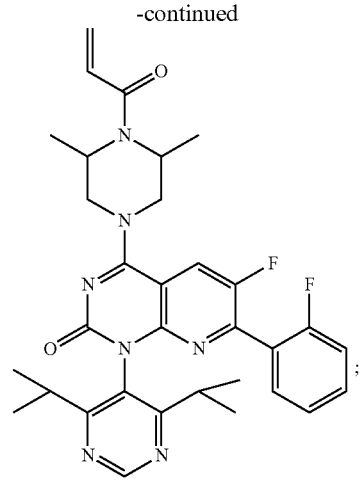
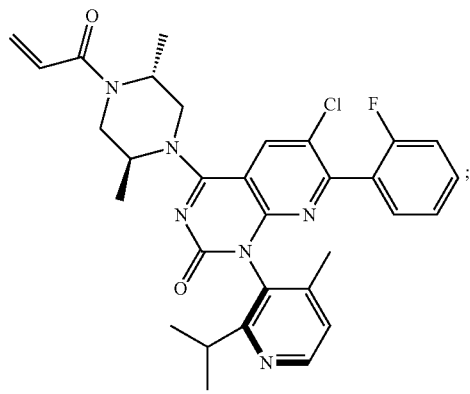
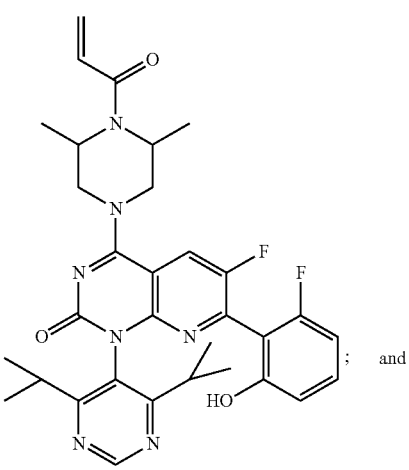
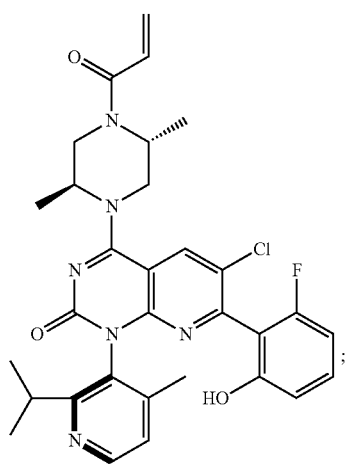
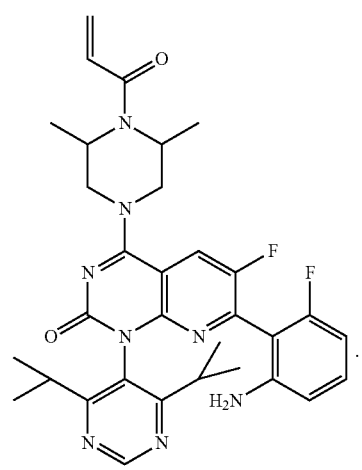
; and
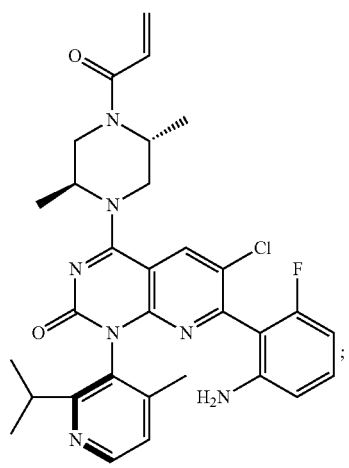
or a stereoisomer thereof; a pharmaceutically acceptable salt thereof, a pharmaceutically acceptable salt of the stereoisomer thereof.
In another aspect of the present invention, another embodiment of the present invention comprises a compound having a structure selected from:

15
-continued
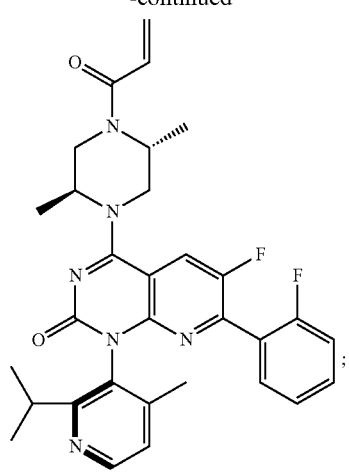
16
-continued
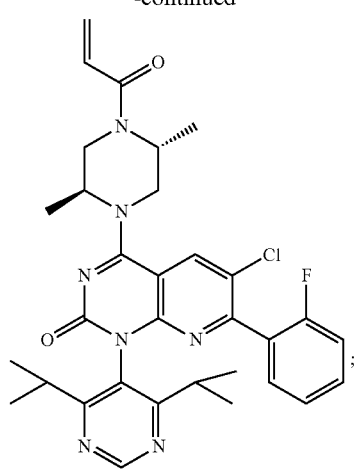
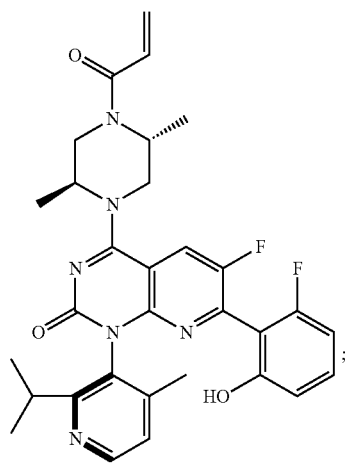
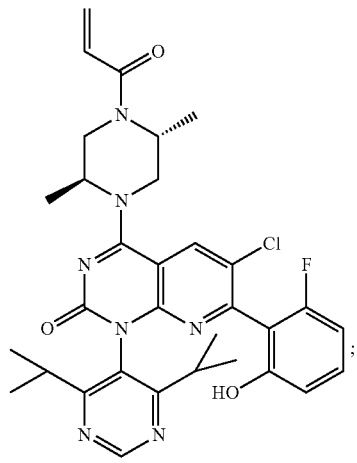
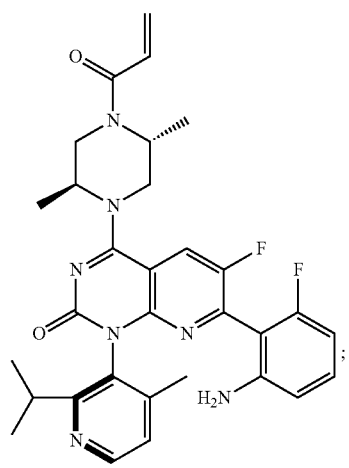
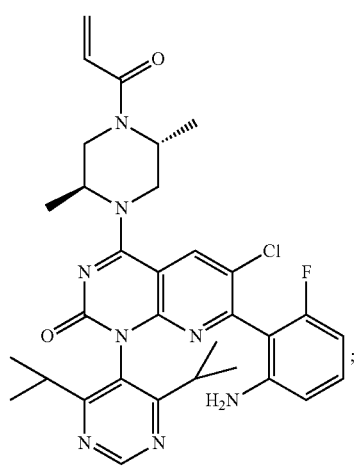

-continued
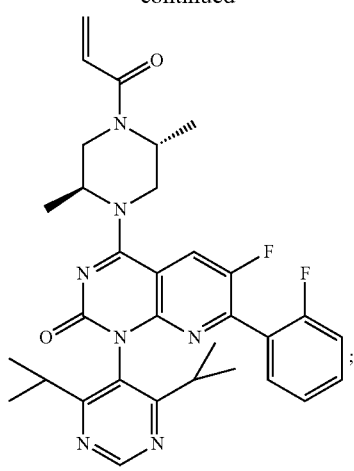
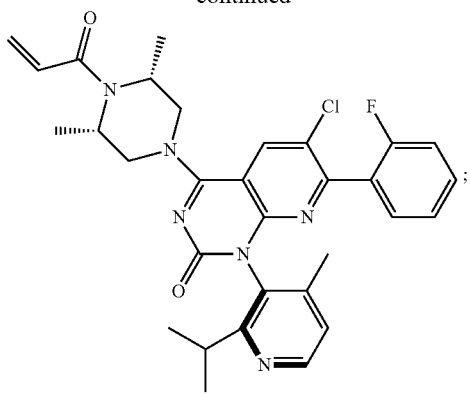
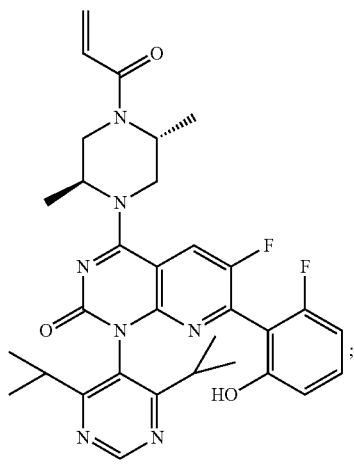
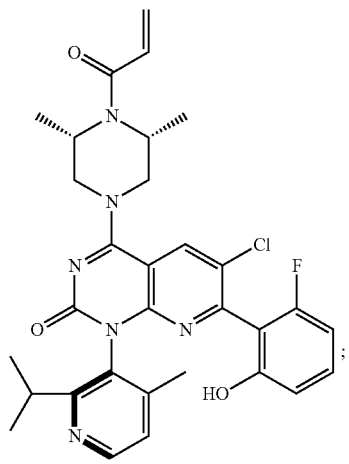
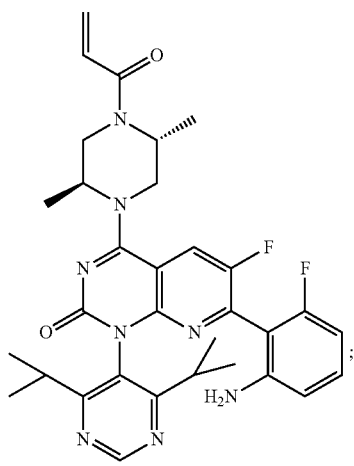
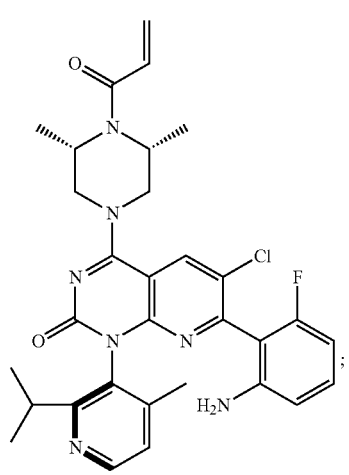

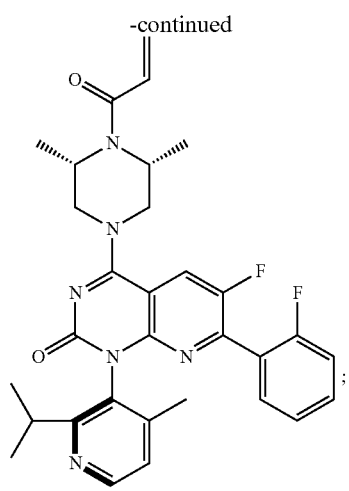
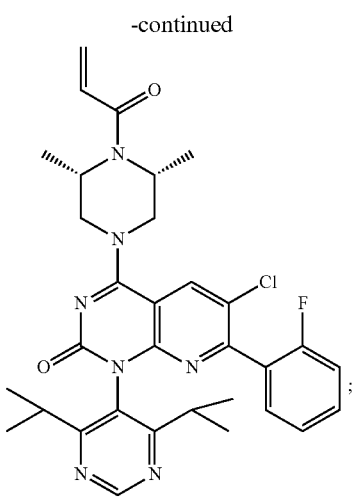
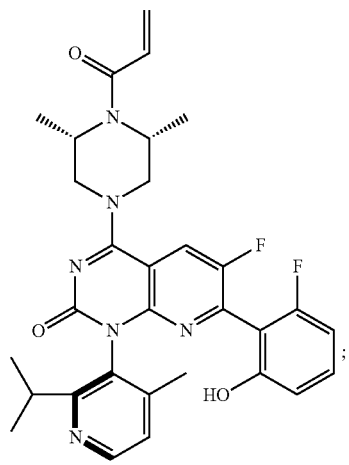
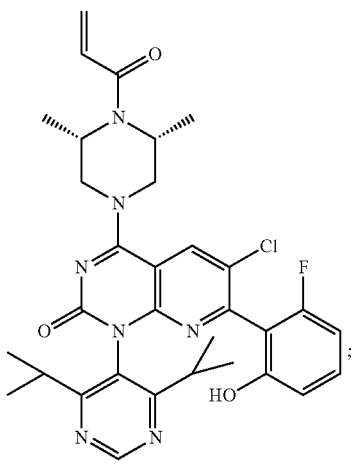
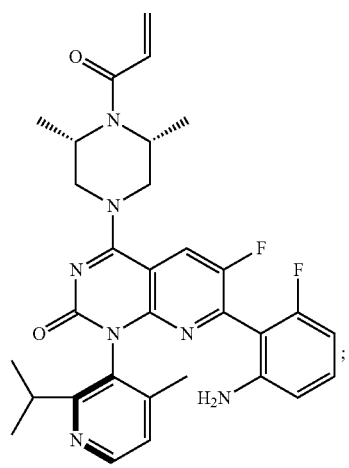
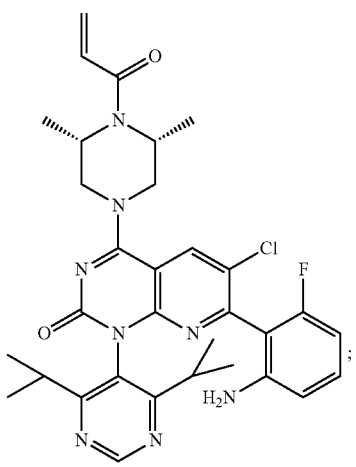

-continued

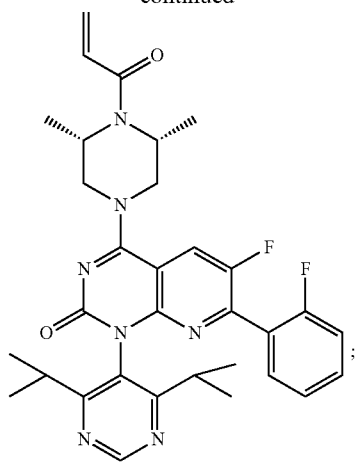

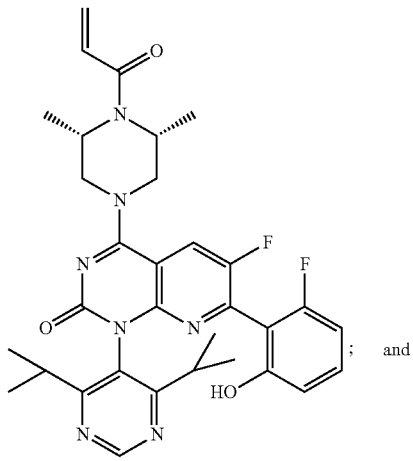

; and

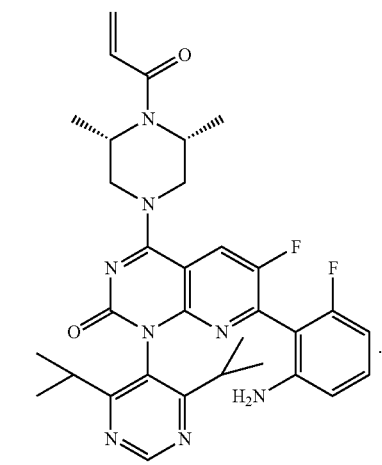

The compound of embodiment 44 in the form of a pharmaceutically acceptable salt.

In another aspect of the present invention, another embodiment of the present invention comprises a pharmaceutical composition comprising the compound of any one of embodiments 1-45 and a pharmaceutically acceptable excipient.

In another aspect of the present invention, another embodiment of the present invention comprises a compound having a structure

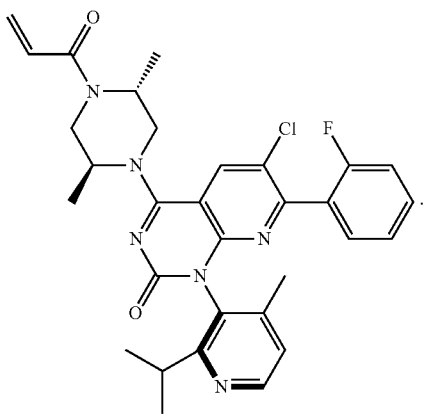

In another aspect of the present invention, another embodiment of the present invention comprises a compound having a structure

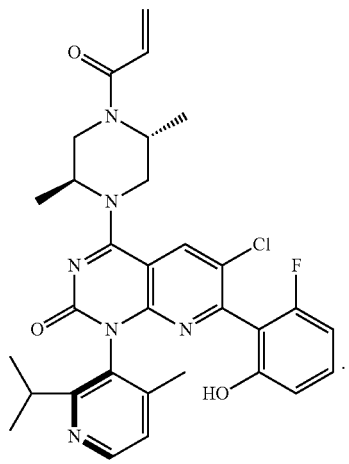

In another aspect of the present invention, another embodiment of the present invention comprises a compound having a structure

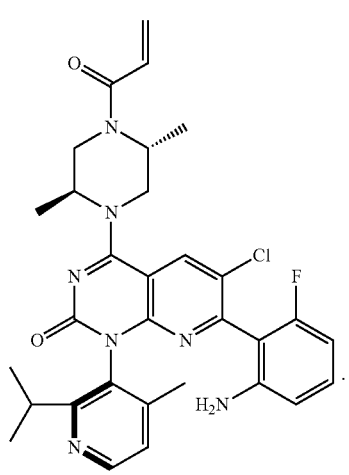

In another aspect of the present invention, another embodiment of the present invention comprises a compound having a structure

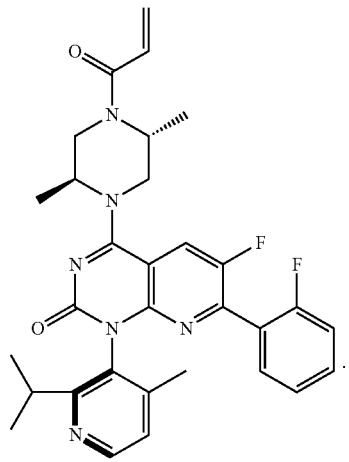

In another aspect of the present invention, another embodiment of the present invention comprises a compound having a structure

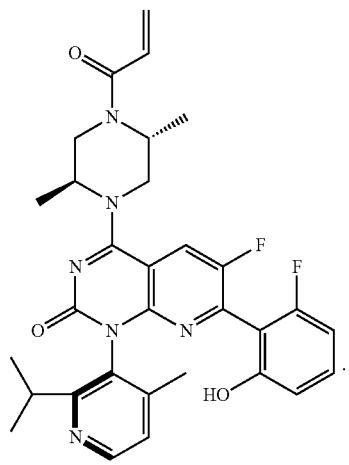

In another aspect of the present invention, another embodiment of the present invention comprises a compound having a structure

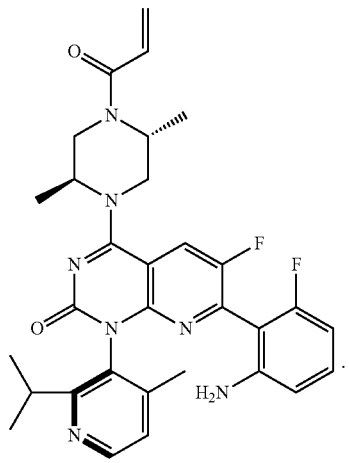

In another aspect of the present invention, another embodiment of the present invention comprises a compound having a structure

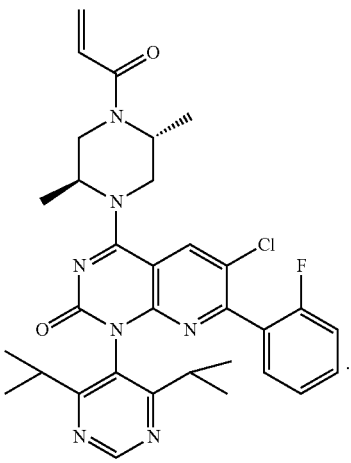 [SMILES: C=CC(=O)N1C[C@H](C)N(c2nc(=O)n(-c3c(C(C)C)ncnc3C(C)C)c3nc(-c4ccccc4F)c(Cl)cc23)C[C@H]1C]

In another aspect of the present invention, another embodiment of the present invention comprises a compound having a structure

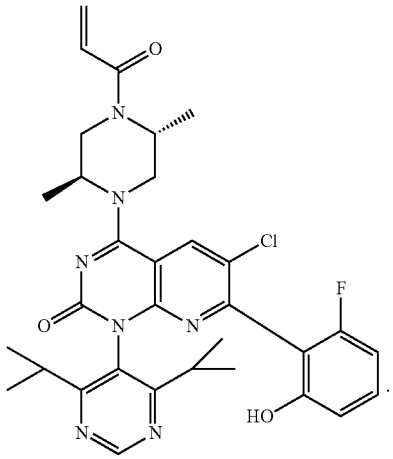 [SMILES: C=CC(=O)N1C[C@H](C)N(c2nc(=O)n(-c3c(C(C)C)ncnc3C(C)C)c3nc(-c4c(O)cccc4F)c(Cl)cc23)C[C@H]1C]

In another aspect of the present invention, another embodiment of the present invention comprises a compound having a structure

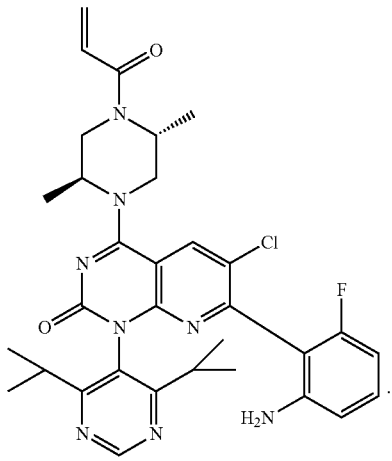 [SMILES: C=CC(=O)N1C[C@H](C)N(c2nc(=O)n(-c3c(C(C)C)ncnc3C(C)C)c3nc(-c4c(N)cccc4F)c(Cl)cc23)C[C@H]1C]

In another aspect of the present invention, another embodiment of the present invention comprises a compound having a structure

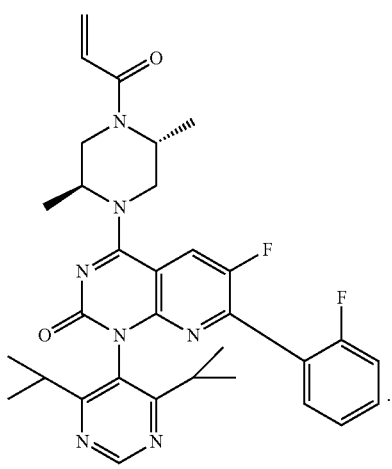 [SMILES: C=CC(=O)N1C[C@H](C)N(c2nc(=O)n(-c3c(C(C)C)ncnc3C(C)C)c3nc(-c4ccccc4F)c(F)cc23)C[C@H]1C]

In another aspect of the present invention, another embodiment of the present invention comprises a compound having a structure

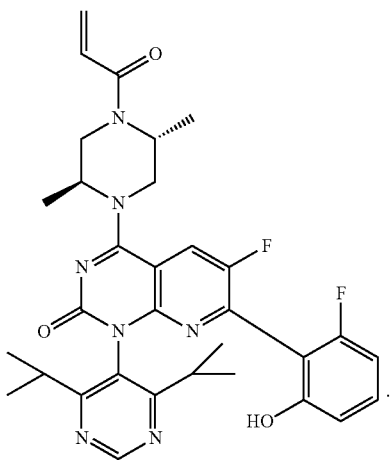 [SMILES: C=CC(=O)N1C[C@H](C)N(c2nc(=O)n(-c3c(C(C)C)ncnc3C(C)C)c3nc(-c4c(O)cccc4F)c(F)cc23)C[C@H]1C]

In another aspect of the present invention, another embodiment of the present invention comprises a compound having a structure

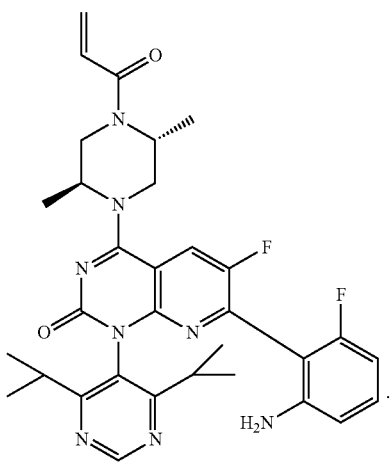 [SMILES: C=CC(=O)N1C[C@H](C)N(c2nc(=O)n(-c3c(C(C)C)ncnc3C(C)C)c3nc(-c4c(N)cccc4F)c(F)cc23)C[C@H]1C]

In another aspect of the present invention, another embodiment of the present invention comprises a compound having a structure

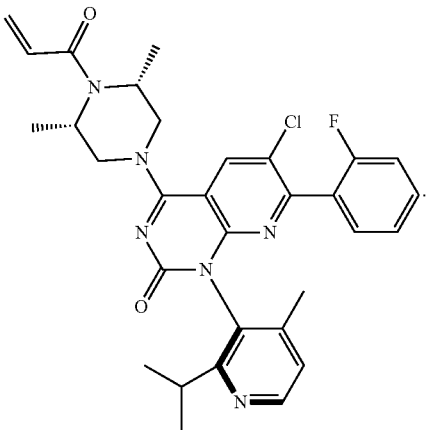

In another aspect of the present invention, another embodiment of the present invention comprises a compound having a structure

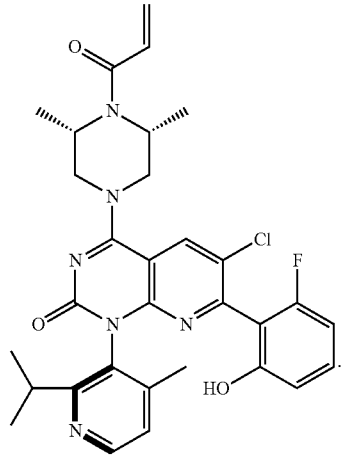

In another aspect of the present invention, another embodiment of the present invention comprises a compound having a structure

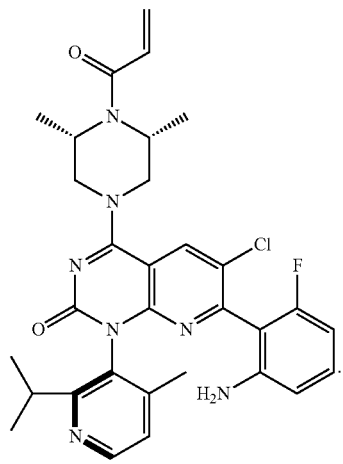

In another aspect of the present invention, another embodiment of the present invention comprises a compound having a structure

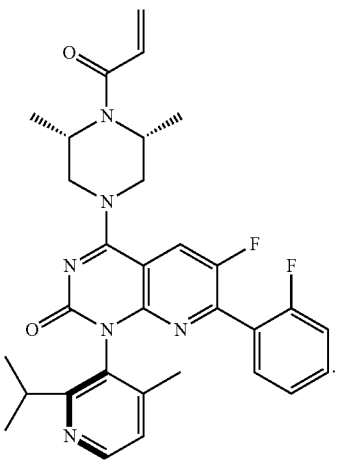

In another aspect of the present invention, another embodiment of the present invention comprises a compound having a structure

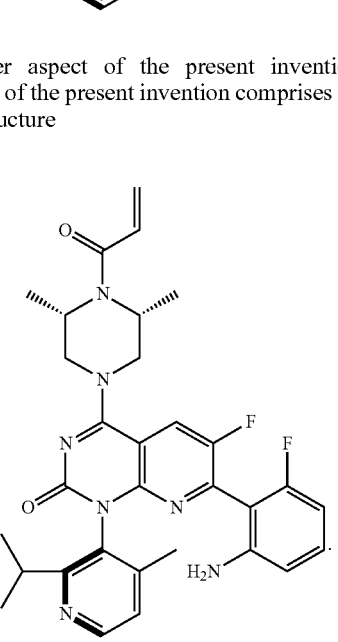

In another aspect of the present invention, another embodiment of the present invention comprises a compound having a structure In another aspect of the present invention, another embodiment of the present invention comprises a compound having a structure

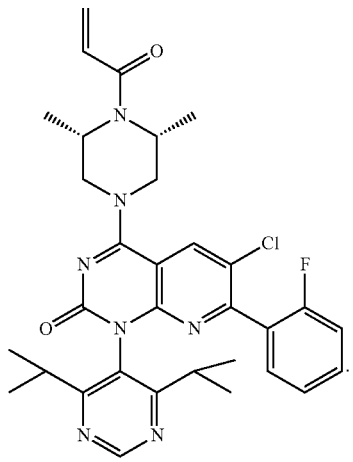 [SMILES: C=CC(=O)N1[C@H](C)CN(c2nc(=O)n(-c3c(C(C)C)ncnc3C(C)C)c3nc(-c4ccccc4F)c(Cl)cc23)C[C@@H]1C]

In another aspect of the present invention, another embodiment of the present invention comprises a compound having a structure

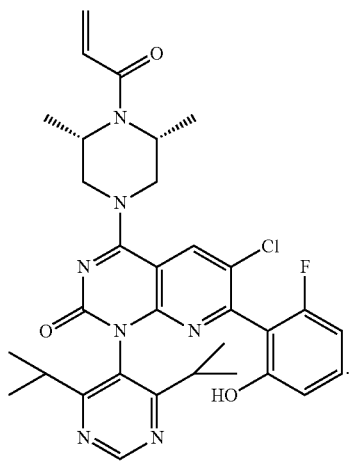 [SMILES: C=CC(=O)N1[C@H](C)CN(c2nc(=O)n(-c3c(C(C)C)ncnc3C(C)C)c3nc(-c4c(O)cccc4F)c(Cl)cc23)C[C@@H]1C]

In another aspect of the present invention, another embodiment of the present invention comprises a compound having a structure

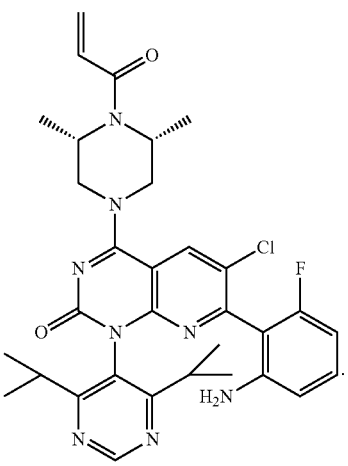

In another aspect of the present invention, another embodiment of the present invention comprises a compound having a structure

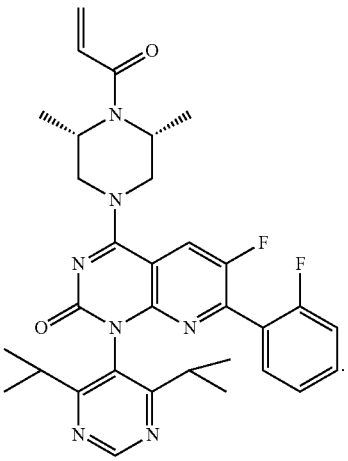 [SMILES: C=CC(=O)N1[C@H](C)CN(c2nc(=O)n(-c3c(C(C)C)ncnc3C(C)C)c3nc(-c4ccccc4F)c(F)cc23)C[C@@H]1C]

In another aspect of the present invention, another embodiment of the present invention comprises a compound having a structure

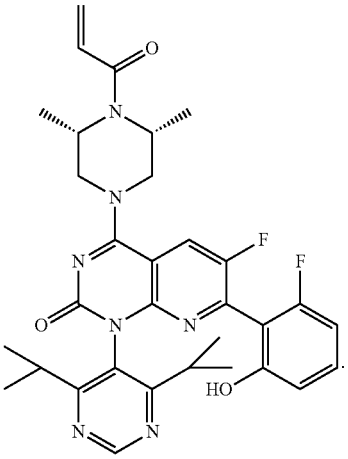 [SMILES: C=CC(=O)N1[C@H](C)CN(c2nc(=O)n(-c3c(C(C)C)ncnc3C(C)C)c3nc(-c4c(O)cccc4F)c(F)cc23)C[C@@H]1C]

In another aspect of the present invention, another embodiment of the present invention comprises a compound having a structure

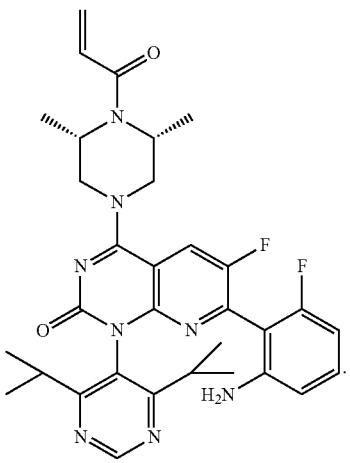 [SMILES: C=CC(=O)N1[C@H](C)CN(c2nc(=O)n(-c3c(C(C)C)ncnc3C(C)C)c3nc(-c4c(N)cccc4F)c(F)cc23)C[C@@H]1C]

In another aspect of the present invention, another embodiment of the present invention comprises the compound of any one of embodiments 47 to 70 in the form of a pharmaceutically acceptable salt.

In another aspect of the present invention, another embodiment of the present invention comprises a pharmaceutical composition comprising the compound of any one of embodiments 1-45 and 47-71 and a pharmaceutically acceptable excipient.

In another aspect of the present invention, another embodiment of the present invention comprises a method of inhibiting KRAS G12C in a cell, comprising contacting the cell with the compound of any one of embodiments 1-45 and 47-71 or the composition of embodiment 46 or 72.

In another aspect of the present invention, another embodiment of the present invention comprises a method of treating cancer in a subject comprising administering to the subject a therapeutically effective amount of the compound of any one of embodiments 1-45 and 47-71 or the composition of embodiment 46 or 72.

The method of embodiment 74, wherein the cancer is lung cancer, pancreatic cancer, or colorectal cancer.

Numerous other embodiments of the compound of Formulas I, Ia, II and IIa are set forth herein.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments.

The compounds disclosed herein can be in the form of a pharmaceutically acceptable salt. The compounds provided can be formulated into a pharmaceutical formulation comprising a compound disclosed herein and a pharmaceutically acceptable excipient.

Also provided is a method of inhibiting KRAS G12C in a cell, comprising contacting the cell with a compound or composition disclosed herein. Further provided is a method of treating cancer in a subject comprising administering to the subject a therapeutically effective amount of a compound or composition disclosed herein. In some embodiments, the cancer is lung cancer, pancreatic cancer, or colorectal cancer.

Other objects, features and advantages of the invention will become apparent to those skilled in the art from the following description and claims.

DETAILED DESCRIPTION

Definitions

Abbreviations: The following abbreviations may be used herein:

| | |
|---|---|
| AcOH | acetic acid |
| aq or aq. | Aqueous |
| BOC or Boc | tert-butyloxycarbonyl |
| cpme | cyclopentyl methyl ether |
| DCE | 1,2-dichloroethane |
| DABCO | 1,4-diazabicyclo[2.2.2]octane |
| DCM | Dichloromethane |
| DMA | N,N-Dimethylacetamide |
| DMAP | 4-dimethylaminopyridine |
| DME | 1,2-dimethoxyethane |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | Equivalent |
| ESI or ES | electrospray ionization |
| Et | Ethyl |
| Et$_2$O | diethyl ether |
| EtOAc | ethyl acetate |
| g | Grams |
| h | Hour |
| HPLC | high pressure liquid chromatography |
| iPr | Isopropyl |
| iPr$_2$NEt or DIPEA | N-ethyl diisopropylamine (Hünig's base) |
| KHMDS | potassium hexamethyldisilazide |
| KOAc | potassium acetate |
| Lawesson's reagent | 2,4-bis(4-methoxyphenyl)-2,4-dithioxo-1,3,2,4-dithiadiphosphetane, 2,4-Bis-(4-methoxyphenyl)-1,3-dithia-2,4-diphosphetane 2,4-disulfide |
| LC MS, LCMS, LC-MS or LC/MS | liquid chromatography mass spectroscopy |
| LG | Leaving group (e.g., halogen, mesylate, triflate) |
| LHMDS or LiHMDS | lithium hexamethyldisilazide |
| m/z | mass divided by charge |
| Me | Methyl |
| MeCN | Acetonitrile |
| MeOH | Methanol |
| Met | Metal species for cross-coupling (e.g., MgX, ZnX, SnR$_3$, SiR$_3$, B(OR)$_2$) |
| mg | Milligrams |
| min | Minutes |
| mL | Milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| Pd$_2$(dba)$_3$ | tris(dibenzylideneacetone)dipalladium(0) |
| Pd(dppf)Cl$_2$•DCM | [1,1'-Bis(diphenylphosphino)ferrocene]dichloropalladium(II), complex with dichloromethane |
| Pd(PPh$_3$)$_4$ | Tetrakis(triphenylphosphine)palladium(0) |
| Ph | Phenyl |
| PR or PG or Prot. group | protecting group |
| rbf | round-bottom flask |
| RP-HPLC | reverse phase high pressure liquid chromatography |
| RT or rt | room temperature |
| sat. or satd. | saturated |
| SFC | supercritical fluid chromatography |
| SPhos Pd G3 or SPhos G3 | (2-Dicyclohexylphosphino-2',6'-dimethoxybiphenyl) [2-(2'-amino-1,1'-biphenyl)]palladium(II)methanesulfonate |
| TBAF | tetra-n-butylammonium fluoride |

| | |
|---|---|
| TBTU | N,N,N',N'-Tetramethyl-O-(benzotriazol-1-yl)uronium tetrafluoroborate |
| t-BuOH | tert-butanol |
| TEA or Et₃N | Trimethylamine |
| TFA | trifluoroacetic acid |
| THF | Tetrahydrofuran |
| UV | Ultraviolet |

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched C1-C8 hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term Cm-n means the alkyl group has "m" to "n" carbon atoms. The term "alkylene" refers to an alkyl group having a substituent. An alkyl (e.g., methyl), or alkylene (e.g., —CH2-), group can be substituted with one or more, and typically one to three, of independently selected, for example, halo, trifluoromethyl, trifluoromethoxy, hydroxy, alkoxy, nitro, cyano, alkylamino, —C1-8alkyl, —C2-8alkenyl, —C2-8alkynyl, —NC, amino, —CO2H, —CO2C1-C8alkyl, —OCOC1-C8alkyl, —C3-C10 cycloalkyl, —C3—C10 heterocycloalkyl, —C5-C10aryl, and —C5-C10 heteroaryl. The term "haloalkyl" specifically refers to an alkyl group wherein at least one, e.g., one to six, or all of the hydrogens of the alkyl group are substituted with halo atoms.

The terms "alkenyl" and "alkynyl" indicate an alkyl group that further includes a double bond or a triple bond, respectively.

As used herein, the term "halo" refers to fluoro, chloro, bromo, and iodo. The term "alkoxy" is defined as —OR, wherein R is alkyl.

As used herein, the term "amino" or "amine" interchangeably refers to a —NR2 group, wherein each R is, e.g., H or a substituent. In some embodiments, the amino group is further substituted to form an ammonium ion, e.g., NR3+. Ammonium moieties are specifically included in the definition of "amino" or "amine." Substituents can be, for example, an alkyl, alkoxy, cycloalkyl, heterocycloalkyl, amide, or carboxylate. An R group may be further substituted, for example, with one or more, e.g., one to four, groups selected from halo, cyano, alkenyl, alkynyl, alkyl, cycloalkyl, heterocycloalkyl, aryl, heteroaryl, urea, carbonyl, carboxylate, amine, and amide. An "amide" or "amido" group interchangeably refers to a group similar to an amine or amino group but further including a —C(O), e.g., —C(O) NR2. Some contemplated amino or amido groups (some with optional alkylene groups, e.g., alkylene-amino, or alkylene-amido) include —CH2NH2, —CH(CH3)NH2, —CH(CH3)2NH2, —CH2CH2NH2, —CH2CH2N(CH3)2, —CH2NHCH3, —C(O)NHCH3, —C(O)N(CH3)2, —CH2C(O)NHphenyl, —CH2NHC(O)CH3, —CH2NHCH2CH2OH, —CH2NHCH2CO2H, and —CH2NH(CH3)CH2CO2CH3.

Collectively, antibodies form a family of plasma proteins known as immunoglobulins and comprise of immunoglobulin domains. (Janeway et al., Immunobiology: The Immune System in Health and Disease, 4$^{th}$ ed., Elsevier Science Ltd./Garland Publishing, 1999. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", Immunobiology: The Immune System in Health and Disease, 4$^{th}$ ed. Elsevier Science Ltd./Garland Publishing, (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra).

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the present disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including any one of IgG1, IgG2, IgG3 or IgG4.

The antibody can be a monoclonal antibody or a polyclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In certain aspects, the antibody is a human antibody. In certain aspects, the antibody is a chimeric antibody or a humanized antibody. The term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also can contain domains of two or more different antibodies within the same species. The term "humanized" when used in relation to antibodies refers to antibodies having at least CDR regions from a non-human source which are engineered to have a structure and immunological function more similar to true human antibodies than the original source antibodies. For example, humanizing can involve grafting a CDR from a non-human antibody, such as a mouse antibody, into a human antibody. Humanizing also can involve select amino acid substitutions to make a non-human sequence more similar to a human sequence.

An antibody can be cleaved into fragments by enzymes, such as, e.g., papain and pepsin. Papain cleaves an antibody to produce two Fab fragments and a single Fc fragment. Pepsin cleaves an antibody to produce a F(ab')2 fragment and a pFc' fragment. As used herein, the term "antigen binding antibody fragment refers to a portion of an antibody molecule that is capable of binding to the antigen of the antibody and is also known as "antigen-binding fragment" or "antigen-binding portion". In exemplary instances, the antigen binding antibody fragment is a Fab fragment or a F(ab')2 fragment.

The architecture of antibodies has been exploited to create a growing range of alternative formats that span a molecular-weight range of at least about 12-150 kDa and has a valency (n) range from monomeric (n=1), to dimeric (n=2), to trimeric (n=3), to tetrameric (n=4), and potentially higher; such alternative formats are referred to herein as "antibody protein products". Antibody protein products include those based on the full antibody structure and those that mimic antibody fragments which retain full antigen-binding capacity, e.g., scFvs, Fabs and VHH/VH (discussed below). The smallest antigen binding antibody fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

As used herein, the term "aryl" refers to a C6-14 monocyclic or polycyclic aromatic group, preferably a C6-10 monocyclic or bicyclic aromatic group, or C10-14 polycyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to $C_{10-14}$ bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, —C1-8alkyl, —C2-8alkenyl, —C2-8alkynyl, —CF3, —OCF3, —NO2, —CN, —NC, —OH, alkoxy, amino, —CO2H, —CO2C1-C8alkyl, —OCOC1-C8alkyl, —C3-C10 cycloalkyl, —C3-C10 heterocycloalkyl, —C5-C10aryl, and —C5-C10 heteroaryl.

As used herein, the term "cycloalkyl" refers to a monocyclic or polycyclic non-aromatic carbocyclic ring, where the polycyclic ring can be fused, bridged, or spiro. The carbocyclic ring can have 3 to 10 carbon ring atoms. Contemplated carbocyclic rings include, but are not limited to, cyclopropyl, cyclobutyl, cyclopentyl, cyclohexyl, cycloheptyl, cyclooctyl, and cyclononyl.

As used herein, the term "heterocycloalkyl" means a monocyclic or polycyclic (e.g., bicyclic), saturated or partially unsaturated, ring system containing 3 or more (e.g., 3 to 12, 4 to 10, 4 to 8, or 5 to 7) total atoms, of which one to five (e.g., 1, 2, 3, 4, or 5) of the atoms are independently selected from nitrogen, oxygen, and sulfur. Nonlimiting examples of heterocycloalkyl groups include azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, and diazacycloheptyl.

Unless otherwise indicated, a cycloalkyl or heterocycloalkyl group can be unsubstituted or substituted with one or more, and in particular one to four, groups. Some contemplated substituents include halo, —$C_{1-8}$alkyl, —$C_{2-8}$alkenyl, —$C_{2-8}$alkynyl, —$OCF_3$, —$NO_2$, —CN, —NC, —OH, alkoxy, amino, —$CO_2H$, —$CO_2C_1$-$C_8$alkyl, —$OCOC_1$-$C_8$alkyl, —$C_3$-$C_{10}$ cycloalkyl, —$C_3$-$C_{10}$ heterocycloalkyl, —$C_8$-$C_{10}$aryl, and —$C_5$-$C_{10}$ heteroaryl.

As used herein, the term "heteroaryl" refers to a monocyclic or polycyclic ring system (for example, bicyclic) containing one to three aromatic rings and containing one to four (e.g., 1, 2, 3, or 4) heteroatoms selected from nitrogen, oxygen, and sulfur in an aromatic ring. In certain embodiments, the heteroaryl group has from 5 to 20, from 5 to 15, from 5 to 10 ring, or from 5 to 7 atoms. Heteroaryl also refers to C10-14 bicyclic and tricyclic rings, where one ring is aromatic and the others are saturated, partially unsaturated, or aromatic. Examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four or one or two, substituents. Contemplated substituents include halo, —$C_{1-8}$alkyl, —$C_{2-8}$alkenyl, —$C_{2-8}$alkynyl, —$OCF_3$, —$NO_2$, —CN, —NC, —OH, alkoxy, amino, —$CO_2H$, —$CO_2C_1$-$C_8$alkyl, —$OCOC_1$-$C_8$alkyl, —$C_3$-$C_{10}$ cycloalkyl, —$C_3$-$C_{10}$ heterocycloalkyl, —$C_8$-$C_{10}$aryl, and —$C_5$-$C_{10}$ heteroaryl.

As used herein, the term Boc refers to the structure

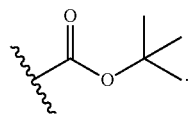 [SMILES: *C(=O)OC(C)(C)C]

As used herein, the term Cbz refers to the structure

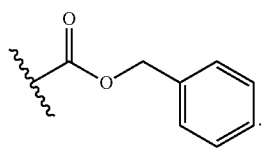 [SMILES: *C(=O)OCc1ccccc1]

Compounds of the Disclosure

Provided herein are KRAS inhibitors having structures of one of Formulas I, Ia, II, and IIa, discussed in more detail below.

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as 2H, 3H, 11C, 13C, 14C, 13N, 15N, 15O, 17O, 18O, 31P, 32P, 35S, 18F, 36Cl, 123I, and 125I, respectively. These radiolabelled compounds could be useful to help determine or measure the effectiveness of the compounds, by characterizing, for example, the site or mode of action, or binding affinity to pharmacologically important site of action. Certain isotopically-labeled compounds of the disclosure, for example, those incorporating a radioactive isotope, are useful in drug and/or substrate tissue distribution studies. The radioactive isotopes tritium, i.e. 3H, and carbon-14, i.e. 14C, are particularly useful for this purpose in view of their ease of incorporation and ready means of detection.

Substitution with heavier isotopes such as deuterium, i.e. 2H, may afford certain therapeutic advantages resulting from greater metabolic stability, for example, increased in vivo half-life or reduced dosage requirements, and hence are preferred in some circumstances.

Substitution with positron emitting isotopes, such as 11C, 18F, 15O and 13N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. The separation and isolation of the isomeric species is duly designated by the well known and accepted symbols "M" or "P".

In another embodiment, these compounds can be used as intermediates in the process of making compounds in the present application.

In another embodiment, these compounds can be in the form of a pharmaceutically acceptable salt and in a pharmaceutical formulation with a pharmaceutically acceptable excipient.

Specifically contemplated compounds include those as listed in Table 1:

TABLE 1

| Ex. # | Structure |
|---|---|
| 1 | (structure) |
| 2 | (structure) |
| 3 | (structure) |
| 4 | (structure) |
| 5 | (structure) |
| 6 | (structure) |

TABLE 1-continued

| Ex. # | Structure |
|---|---|
| 7 | (structure) |
| 8 | (structure) |
| 9 | (structure) |
| 10 | (structure) |
| 11 | (structure) |
| 12 | (structure) |

TABLE 1-continued
| Ex. # | Structure |
|---|---|
| 13 | 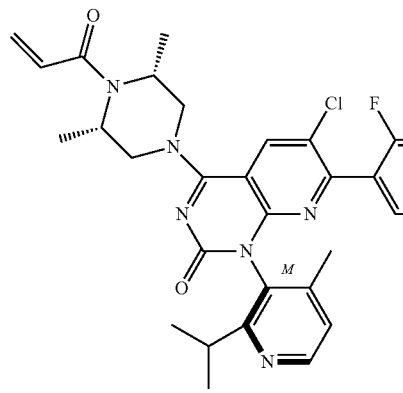 |
| 14 | 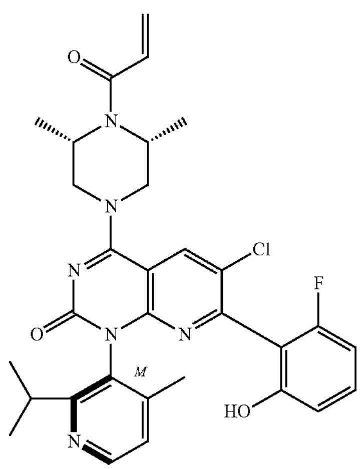 |
| 15 | 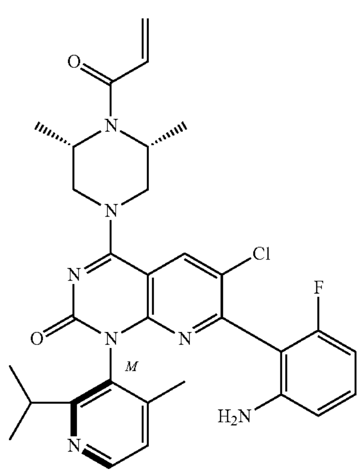 |
TABLE 1-continued
| Ex. # | Structure |
|---|---|
| 16 | 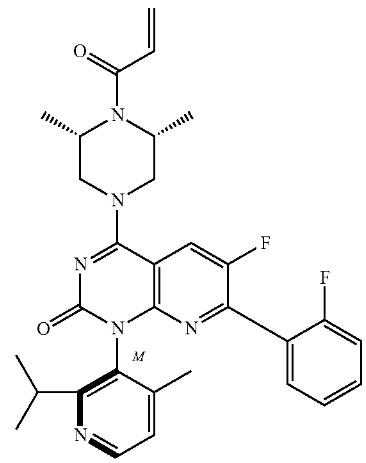 |
| 17 | 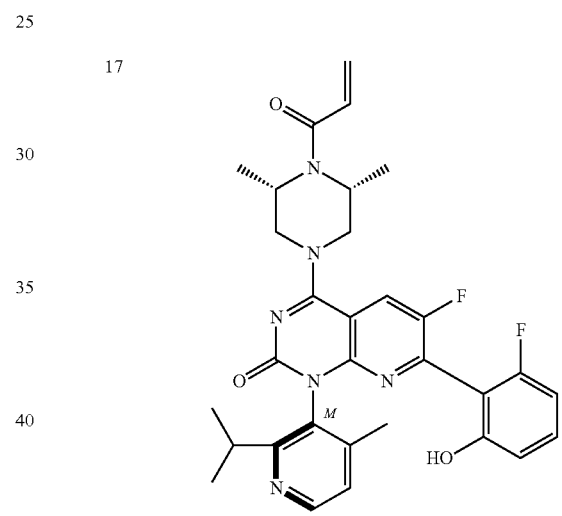 |
| 18 | 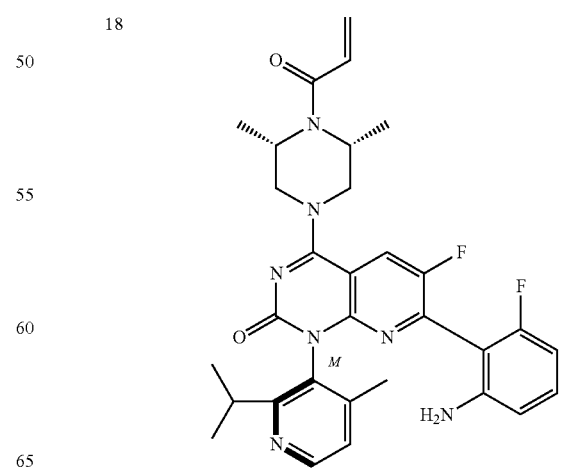 |

TABLE 1-continued

| Ex. # | Structure |
|---|---|
| 19 | 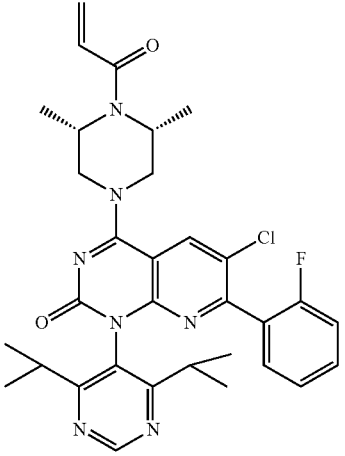 |
| 20 | 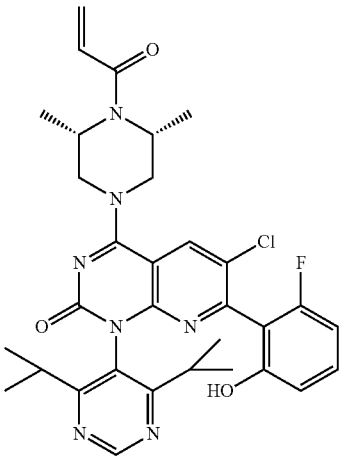 |
| 21 | 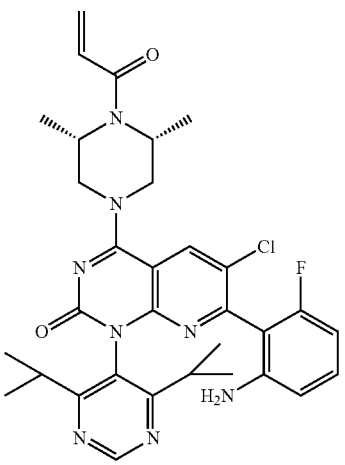 [SMILES: C=CC(=O)N1[C@H](C)CN(c2nc(=O)n(-c3c(C(C)C)ncnc3C(C)C)c3nc(-c4c(N)cccc4F)c(Cl)cc23)C[C@@H]1C] |
| 22 | 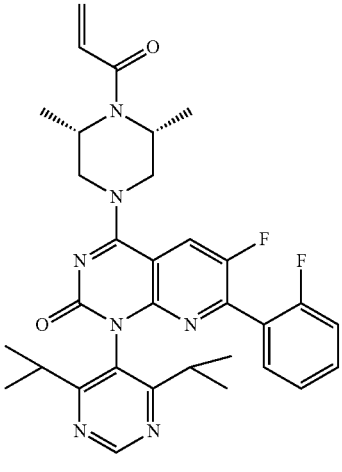 [SMILES: C=CC(=O)N1[C@H](C)CN(c2nc(=O)n(-c3c(C(C)C)ncnc3C(C)C)c3nc(-c4ccccc4F)c(F)cc23)C[C@@H]1C] |
| 23 | 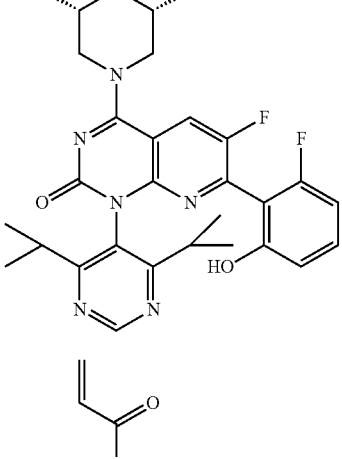 |
| 24 | 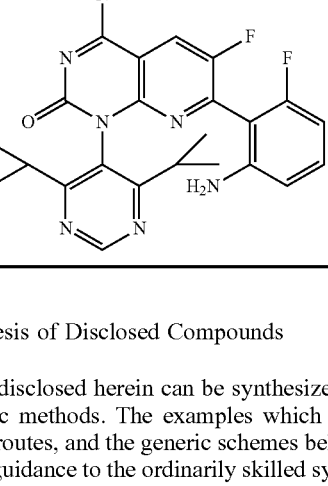 |

Synthesis of Disclosed Compounds

Compounds as disclosed herein can be synthesized via a number of specific methods. The examples which outline specific synthetic routes, and the generic schemes below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

Appropriate protecting groups and deprotection reagents are known to those skilled in the art, e.g., as discussed in Greene's Protective Groups in Organic Synthesis.

Contemplated halogenating agents include, but are not limited to, chlorine, bromine, N-chlorosuccinimide, and N-bromosuccinimide, optionally in the presence of a catalyst, e.g., iron or aluminum. The ordinarily skilled synthetic chemist will readily understand that other halogenating agents and catalysts can be used.

Contemplated amidating agents include, but are not limited to, N, N'-diisopropylcarbodiimide, N-(3-dimethylaminopropyl)-N'-ethylcarbodiimide, benzotriazol-1-yl-oxytripyrrolidinophosphonium hexafluorophosphate, O-(benzotriazol-1-yl)-N,N,N',N'-tetramethyluronium hexafluorophosphate, thionyl chloride, isobutyl chloroformate, diethyl cyanophosphonate, carbonyl diimidazole, and polyphosphonic anhydride. The ordinarily skilled synthetic chemist will readily understand that other amidating agents can be used.

Contemplated sulfurizing agents include, but are not limited to, sulfur, phosphorus pentasulfide, and Lawesson's reagent. The ordinarily skilled synthetic chemist will readily understand that other sulfurizing agents can be used.

Contemplated oxidants include, but are not limited to, hydrogen peroxide, iodobenzene diacetate, t-butyl hydroperoxide, N-bromosuccinimide, and ammonium peroxodisulfate. The ordinarily skilled synthetic chemist will readily understand that other oxidants can be used.

Contemplated activating agents include, but are not limited to, sodium nitrite and t-butyl nitrite. The ordinarily skilled synthetic chemist will readily understand that other activating agents can be used.

Contemplated cross-coupling reactions include, but are not limited to, Suzuki coupling, Negishi coupling, Hiyama coupling, Kumada coupling, and Stille coupling.

Pharmaceutical Compositions, Dosing, and Routes of Administration

Also provided herein are pharmaceutical compositions that includes a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable e" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or it may be divided into multiple doses.

Methods of Using KRAS G12C Inhibitors

The present disclosure provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by G12C KRAS, HRAS or NRAS mutation (e.g., cancer).

In some embodiments, a method for treatment of cancer is provided, the method comprising administering an effective amount of any of the foregoing pharmaceutical compositions comprising a compound as disclosed herein to a subject in need thereof. In some embodiments, the cancer is mediated by a KRAS, HRAS or NRAS G12C mutation. In various embodiments, the cancer is pancreatic cancer, colorectal cancer or lung cancer. In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound as disclosed herein or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount a compound disclosed herein.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound as disclosed herein, or a pharmaceutically acceptable salt thereof. In some embodiments, said method relates to the treatment of a subject who suffers from a cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C Mutant KRAS, HRAS or NRAS protein activity by contacting the protein with an effective amount of a compound of the disclosure. Modulation can be inhibiting or activating protein activity. In some embodiments, the disclosure provides methods of inhibiting protein activity by contacting the G12C Mutant KRAS, HRAS or NRAS protein with an effective amount of a compound of the disclosure in solution. In some embodiments, the disclosure provides methods of inhibiting the G12C Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of a compound of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS, HRAS or NRAS G12C activity in a cell by contacting said cell with an amount of a compound of the disclosure sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of a compound of the disclosure sufficient to inhibit the activity of KRAS, HRAS or NRAS G12C in said tissue. In some embodiments, the disclosure provides methods of inhibiting KRAS, HRAS or NRAS G12C activity in an organism by contacting said organism with an amount of a compound of the disclosure sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of a compound of the disclosure sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of a compound of the disclosure sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of a compound of the disclosure sufficient to inhibit the activity of KRAS, HRAS or NRAS G12C in said human. The present disclosure provides methods of treating a disease mediated by KRAS, HRAS or NRAS G12C activity in a subject in need of such treatment.

Combination Therapy:

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXANTM™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex$^T$n), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, 1-131, 1-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as 1-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or 1-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675, European Patent Publication EP1786785, European Patent Publication No. EP1181017, United States Publication No. US20090012085, United States Publication U.S. Pat. No. 5,863,949, United States Publication U.S. Pat. No. 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, andMMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflomithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-$C_{225}$), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as *vinca* alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNTO328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zamestra™), anti-CD138 (e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), and BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds of the present invention may also be used in combination with an additional pharmaceutically active compound that disrupts or inhibits RAS-RAF-ERK or PI3K-AKT-TOR signaling pathways. In other such combinations, the additional pharmaceutically active compound is a PD-1 and PD-L1 antagonist. The compounds or pharmaceutical compositions of the disclosure can also be used in combination with an amount of one or more substances selected from EGFR inhibitors, MEK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., *Pharmacogenetics and Pharmacogenomics In Oncology Therapeutic Antibody Development*, BioTechniques 2005; 39(4): 565-8, and Paez J G, et. al., *EGFR Mutations In Lung Cancer Correlation With Clinical Response To Gefitinib Therapy*, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12): 1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydroimidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d] pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) *Biochem. J.,* 385 (Pt. 2), 399-408); Akt-1-1,2 (inhibits Ak1 and 2) (Barnett et al. (2005) *Biochem. J* 385 (Pt. 2), 399-408); API-59CJ-Ome (e.g., Jin et al. (2004) *Br. J. Cancer* 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) *J Nutr.* 134(12 Suppl), 3493S-3498S); perifosine (e.g., interferes with Akt membrane localization; Dasmahapatra et al. (2004) *Clin. Cancer Res.* 10(15), 5242-52, 2004); phosphatidylinositol ether lipid analogues (e.g., Gills and Dennis (2004) *Expert. Opin.*

*Investig. Drugs* 13, 787-97); and triciribine (TCN or API-2 or NCI identifier: NSC 154020; Yang et al. (2004) *Cancer Res.* 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

MCI-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

SHP inhibitors include, but are not limited to, SHP099.

Proteasome inhibitors include, but are not limited to, Kyprolis® (carfilzomib), Velcade® (bortezomib), and oprozomib.

Immune therapies include, but are not limited to, anti-PD-1 agents, anti-PDL-1 agents, anti-CTLA-4 agents, anti-LAG1 agents, and anti-OX40 agents.

Monoclonal antibodies include, but are not limited to, Darzalex® (daratumumab), Herceptin® (trastuzumab), Avastin® (bevacizumab), Rituxan® (rituximab), Lucentis® (ranibizumab), and Eylea® (aflibercept).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., *Blood* 110(1):186-192 (2007), Thompson et al., *Clin. Cancer Res.* 13(6):1757-1761 (2007), and Korman et al., International Application No. PCT/JP2006/309606 (publication no. WO 2006/121168 A1), each of which are expressly incorporated by reference herein. include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

In a particular embodiment, the compounds of the present invention are used in combination with an anti-PD-1 antibody. In a specific embodiment, the anti-PD-1 antibody (or antigen binding antibody fragment thereof) comprises 1, 2, 3, 4, 5, or all 6 the CDR amino acid sequences of SEQ ID NOs: 1-6 (representing HC CDR1, HC CDR2, HC CDR3, LC CDR1, LC CDR2, and LC CDR3, in that order). In specific embodiments, the anti-PD-1 antibody (or antigen binding antibody fragment thereof) comprises all 6 of the CDR amino acid sequences of SEQ ID NOs: 1-6. In other embodiments, the anti-PD-1 antibody (or antigen binding antibody fragment thereof) comprises (a) the heavy chain variable region amino acid sequence in SEQ ID NO: 7, or a variant sequence thereof which differs by only one or two amino acids or which has at least or about 70% sequence identity, or (b) the light chain variable region amino acid sequence in SEQ ID NO: 8 or a variant sequence thereof which differs by only one or two amino acids or which has at least or about 70% sequence identity. In an exemplary embodiment, the anti-PD-1 antibody (or antigen binding antibody fragment thereof) comprises the heavy chain variable region amino acid sequence in SEQ ID NO: 7 and the light chain variable region amino acid sequence in SEQ ID NO: 8. In other embodiments, the anti-PD-1 antibody (or antigen binding antibody fragment thereof) comprises (a) the heavy chain amino acid sequence of SEQ ID NO: 9 or a variant sequence thereof which differs by only one or two amino acids or which has at least or about 70% sequence identity; or (b) the light chain amino acid sequence of SEQ ID NO: 10 or a variant sequence thereof which differs by only one or two amino acids or which has at least or about 70% sequence identity. In an exemplary embodiment, the anti-PD-1 antibody (or antigen binding antibody fragment thereof) comprises the heavy chain amino acid sequence of SEQ ID NO: 9 and the light chain amino acid sequence of SEQ ID NO: 10.

The present disclosure further provides nucleic acid sequences encoding the anti-PD-1 antibody (or an antigen binding portion thereof). In exemplary aspects, the antibody comprises 1, 2, 3, 4, 5, or all 6 CDRs encoded by the nucleic acid(s) of SEQ ID NOs: 11-16 (representing HC CDR1, HC CDR2, HC CDR3, LC CDR1, LC CDR2, and LC CDR3, in that order). In another exemplary aspect, the antibody comprises all 6 CDRs encoded by the nucleic acids of SEQ ID NOs: 11-16. In some embodiments, the anti-PD-1 antibody (or an antigen binding portion thereof) comprises (a) a heavy chain variable region encoded by SEQ ID NO: 17 or a variant sequence thereof which differs by only 1, 2, 3, 4, 5, or 6 nucleic acids or which has at least or about 70%, 85%, 90%, or 95% sequence identity, or (b) a light chain variable region encoded by SEQ ID NO: 18 or a variant sequence thereof which differs by only 1, 2, 3, 4, 5, or 6 nucleic acids or which has at least or about 70%, 85%, 90%, or 95% sequence identity. In an exemplary embodiment, the anti-PD-1 antibody (or an antigen binding portion thereof) comprises a heavy chain variable region encoded by SEQ ID NO: 17 and a light chain variable region encoded by SEQ ID NO: 18. In other embodiments, the anti-PD-1 antibody (or an antigen binding portion thereof) comprises (a) a heavy chain encoded by SEQ ID NO: 19 or a variant sequence thereof which differs by only 1, 2, 3, 4, 5, or 6 nucleic acids or which has at least or about 70%, 85%, 90%, or 95% sequence identity, or (b) a light chain encoded by SEQ ID NO: 20 or a variant sequence thereof which differs by only 1, 2, 3, 4, 5, or 6 nucleic acids or which has at least or about 70%, 85%, 90%, or 95% sequence identity. In an exemplary embodiment, the anti-PD-1 antibody (or an antigen binding portion thereof) comprises a heavy chain encoded by SEQ ID NO: 19 and a light chain encoded by SEQ ID NO: 20.

| SEQ ID NO. | Sequence Type | Sequence |
|---|---|---|
| 1 | PRT | Ser Tyr Asp Met Ser |
| 2 | PRT | Leu Ile Ser Gly Gly Gly Ser Gln Thr Tyr Tyr Ala Glu Ser Val Lys |
| 3 | PRT | Pro Ser Gly His Tyr Phe Tyr Ala Met Asp Val |
| 4 | PRT | Arg Ala Ser Gln Gly Ile Ser Asn Trp Leu Ala |
| 5 | PRT | Ala Ala Ser Ser Leu Gln Ser |
| 6 | PRT | Gln Gln Ala Glu Ser Phe Pro His Thr |
| 7 | PRT | Glu Val Gln Leu Leu Glu Ser Gly Gly Gly Leu Val Gln Pro Gly Gly<br>Ser Leu Arg Leu Ser Cys Ala Ala Ser Gly Phe Thr Phe Ser Ser Tyr<br>Asp Met Ser Trp Val Arg Gln Ala Pro Gly Lys Gly Leu Glu Trp Val<br>Ser Leu Ile Ser Gly Gly Gly Ser Gln Thr Tyr Tyr Ala Glu Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Phe Cys Ala<br>Ser Pro Ser Gly His Tyr Phe Tyr Ala Met Asp Val Trp Gly Gln Gly<br>Thr Thr Val Thr Val Ser Ser |
| 8 | PRT | Asp Ile Gln Met Thr Gln Ser Pro Ser Ser Val Ser Ala Ser Val Gly Asp<br>Arg Val Thr Ile Thr Cys Arg Ala Ser Gln Gly Ile Ser Asn Trp Leu Ala<br>Trp Tyr Gln Gln Lys Pro Gly Lys Ala Pro Lys Leu Leu Ile Phe Ala<br>Ala Ser Ser Leu Gln Ser Gly Val Pro Ser Arg Phe Ser Gly Ser Gly Ser<br>Gly Thr Asp Phe Thr Leu Thr Ile Ser Ser Leu Gln Pro Glu Asp Phe<br>Ala Thr Tyr Tyr Cys Gln Gln Ala Glu Ser Phe Pro His Thr Phe Gly<br>Gly Gly Thr Lys Val Glu Ile Lys |
| 9 | PRT | Met Asp Met Arg Val Pro Ala Gln Leu Leu Gly Leu Leu Leu Leu Trp<br>Leu Arg Gly Ala Arg Cys Glu Val Gln Leu Leu Glu Ser Gly Gly Gly<br>Leu Val Gln Pro Gly Gly Ser Leu Arg Leu Ser Cys Ala Ala Ser Gly<br>Phe Thr Phe Ser Ser Tyr Asp Met Ser Trp Val Arg Gln Ala Pro Gly<br>Lys Gly Leu Glu Trp Val Ser Leu Ile Ser Gly Gly Gly Ser Gln Thr<br>Tyr Tyr Ala Glu Ser Val Lys Gly Arg Phe Thr Ile Ser Arg Asp Asn<br>Ser Lys Asn Thr Leu Tyr Leu Gln Met Asn Ser Leu Arg Ala Glu Asp<br>Thr Ala Val Tyr Phe Cys Ala Ser Pro Ser Gly His Tyr Phe Tyr Ala<br>Met Asp Val Trp Gly Gln Gly Thr Thr Val Thr Val Ser Ser Ala Ser<br>Thr Lys Gly Pro Ser Val Phe Pro Leu Ala Pro Ser Ser Lys Ser Thr Ser<br>Gly Gly Thr Ala Ala Leu Gly Cys Leu Val Lys Asp Tyr Phe Pro Glu<br>Pro Val Thr Val Ser Trp Asn Ser Gly Ala Leu Thr Ser Gly Val His<br>Thr Phe Pro Ala Val Leu Gln Ser Ser Gly Leu Tyr Ser Leu Ser Ser<br>Val Val Thr Val Pro Ser Ser Ser Leu Gly Thr Gln Thr Tyr Ile Cys Asn<br>Val Asn His Lys Pro Ser Asn Thr Lys Val Asp Lys Lys Val Glu Pro<br>Lys Ser Cys Asp Lys Thr His Thr Cys Pro Pro Cys Pro Ala Pro Glu<br>Leu Leu Gly Gly Pro Ser Val Phe Leu Phe Pro Pro Lys Pro Lys Asp<br>Thr Leu Met Ile Ser Arg Thr Pro Glu Val Thr Cys Val Val Val Asp<br>Val Ser His Glu Asp Pro Glu Val Lys Phe Asn Trp Tyr Val Asp Gly<br>Val Glu Val His Asn Ala Lys Thr Lys Pro Cys Glu Glu Gln Tyr Gly<br>Ser Thr Tyr Arg Cys Val Ser Val Leu Thr Val Leu His Gln Asp Trp<br>Leu Asn Gly Lys Glu Tyr Lys Cys Lys Val Ser Asn Lys Ala Leu Pro<br>Ala Pro Ile Glu Lys Thr Ile Ser Lys Ala Lys Gly Gln Pro Arg Glu Pro<br>Gln Val Tyr Thr Leu Pro Pro Ser Arg Glu Glu Met Thr Lys Asn Gln<br>Val Ser Leu Thr Cys Leu Val Lys Gly Phe Tyr Pro Ser Asp Ile Ala<br>Val Glu Trp Glu Ser Asn Gly Gln Pro Glu Asn Asn Tyr Lys Thr Thr<br>Pro Pro Val Leu Asp Ser Asp Gly Ser Phe Phe Leu Tyr Ser Lys Leu<br>Thr Val Asp Lys Ser Arg Trp Gln Gln Gly Asn Val Phe Ser Cys Ser<br>Val Met His Glu Ala Leu His Asn His Tyr Thr Gln Lys Ser Leu Ser<br>Leu Ser Pro Gly Lys |
| 10 | PRT | Met Asp Met Arg Val Pro Ala Gln Leu Leu Gly Leu Leu Leu Leu Trp<br>Leu Arg Gly Ala Arg Cys Asp Ile Gln Met Thr Gln Ser Pro Ser Ser<br>Val Ser Ala Ser Val Gly Asp Arg Val Thr Ile Thr Cys Arg Ala Ser<br>Gln Gly Ile Ser Asn Trp Leu Ala Trp Tyr Gln Gln Lys Pro Gly Lys<br>Ala Pro Lys Leu Leu Ile Phe Ala Ala Ser Ser Leu Gln Ser Gly Val Pro<br>Ser Arg Phe Ser Gly Ser Gly Ser Gly Thr Asp Phe Thr Leu Thr Ile Ser<br>Ser Leu Gln Pro Glu Asp Phe Ala Thr Tyr Tyr Cys Gln Gln Ala Glu<br>Ser Phe Pro His Thr Phe Gly Gly Gly Thr Lys Val Glu Ile Lys Arg<br>Thr Val Ala Ala Pro Ser Val Phe Ile Phe Pro Pro Ser Asp Glu Gln Leu<br>Lys Ser Gly Thr Ala Ser Val Val Cys Leu Leu Asn Asn Phe Tyr Pro<br>Arg Glu Ala Lys Val Gln Trp Lys Val Asp Asn Ala Leu Gln Ser Gly<br>Asn Ser Gln Glu Ser Val Thr Glu Gln Asp Ser Lys Asp Ser Thr Tyr<br>Ser Leu Ser Ser Thr Leu Thr Leu Ser Lys Ala Asp Tyr Glu Lys His<br>Lys Val Tyr Ala Cys Glu Val Thr His Gln Gly Leu Ser Ser Pro Val<br>Thr Lys Ser Phe Asn Arg Gly Glu Cys |

| SEQ ID<br>NO. | Sequence<br>Type | Sequence |
|---|---|---|
| 11 | DNA | agctatgaca tgagc |
| 12 | DNA | cttattagtg gtggtggtag tcaaacatac tacgcagaat ccgtgaaggg c |
| 13 | DNA | cccagtggcc actacttcta cgctatggac gtc |
| 14 | DNA | cgggcgagtc agggtattag caactggtta gcc |
| 15 | DNA | gctgcatcca gtttgcaaag t |
| 16 | DNA | caacaggctg aaagtaccc tcacact |
| 17 | DNA | gaggtgcagc tgttggagtc tgggggaggc ttggtacagc ctggggggtc cctgagactc<br>tcctgtgcag cctctggatt cacctttagc agctatgaca tgagctgggt ccgccaggct<br>ccagggaagg ggctgaatg gtctcactt attagtggtg gtggtagtca aacatactac<br>gcagaatccg tgaagggccg gttcaccatc tccagagaca attccaagaa cacgctgtat<br>ctgcaaatga acagcctgag agccgaggac acggccgtat atttctgtgc gtccccagt<br>ggccactact tctacgctat ggacgtctgg ggccaaggga ccacggtcac cgtctcctca |
| 18 | DNA | gacatccaga tgacccagtc tccatcttcc gtgtctgcat ctgttggaga cagagtcacc<br>atcacttgtc gggcgagtca gggtattagc aactggttag cctggtatca gcagaaacca<br>gggaaagccc ctaagctcct gatctttgct gcatccagtt tgcaaagtgg ggtcccatca<br>aggttcagcg gcagtggatc tgggacagat ttcaccctca ccatcagcag cctgcagcct<br>gaagattttg caacttacta ttgtcaacag gctgaaagtt ccctcacac tttcggcgga<br>gggaccaagg tggagatcaa a |
| 19 | DNA | atggacatga gggtgcccgc tcagctcctg gggctcctgc tgctgtggct gagaggtgcg<br>cgctgtgagg tgcagctgtt ggagtctggg ggaggcttgg tacagcctgg ggggtccctg<br>agactctcct gtgcagcctc tggattcacc tttagcagct atgacatgag ctgggtccgc<br>caggctccag ggaaggggct ggaatgggtc tcacttatta gtggtggtgg tagtcaaaca<br>tactacgcag aatccgtgaa gggccggttc accatctcca gagacaattc caagaacacg<br>ctgtatctgc aaatgaacag cctgagagcc gaggacacgg ccgtatattt ctgtgcgtcc<br>cccagtggcc actacttcta cgctatggac gtctggggcc aagggaccac ggtcaccgtc<br>tcctcagcct ccaccaaggg cccatcggtc ttccccctgg cacctcctc caagagcacc<br>tctgggggca gcggccct gggctgcctg gtcaaggact acttccccga accggtgacg<br>gtgtcgtgga actcaggcgc cctgaccagc ggcgtgcaca ccttcccggc tgtcctacag<br>tcctcaggac tctactccct cagcagcgtg gtgaccgtgc cctccagcag cttgggcacc<br>cagacctaca tctgcaacgt gaatcacaag cccagcaaca ccaaggtgga caagaaagtt<br>gagcccaaat cttgtgacaa aactcacaca tgcccaccgt gcccagcacc tgaactcctg<br>ggggaccgt cagtcttcct cttccccca aaacccaagg acaccctcat gatctcccgg<br>acccctgagg tcacatgcgt ggtggtggac gtgagccacg aagaccctga ggtcaagttc<br>aactggtacg tggacggcgt ggaggtgcat aatgccaaga caaagccgtg cgaggagcag<br>tacgcagca cgtaccgttg cgtcagcgtc ctcaccgtcc tgcaccagga ctggctgaat<br>ggcaaggagt acaagtgcaa ggtgtccaac aaagccctcc cagcccccat cgagaaaacc<br>atctccaaag ccaaagggca gccccgagaa ccacaggtgt acaccctgcc cccatcccgg<br>gaggagatga ccaagaacca ggtcagcctg acctgcctgg tcaaaggctt ctatcccagc<br>gacatcgccg tggagtggga gagcaatggg cagccggaga acaactacaa gaccacgcct<br>cccgtgctgg actccgacgg ctccttcttc ctctatagca agctcaccgt ggacaagagc<br>aggtggcagc aggggaacgt cttctcatgc tccgtgatgc atgaggctct gcacaaccac<br>tacacgcaga agagcctctc cctgtctccg ggtaaa |
| 20 | DNA | atggacatga gggtgcccgc tcagctcctg gggctcctgc tgctgtggct gagaggtgcg<br>cgctgtgaca tccagatgac ccagtctcca tcttccgtgt ctgcatctgt tggagacaga<br>gtcaccatca cttgtcgggc gagtcagggt attagcaact ggttagcctg gtatcagcag<br>aaaccaggga agcccctaa gctcctgatc tttgctgcat ccagtttgca aagtggggtc<br>ccatcaaggt tcagcggcag tggatctggg acagatttca ccctcaccat cagcagcctg<br>cagcctgaag attttgcaac ttactattgt caacaggctg aaagtttccc tcacactttc<br>ggcggaggga ccaaggtgga gatcaaacga acggtggctg caccatctgt cttcatcttc<br>ccgccatctg atgagcagtt gaaatctgga actgcctctg ttgtgtgcct gctgaataac<br>ttctatccca gagaggccaa agtacagtgg aaggtggata acgccctcca atcgggtaac<br>tcccaggaga gtgtcacaga gcaggacagc aaggacagca cctacagcct cagcagcacc<br>ctgacgctga gcaaagcaga ctacgagaaa cacaaagtct acgcctgcga agtcacccat<br>cagggcctga gctcgcccgt cacaaagagc ttcaacaggg gagagtgt |

GITR agonists include, but are not limited to, GITR fusion proteins and anti-GITR antibodies (e.g., bivalent anti-GITR antibodies), such as, a GITR fusion protein described in U.S. Pat. No. 6,111,090 box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

EXAMPLES

Absolute configuration of Examples 1 4-((2S,5R,M)-4-acryloyl-2,5-dimethylpiperazin-1-yl)-6-chloro-7-(2-fluorophenyl)-1-(2-isopropyl-4-methylpyridin-3-yl)pyrido[2,3-d]pyrimidin-2(1H)-one, 5 4-((2S,5R,M)-4-acryloyl-2,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one, 6 4-((2S,5R,M)-4-acryloyl-2,5-dimethylpiperazin-1-yl)-7-(2-amino-6-fluorophenyl)-6-fluoro-1-(2-isopropyl-4-methylpyridin-3-yl)pyrido[2,3-d]pyrimidin-2(1H)-one and 13 (M)-4-(4-acryloyl-cis-3,5-dimethylpiperazin-1-yl)-6-chloro-7-(2-fluorophenyl)-1-(2-isopropyl-4-methylpyridin-3-yl)pyrido[2,3-d]pyrimidin-2(1H)-one was assigned based on cocrystallization. Absolute configuration of intermediates C and G was assigned based on cocrystallization of molecules prepared from these intermediates such as Examples 1, 5, 6 and 13.

Example 1

4-((2S,5R,M)-4-Acryloyl-2,5-dimethylpiperazin-1-yl)-6-chloro-7-(2-fluorophenyl)-1-(2-isopropyl-4-methylpyridin-3-yl)pyrido[2,3-d]pyrimidin-2(1H)-one

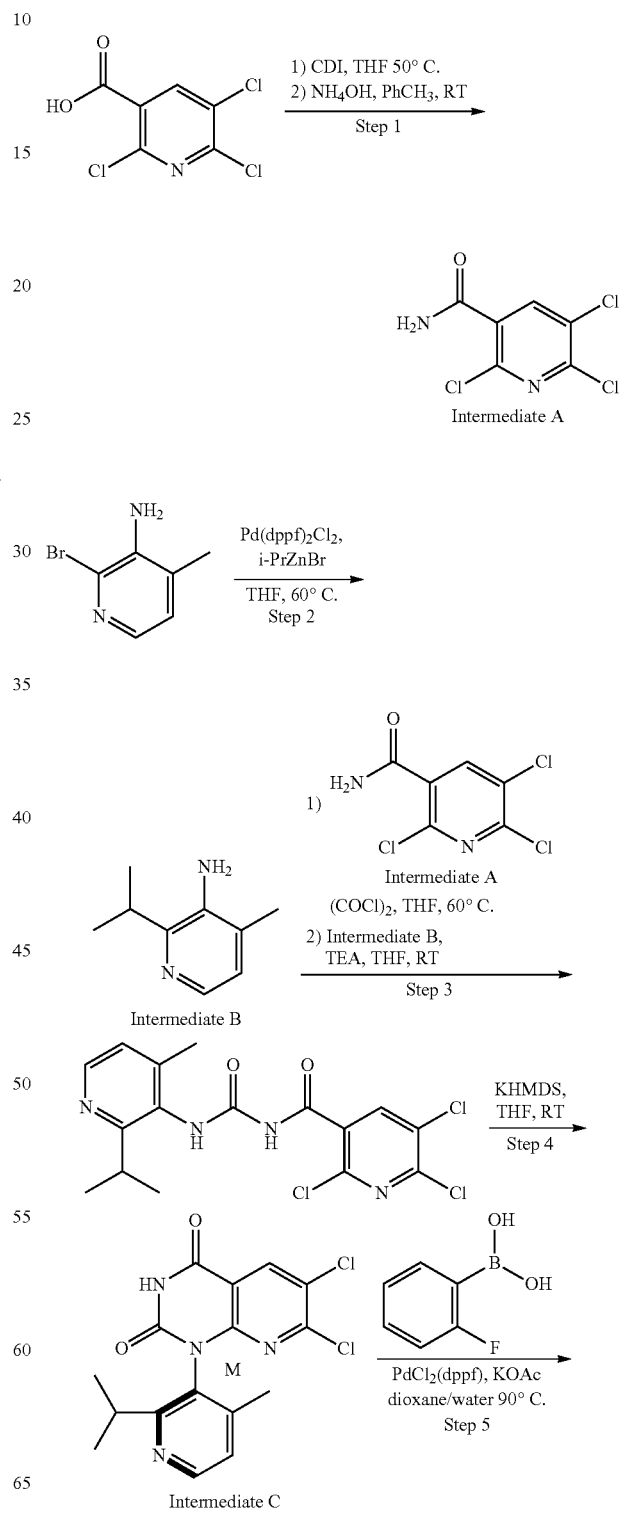

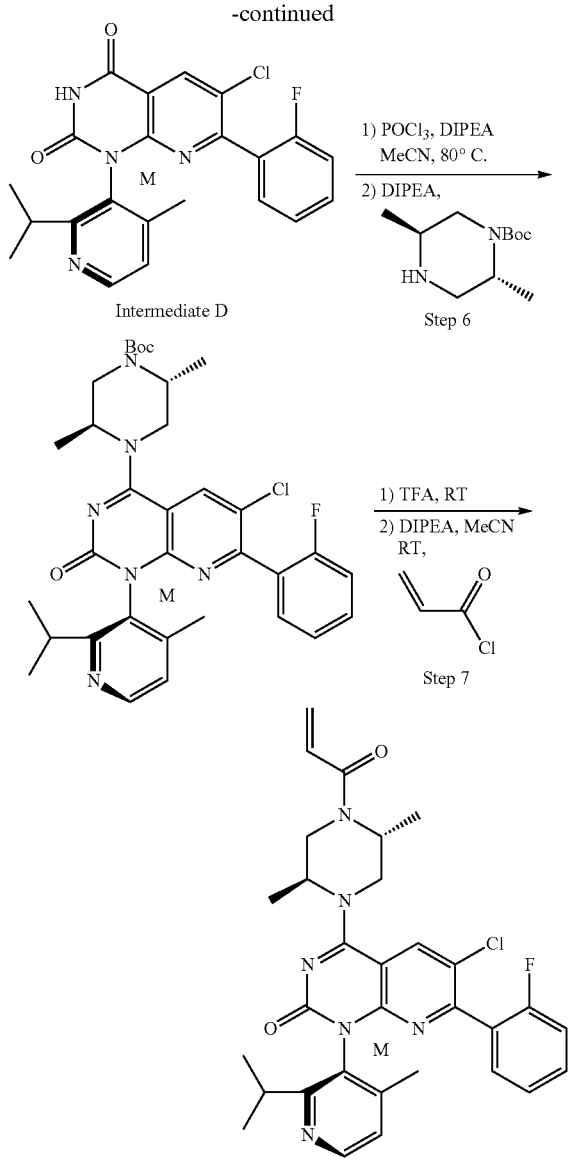

Step 1: 2,5,6-Trichloronicotinamide (Intermediate A)

1,1'-Carbonyldiimidazole (40 g, 247 mmol) was added in portions to 2,5,6-trichloronicotinic acid (50.7 g, 224 mmol, Combi-Blocks, San Diego, Calif.) in THF (400 mL), allowing gas evolution to cease between addition. The resulting mixture was stirred for 5 min and then was degassed with house vacuum and flushed with nitrogen. The resulting mixture was heated to 50° C. for 60 min, then diluted with toluene (100 mL) and concentrated to half the initial volume. The resulting mixture was cooled to 0° C. and ammonium hydroxide (60 mL, 437 mmol) was added slowly via syringe. The reaction was stirred for 10 min at rt, diluted with EtOAc (200 mL) and washed with water (3×100 mL). The organic layer was dried over anhydrous $Na_2SO_4$ and concentrated in vacuo. The residue was suspended in 9:1 heptane/EtOAc (300 mL) and filtered. The filtered solids were collected and the remaining mother liquor was partially evaporated to half the initial volume, cooled to 0° C., and filtered. The two crops of filtered solids were combined to provide 2,5,6-trichloronicotinamide.

Step 2: 2-Isopropyl-4-methylpyridin-3-amine (Intermediate B)

To a slurry of 3-amino-2-bromo-4-picoline (360 mg, 1.9 mmol, Combi-Blocks, San Diego, Calif.) in THF (4 mL) was added [1,1'-bis(diphenylphosphino)ferrocene]dichloropalladium(II) complex (Sigma-Aldrich, St. Loius, Mo.) with DCM (79 mg, 0.10 mmol). The resulting slurry was degassed with argon for 2 min and then 2-propylzinc bromide (0.5 M solution in THF, 5.40 mL, 2.7 mmol, Sigma-Aldrich, St. Louis, Mo.) was added. The resulting solution was heated at 60° C. for 17 h, then the heating was stopped and the reaction was allowed to cool to rt. The reaction mixture was quenched with water (10 mL) and 1 N NaOH solution (20 mL) and then was extracted with EtOAc. The combined organic layers were dried over anhydrous $Na_2SO_4$ and concentrated in vacuo. The residue was purified by silica gel chromatography (eluent: 0-15% MeOH/DCM) to provide 2-isopropyl-4-methylpyridin-3-amine. $^1$H NMR (400 MHz, DMSO-$d_6$) δ ppm 7.66 (d, J=4.6 Hz, 1H), 6.78 (d, J=4.8 Hz, 1H), 4.72 (br s, 2H), 3.14-3.25 (m, 1H), 2.08 (s, 3H), 1.14 (d, J=6.8 Hz, 6H). m/z (ESI, +ve ion): 151.1 (M+H)$^+$.

Step 3: 2,5,6-Trichloro-N-((2-isopropyl-4-methylpyridin-3-yl)carbamoyl)nicotinamide To a −78° C. slurry of 2,5,6-trichloronicotinamide (Intermediate A, 3.10 g, 13.8 mmol) in THF (46 mL) was added oxalyl chloride (2 M solution in DCM, 7.4 mL, 14.7 mmol) slowly via syringe. The resulting slurry was heated at 60° C. for 3.5 h, then heating was stopped and the reaction was cooled to −78° C. Triethylamine (6.0 mL, 42.6 mmol) was added followed by a solution of 2-isopropyl-4-methylpyridin-3-amine (Intermediate B, 2.12 g, 14.1 mmol) via cannula. The resulting slurry was warmed to rt and stirred for 1 h, then was partitioned between water (120 mL) and EtOAc (175 mL). The organic layer was dried over anhydrous $Na_2SO_4$ and concentrated in vacuo. The residue was suspended in 9:1 heptane/EtOAc and filtered. The filtered solids were collected to provide 2,5,6-trichloro-N-((2-isopropyl-4-methylpyridin-3-yl)carbamoyl)nicotinamide. $^1$H NMR (400 MHz, DMSO-$d_6$) δ ppm 11.31 (s, 1H), 9.54 (s, 1H), 8.66 (s, 1H), 8.34 (d, J=4.8 Hz, 1H), 7.16 (d, J=5.0 Hz, 1H), 3.24-3.33 (m, 1H), 2.22 (s, 3H), 1.17 (d, J=6.6 Hz, 6H). m/z (ESI, +ve ion): 400.9 (M+H)$^+$.

Step 4: (M)-6,7-Dichloro-1-(2-isopropyl-4-methylpyridin-3-yl)pyrido[2,3-d]pyrimidine-2,4(1H,3H)-dione (Intermediate C)

To an ice-cooled solution of 2,5,6-trichloro-N-((2-isopropyl-4-methylpyridin-3-yl)carbamoyl)nicotinamide (4.71 g, 11.7 mmol) in THF (55 mL) was added KHMDS (1 M solution in THF, 23.5 mL, 23.5 mmol) slowly via syringe. After 10 min the ice bath was removed and the resulting solution was stirred for an additional 30 min at rt. The reaction was quenched with saturated aqueous ammonium chloride (125 mL) and extracted with EtOAc (250 mL). The organic layer was washed with brine, dried over anhydrous $Na_2SO_4$, and concentrated in vacuo. The residue was purified by silica gel chromatography (eluent: 0-11% MeOH/DCM) to provide 6,7-dichloro-1-(2-isopropyl-4-methylpyridin-3-yl)pyrido[2,3-d]pyrimidine-2,4(1H,3H)-dione as a mixture of atropisomers. $^1$H NMR (400 MHz, DMSO-$d_6$) δ ppm 12.27 (br s, 1H), 8.59 (s, 1H), 8.52 (d, J=5.0 Hz, 1H), 7.28 (d, J=5.0 Hz, 1H), 2.82-2.92 (m, 1H), 2.04 (s, 3H), 1.08 (d, J=6.6 Hz, 3H), 1.01 (d, J=6.8 Hz, 3H). m/z (ESI, +ve ion): 365.0 (M+H)⁺.

A mixture of 6,7-dichloro-1-(2-isopropyl-4-methylpyridin-3-yl)pyrido[2,3-d]pyrimidine-2,4(1H,3H)-dione atropisomers (55.1 g) was purified by SFC (AD, 250×50 mm, 5 μm, 50% MeOH/CO2, 180 g/min, 102 bar) to obtain two peaks: Peak 1 ((P)-6,7-dichloro-1-(2-isopropyl-4-methylpyridin-3-yl)pyrido[2,3-d]pyrimidine-2,4(1H,3H)-dione, 22.1 g, >99% ee) and Peak 2 ((M)-6,7-dichloro-1-(2-isopropyl-4-methylpyridin-3-yl)pyrido[2,3-d]pyrimidine-2,4(1H,3H)-dione, 23.2 g, >99% ee).

Step 5: (M)-6-Chloro-7-(2-fluorophenyl)-1-(2-isopropyl-4-methylpyridin-3-yl)pyrido[2,3-d]pyrimidine-2,4(1H,3H)-dione (Intermediate D)

A mixture of (M)-6,7-dichloro-1-(2-isopropyl-4-methylpyridin-3-yl)pyrido[2,3-d]pyrimidine-2,4(1H,3H)-dione (Intermediate C, 4.40 g, 12.1 mmol), (2-fluorophenyl)boronic acid (2.53 g, 18.1 mmol; Combi-Blocks, San Diego, Calif.), KOAc (9.46 g, 96 mmol), and (1,1'-bis(diphenylphosphino)ferrocene)dichloropalladium (0.882 g, 1.21 mmol) in 1,4-dioxane (57 mL)/water (1.7 mL) was sparged with nitrogen then stirred at 90° C. for 2 h. Additional (2-fluorophenyl) boronic acid (0.5 g) was added, and the reaction mixture was stirred for another 15 min. The reaction mixture was diluted with EtOAc (200 mL), added to a separatory funnel, and washed with water (2×100 mL). The organic layer was separated, dried over anhydrous Na₂SO₄, and concentrated in vacuo. The crude product was adsorbed onto silica and was purified by silica gel chromatography (silica gel, 0-100% EtOAc/heptane) to give (M)-6-chloro-7-(2-fluorophenyl)-1-(2-isopropyl-4-methylpyridin-3-yl)pyrido[2,3-d]pyrimidine-2,4(1H,3H)-dione (4.03 g, 9.49 mmol, 79% yield) as an off-white foam. ¹H NMR (400 MHz, CDCl₃) δ 8.91 (br s, 1H) 8.60 (s, 1H) 8.50-8.55 (m, 1H) 7.37-7.46 (m, 1H) 7.06-7.17 (m, 4H) 2.81 (spt, J=6.7 Hz, 1H) 2.10 (s, 3H) 1.24 (br d, J=6.8 Hz, 3H) 1.09 (br d, J=6.6 Hz, 3H). ¹⁹F NMR (377 MHz, CDCl₃) δ −112.87 (s, 1F). m/z (ESI, +ve ion): 424.9 (M+H)⁺.

Step 6: tert-Butyl (2R,5S,M)-4-(6-chloro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate. A solution of (M)-6-chloro-7-(2-fluorophenyl)-1-(2-isopropyl-4-methylpyridin-3-yl)pyrido[2,3-d]pyrimidine-2,4(1H,3H)-dione (Intermediate D, 1.08 g, 2.54 mmol), phosphoryl trichloride (0.284 mL, 3.05 mmol), and DIPEA (1.33 mL, 7.63 mmol) in acetonitrile (6 mL) was stirred at 80° C. for 30 min. The reaction mixture was removed from the heating block, and (2R,5S)-1-Boc-2,5-dimethylpiperazine (0.545 g, 2.54 mmol; AstaTech Inc., Bristol, Pa.) and DIPEA (1.328 mL, 7.63 mmol) were added. The reaction mixture was stirred at rt for 15 min. The reaction mixture was diluted with EtOAc (100 mL), added to a separatory funnel, and washed with saturated aqueous NaHCO₃ (2×75 mL). The organic layer was separated, dried over anhydrous Na₂SO₄, and concentrated in vacuo. The crude product was adsorbed onto silica and was purified by silica gel chromatography (elutent: 0-70% EtOAc-EtOH (3:1)/heptane) to give tert-butyl (2R,5S,M)-4-(6-chloro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (861 mg, 1.39 mmol, 55% yield) as a light yellow solid. ¹H NMR (400 MHz, CDCl₃) δ 8.45-8.52 (m, 1H) 8.11 (s, 1H) 7.41 (br d, J=5.4 Hz, 1H) 7.04-7.21 (m, 4H) 4.90-5.06 (m, 1H) 4.34-4.69 (m, 1H) 4.03-4.20 (m, 1H) 3.78-4.01 (m, 2H) 3.46-3.65 (m, 1H) 2.63-2.80 (m, 1H) 2.03 (br s, 3H) 1.52 (s, 9H) 1.25-1.31 (m, 6H) 1.23 (br d, J=7.0 Hz, 3H) 1.08 (br d, J=6.6 Hz, 3H). ¹⁹F NMR (377 MHz, CDCl₃) δ −112.51 (br s, 1F). m/z (ESI, +ve ion): 621.0 (M+H)⁺.

Step 7: 4-((2S,5R,M)-4-Acryloyl-2,5-dimethylpiperazin-1-yl)-6-chloro-7-(2-fluorophenyl)-1-(2-isopropyl-4-methylpyridin-3-yl)pyrido[2,3-d]pyrimidin-2(1H)-one A solution of tert-butyl (2R,5S,M)-4-(6-chloro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (0.861 g, 1.39 mmol) in 2,2,2-trifluoroacetic acid (11 mL, 140 mmol) was stirred at rt for 15 min. The reaction mixture was concentrated in vacuo. A solution of the resulting oil, DIPEA (0.724 mL, 4.16 mmol), and acryloyl chloride (0.5 M in DCM, 2.77 mL, 1.39 mmol) in DCM (7 mL) was stirred at rt for 15 min. The reaction mixture was diluted with EtOAc (100 mL), added to a separatory funnel, and washed with saturated aqueous NaHCO₃ (2×75 mL). The organic layer was separated, dried over anhydrous Na₂SO₄, and concentrated in vacuo. The crude product was adsorbed onto silica and was purified by silica gel chromatography (eluent: 0-100% EtOAc-EtOH (3:1)/heptane) to give 4-((2S,5R.M)-4-acryloyl-2,5-dimethylpiperazin-1-yl)-6-chloro-7-(2-fluorophenyl)-1-(2-isopropyl-4-methylpyridin-3-yl)pyrido[2,3-d]pyrimidin-2(1H)-one (562 mg, 4.93 mmol, 77% yield) as a light yellow solid. ¹H NMR (400 MHz, CDCl₃) δ 8.44-8.53 (m, 1H) 8.11 (s, 1H) 7.41 (br d, J=6.2 Hz, 1H) 7.04-7.22 (m, 4H) 6.52-6.71 (m, 1H) 6.40 (br t, J=15.2 Hz, 1H) 5.75-5.84 (m, 1H) 5.02-5.21 (m, 1H) 4.29-4.53 (m, 1H) 3.46-4.09 (m, 4H) 2.63-2.75 (m, 1H) 2.03 (br s, 3H) 1.39-1.49 (m, 3H) 1.24-1.36 (m, 3H) 1.23 (br d, J=5.0 Hz, 3H) 1.08 (br d, J=6.2 Hz, 3H). ¹⁹F NMR (377 MHz, CDCl₃) δ −112.52 (s, 1F), −112.48 (s, 1F). m/z (ESI, +ve ion): 574.8 (M+H)⁺.

Example 2

4-((2S,5R,M)-4-Acryloyl-2,5-dimethylpiperazin-1-yl)-6-chloro-7-(2-fluoro-6-hydroxyphenyl)-1-(2-isopropyl-4-methylpyridin-3-yl)pyrido[2,3-d]pyrimidin-2(1H)-one

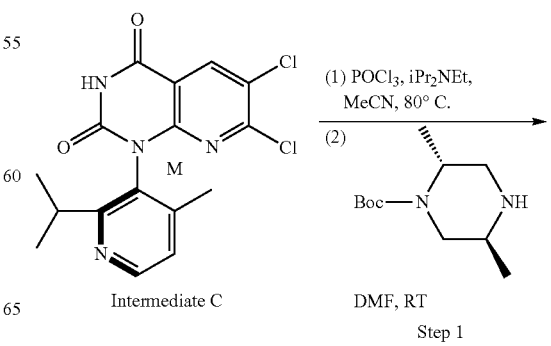

-continued

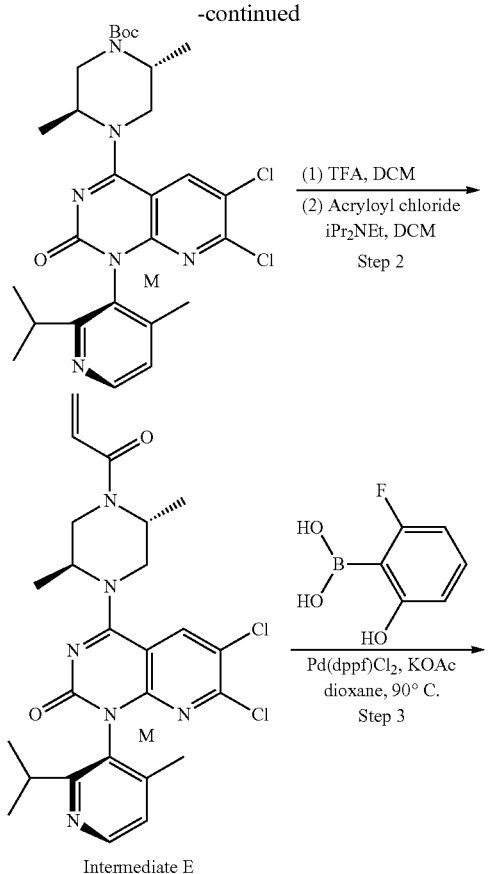

Step 1: (2R,5S,M)-tert-Butyl 4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate A 250-mL round-bottomed flask was charged with (M)-6,7-dichloro-1-(2-isopropyl-4-methylpyridin-3-yl)pyrido[2,3-d]pyrimidine-2,4(1H,3H)-dione (Intermediate C, 6.65 g, 18.2 mmol) and DIPEA (4.8 mL, 27.3 mmol) in acetonitrile (91 mL) followed by phosphorous oxychloride (2.6 mL, 27.3 mmol). The resulting mixture was stirred at 80° C. for 30 min and then concentrated in vacuo to give (M)-4,6,7-trichloro-1-(2-isopropyl-4-methylpyridin-3-yl)pyrido[2,3-d]pyrimidin-2(1H)-one as a brown solid. The crude brown solid was used in next step without purification. m/z (ESI, +ve): 383.0 (M+H)$^+$.

To a mixture of crude (M)-4,6,7-trichloro-1-(2-isopropyl-4-methylpyridin-3-yl)pyrido[2,3-d]pyrimidin-2(1H)-one and DIPEA (4.8 mL, 27.3 mmol) in DMF (50 mL) was added (2R,5S)-1-Boc-2,5-dimethylpiperazine (4.29 g, 20.03 mmol, AstaTech Inc., Bristol, Pa.) and the mixture was stirred at rt for 15 min. The mixture was added to ice water (80 mL) and stirred for 15 min. The resulting precipitates was collected by filtration, washed with water, and dried to give tert-butyl (2R,5S,M)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (4.70 g, 8.37 mmol, 46.0% yield) as a yellow solid. The filtrate was extracted with EtOAc (2×100 mL). The combined organic extracts were dried over MgSO$_4$. The solution was filtered and concentrated in vacuo to give additional title compound (5.51 g, 9.81 mmol, 53.9% yield) as a yellow solid. $^1$H NMR (400 MHz, DMSO-d$_6$) δ ppm 8.59 (br d, J=4.8 Hz, 1H), 8.54 (s, 1H), 7.40 (br d, J=2.7 Hz, 1H), 4.87 (br s, 1H), 4.23-4.44 (m, 1H), 4.01-4.09 (m, 1H), 3.95 (br s, 1H), 3.73 (br dd, J=13.7, 2.5 Hz, 1H), 3.46-3.65 (m, 1H), 2.67-2.76 (m, 1H), 2.04 (s, 3H), 1.45-1.57 (m, 9H), 1.36 (d, J=6.6 Hz, 3H), 1.08-1.18 (m, 9H). m/z (ESI, +ve): 561.2 (M+H)$^+$.

Step 2: 4-((2S,5R,M)-4-Acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate E)

To a solution of tert-butyl (2R,5S,M)-4-(6,7-dichloro-1-(2-isopropyl-4-methylpyridin-3-yl)-2-oxo-1,2-dihydropyrido[2,3-d]pyrimidin-4-yl)-2,5-dimethylpiperazine-1-carboxylate (5.51 g, 9.81 mmol) in DCM (20 mL) was added trifluoroacetic acid (10 mL, 134 mmol) at rt and the mixture was stirred for 1 h. After the reaction was complete, the mixture was concentrated in vacuo to afford (M)-6,7-dichloro-4-((2S,5R)-2,5-dimethylpiperazin-1-yl)-1-(2-isopropyl-4-methylpyridin-3-yl)pyrido[2,3-d]pyrimidin-2(1H)-one, m/z (ESI, +ve): 461.2 (M+H)$^+$.

To the above (M)-6,7-dichloro-4-((2S,5R)-2,5-dimethylpiperazin-1-yl)-1-(2-isopropyl-4-methylpyridin-3-yl)pyrido[2,3-d]pyrimidin-2(1H)-one and N,N-diisopropylethylamine (8.6 mL, 49.1 mmol) in DCM (20 mL) was added acryloyl chloride (0.8 mL, 9.81 mmol) at 0° C. and the mixture was stirred for 1 h. The reaction mixture was diluted with DCM (50 mL) and washed with sat'd. ammonium chloride solution (50 mL). To the aqueous was added sat'd sodium chloride (25 mL) and the mixture was extracted with DCM (50 mL×2). The organic extracts were combined and dried over MgSO$_4$. The solution was filtered and concentrated in vacuo to give a brown oil. The crude brown oil was adsorbed onto a plug of silica gel and purified by silica gel chromatography (eluent: 0-10% of MeOH/DCM) to give (M)-4-((2S,5R)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (4.66 g, 9.04 mmol, 92% yield) as a light yellow foam. $^1$H NMR (400 MHz, DMSO-d$_6$) δ ppm 8.46-8.54 (m, 2H), 7.30 (d, J=5.0 Hz, 1H), 6.82 (ddd, J=16.5, 14.0, 10.5 Hz, 1H), 6.18 (dd, J=16.7, 2.2 Hz, 1H), 5.74 (dt, J=10.4, 2.7 Hz, 1H), 4.78-4.91 (m, 1H), 4.39-4.75 (m, 1H), 3.97-4.16 (m, 1H), 3.94 (br s, 1H), 3.83 (br d, J=3.9 Hz, 1H), 3.49 (br dd, J=13.9, 3.7 Hz, 1H), 2.59-2.70 (m, 1H), 1.97 (s, 3H), 1.25-1.32 (m, 3H), 1.09-1.20 (m, 3H), 1.05 (dd, J=11.4, 6.6 Hz, 6H). m/z (ESI, +ve): 515.2 (M+H)+.

Step 3: 4-((2S,5R,M)-4-Acryloyl-2,5-dimethylpiperazin-1-yl)-6-chloro-7-(2-fluoro-6-hydroxyphenyl)-1-(2-isopropyl-4-methylpyridin-3-yl)pyrido[2,3-d]pyrimidin-2(1H)-one To a 50-mL round-bottomed flask was added 4-((2S,5R,M)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate E, 188 mg, 0.37 mmol), (2-fluoro-6-hydroxyphenyl)boronic acid (114 mg, 0.73 mmol, Combi-Blocks, San Diego, Calif.), dichloro[1,1'-bis(diphenylphosphino)ferrocene]palladium (II) dichloromethane adduct (27 mg, 0.04 mmol), KOAc (179 mg, 1.82 mmol), and 1,4-dioxane (4.0 mL) with 2 drops of water. The reaction mixture was stirred and heated at 90° C. for 18 h. The resulting mixture was concentrated in vacuo. The resulting crude product was adsorbed onto a plug of silica gel and purified by silica gel chromatography (eluent: 0-10% of EtOAc (with 10% MeOH)/heptane) to give 4-((2S,5R,M)-4-acryloyl-2,5-dimethylpiperazin-1-yl)-6-chloro-7-(2-fluoro-6-hydroxyphenyl)-1-(2-isopropyl-4-methylpyridin-3-yl)pyrido[2,3-d]pyrimidin-2(1H)-one (16 mg, 0.03 mmol, 7.4% yield) as a yellow solid. $^1$H NMR (400 MHz, DMSO-$d_6$) δ ppm 10.10 (br d, J=17.6 Hz, 1H), 8.44 (br s, 1H), 8.38 (d, J=4.8 Hz, 1H), 7.10-7.31 (m, 2H), 6.78-6.96 (m, 1H), 6.59-6.75 (m, 2H), 6.20 (dd, J=16.7, 2.0 Hz, 1H), 5.68-5.84 (m, 1H), 4.78-4.88 (m, 1H), 4.50 (br d, J=1.7 Hz, 1H), 4.08-4.29 (m, 2H), 3.86 (br d, J=9.1 Hz, 2H), 2.61-2.80 (m, 1H), 1.91 (br s, 3H), 1.35 (br d, J=6.4 Hz, 3H), 1.18-1.30 (m, 3H), 1.07 (d, J=6.8 Hz, 3H), 0.95 (br d, J=6.4 Hz, 3H). $^{19}$F NMR (376 MHz, DMSO-$d_6$) δ ppm −115.82 (br d, J=266.2 Hz, 1F). m/z (ESI, +ve): 591.2 (M+H)+.

Example 3

4-((2S,5R,M)-4-Acryloyl-2,5-dimethylpiperazin-1-yl)-7-(2-amino-6-fluorophenyl)-6-chloro-1-(2-isopropyl-4-methylpyridin-3-yl)pyrido[2,3-d]pyrimidin-2(1H)-one

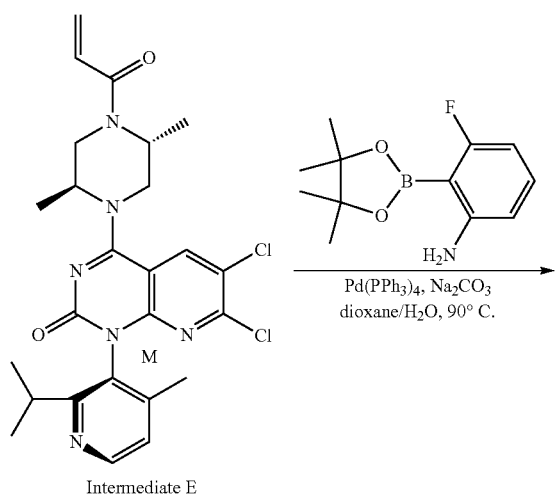

Intermediate E

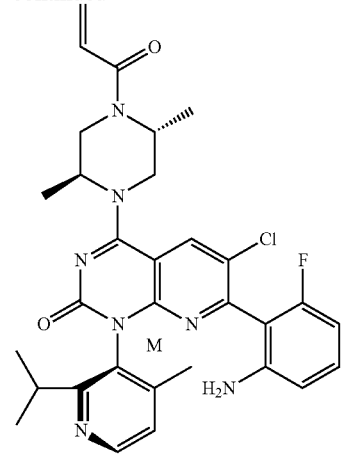

A mixture of 4-((2S,5R,M)-4-acryloyl-2,5-dimethylpiperazin-1-yl)-6,7-dichloro-1-(2-isopropyl-4-methylpyridin-3-yl)pyrido[2,3-d]pyrimidin-2(1H)-one (Intermediate E, 3.07 g, 5.96 mmol), tetrakis(triphenylphosphine)palladium (0.34 g, 0.30 mmol), (2-amino-6-fluorophenyl)boronic acid pinacol ester (1.55 g, 6.55 mmol, CombiPhos, Trenton, N.J.) and sodium carbonate, anhydrous, powder (3.16 g, 29.8 mmol) in 1,4-dioxane (20 mL)/water (10 mL) was stirred at 90° C. for 40 min. To the resulting mixture was added water (25 mL) and the mixture was extracted with EtOAc (2×50 mL). The organic extracts were combined and dried over MgSO$_4$. The solution was filtered and concentrated in vacuo to give the crude product as a yellow solid. The resulting crude product was adsorbed onto a plug of silica gel and purified by silica gel chromatography (eluent: 0-10% EtOAc (with 10% MeOH)/heptane) to give 4-((2S,5R,M)-4-acryloyl-2,5-dimethylpiperazin-1-yl)-7-(2-amino-6-fluorophenyl)-6-chloro-1-(2-isopropyl-4-methylpyridin-3-yl)pyrido[2,3-d]pyrimidin-2(1H)-one (1.83 g, 3.09 mmol, 52.0% yield) as a yellow solid. $^1$H NMR (400 MHz, DMSO-$d_6$) δ ppm 8.43 (s, 1H), 8.39 (d, J=4.8 Hz, 1H), 7.19 (d, J=4.8 Hz, 1H), 7.00-7.11 (m, 1H), 6.82 (br dd, J=16.6, 10.6 Hz, 1H), 6.45 (d, J=8.3 Hz, 1H), 6.27-6.35 (m, 1H), 6.19 (dd, J=16.6, 2.3 Hz, 1H), 5.76 (ddd, J=10.1, 5.5, 2.2 Hz, 1H), 5.07-5.19 (m, 2H), 4.45-4.90 (m, 2H), 3.47-4.24 (m, 4H), 2.60-2.88 (m, 1H), 1.85-1.99 (m, 3H), 1.30-1.39 (m, 3H), 1.16-1.29 (m, 3H), 1.03-1.11 (m, 3H), 0.87-1.03 (m, 3H). $^{19}$F NMR (376 MHz, DMSO-$d_6$) δ ppm −116.01--115.34 (m, 1F). m/z (ESI, +ve): 590.2 (M+H)+.

Example 4

4-((2S,5R,M)-4-Acryloyl-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one

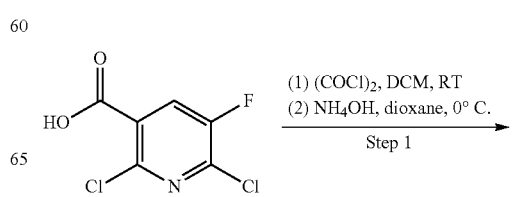

-continued

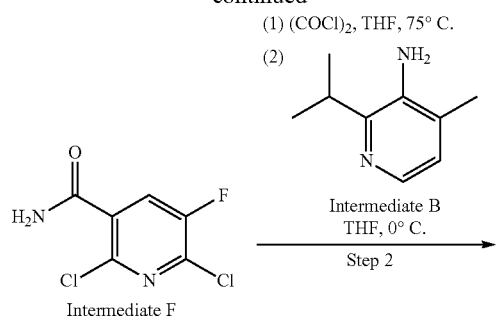

Intermediate F

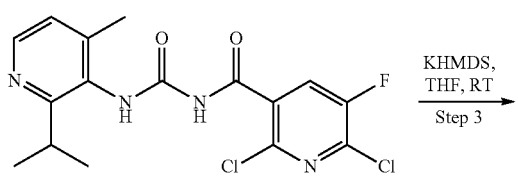

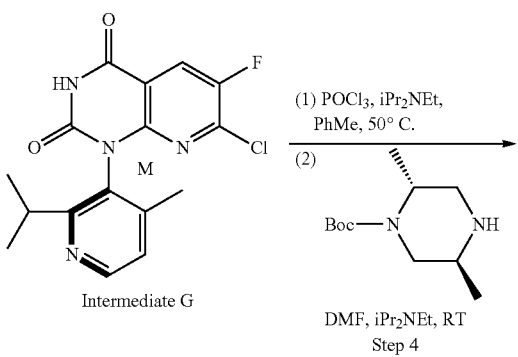

Intermediate G

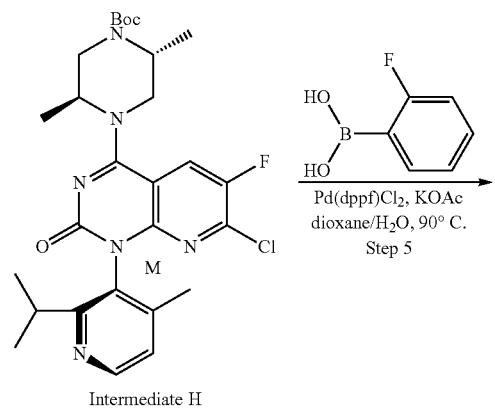

Intermediate H

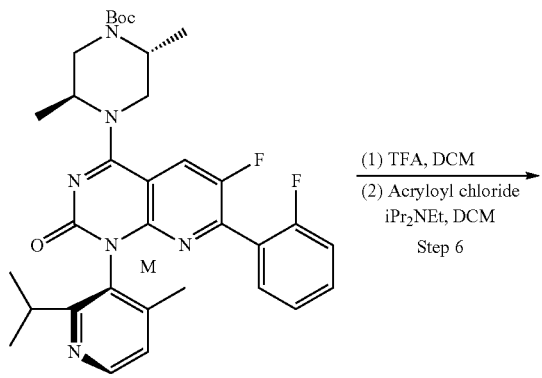

-continued

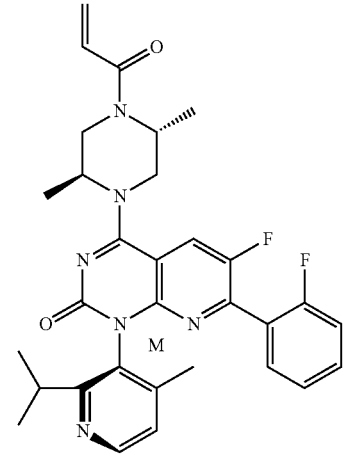

Step 1: 2,6-Dichloro-5-fluoronicotinamide (Intermediate F)

To a mixture of 2,6-dichloro-5-fluoro-nicotinic acid (4.0 g, 19.1 mmol, AstaTech Inc., Bristol, Pa.) in DCM (48 mL) was added oxalyl chloride (2 M solution in DCM, 11.9 mL, 23.8 mmol), followed by a catalytic amount of DMF (0.05 mL). The reaction mixture was stirred at rt overnight and then was concentrated in vacuo. The residue was dissolved in 1,4-dioxane (48 mL) and cooled to 0° C. Ammonium hydroxide solution (28-30% $NH_3$ basis, 3.6 mL, 28.6 mmol) was added slowly via syringe. The resulting mixture was stirred at 0° C. for 30 min and then concentrated. The residue was diluted with a 1:1 mixture of EtOAc/heptane, was agitated for 5 min, and then was filtered. The filtered solids were discarded, and the remaining mother liquor was partially concentrated to half the original volume and was filtered. The filtered solids were washed with heptane and dried in a reduced-pressure oven (45° C.) overnight to provide 2,6-dichloro-5-fluoronicotinamide. $^1$H NMR (400 MHz, DMSO-$d_6$) δ ppm 8.23 (d, J=7.9 Hz, 1H) 8.09 (br s, 1H) 7.93 (br s, 1H). m/z (ESI, +ve ion): 210.9 (M+H)$^+$.

Step 2: 2,6-Dichloro-5-fluoro-N-((2-isopropyl-4-methylpyridin-3-yl)carbamoyl)nicotinamide To an ice-cooled slurry of 2,6-dichloro-5-fluoronicotinamide (Intermediate F, 5.0 g, 23.9 mmol) in THF (20 mL) was added oxalyl chloride (2 M solution in DCM, 14.4 mL, 28.8 mmol) slowly via syringe. The resulting mixture was heated at 75° C. for 1 h, then heating was stopped, and the reaction was concentrated to half the initial volume. After cooling to 0° C., THF (20 mL) was added, followed by a solution of 2-isopropyl-4-methylpyridin-3-amine (Intermediate B, 3.59 g, 23.92 mmol) in THF (10 mL), dropwise via cannula. The resulting mixture was stirred at 0° C. for 1 h and then the reaction was quenched with a 1:1 mixture of brine and saturated aqueous ammonium chloride. The mixture was extracted with EtOAc and the combined organic layers were dried over anhydrous $Na_2SO_4$ and concentrated to provide 2,6-dichloro-5-fluoro-N-((2-isopropyl-4-methylpyridin-3-yl)carbamoyl)nicotinamide. This material was used without further purification in the following step. m/z (ESI, +ve ion): 385.1 (M+H)$^+$.

Step 3: (M)-7-Chloro-6-fluoro-1-(2-isopropyl-4-methylpyridin-3-yl)pyrido[2,3-d]pyrimidine-2,4(1H, 3H)-dione (Intermediate G)

To an ice-cooled solution of 2,6-dichloro-5-fluoro-N-((2-isopropyl-4-methylpyridin-3-yl)carbamoyl)nicotinamide (9.2 g, 24.0 mmol) in THF (40 mL) was added KHMDS (1 M solution in THF, 50.2 mL, 50.2 mmol) slowly via syringe. The ice bath was removed and the resulting mixture was stirred for 40 min at rt. The reaction was quenched with saturated aqueous ammonium chloride and extracted with EtOAc. The combined organic layers were dried over anhydrous $Na_2SO_4$ and concentrated in vacuo. The residue was purified by silica gel chromatography (eluent: 0-50% EtOAc-EtOH (3:1)/heptane) to provide 7-chloro-6-fluoro-1-(2-isopropyl-4-methylpyridin-3-yl)pyrido[2,3-d]pyrimidine-2,4(1H,3H)-dione as a mixture of atropisomers. $^1$H NMR (400 MHz, DMSO-$d_6$) δ ppm 12.27 (br s, 1H), 8.48-8.55 (m, 2H), 7.29 (d, J=4.8 Hz, 1H), 2.87 (quin, J=6.6 Hz, 1H), 1.99-2.06 (m, 3H), 1.09 (d, J=6.6 Hz, 3H), 1.01 (d, J=6.6 Hz, 3H). $^{19}$F NMR (376 MHz, DMSO-$d_6$) δ: −126.90 (s, 1F). m/z (ESI, +ve ion): 349.1 (M+H)$^+$.

A mixture of 7-chloro-6-fluoro-1-(2-isopropyl-4-methylpyridin-3-yl)pyrido[2,3-d]pyrimidine-2,4(1H,3H)-dione atropisomers (648 g) was purified by SFC (AD, 150×50 mm, m, 50% MeOH/CO2, 180 g/min, 102 bar) to obtain two peaks: Peak 1 (P-7-chloro-6-fluoro-1-(2-isopropyl-4-methylpyridin-3-yl)pyrido[2,3-d]pyrimidine-2,4(1H,3H)-dione, 230.6 g, >99% ee) and Peak 2 ((M)-7-chloro-6-fluoro-1-(2-isopropyl-4-methylpyridin-3-yl)pyrido[2,3-d]pyrimidine-2, 4(1H,3H)-dione, 227.8 g, 97.1% ee).

Step 4: (2R,5S,M)-tert-Butyl 4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate H)

To a solution of (M)-7-chloro-6-fluoro-1-(2-isopropyl-4-methylpyridin-3-yl)pyrido[2,3-d]pyrimidine-2,4(1H,3H)-dione (Intermediate G, 4.75 g, 13.62 mmol) in toluene (54.5 mL) was added DIPEA (4.76 mL, 27.2 mmol) followed by phosphorous oxychloride (2.54 mL, 27.2 mmol). The reaction was heated to 50° C. for 50 min. The reaction was concentrated in vacuo to give crude (M)-4,7-dichloro-6-fluoro-1-(2-isopropyl-4-methylpyridin-3-yl)pyrido[2,3-d]pyrimidin-2(1H)-one as a brown solid that was used directly in the next step. m/z (ESI, +ve): 367.0 (M+H)$^+$.

To crude (M)-4,7-dichloro-6-fluoro-1-(2-isopropyl-4-methylpyridin-3-yl)pyrido[2,3-d]pyrimidin-2(1H)-one was added DMF (113 mL) followed by tert-butyl (2R,5S)-2,5-dimethylpiperazine-1-carboxylate (2.92 g, 13.62 mmol, AstaTech Inc., Bristol, Pa.). To the solution was added DIPEA (11.9 mL, 68.1 mmol) dropwise with stirring. After stirring for 5 min, the reaction was diluted with water and EtOAc. The organic layer was washed with 1 M LiCl and brine, then dried over MgSO$_4$. The material was purified by silica gel chromatography (eluent: 0-80% EtOAc:EtOH (3:1) in heptane) to afford tert-butyl (2R,5S,M)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (6.85 g, 12.57 mmol, 92% yield) as a yellow orange solid. $^1$H NMR (400 MHz, DMSO-$d_6$) δ ppm 8.49 (d, J=4.77 Hz, 1H) 8.39 (d, J=8.50 Hz, 1H) 7.26 (d, J=4.98 Hz, 1H) 4.80 (br s, 1H) 4.18-4.38 (m, 1H) 3.99 (br d, J=14.72 Hz, 1H) 3.78-3.90 (m, 1H) 3.64-3.73 (m, 1H) 3.45-3.61 (m, 1H) 2.60 (dt, J=13.37, 6.58 Hz, 1H) 1.95 (s, 3H) 1.45 (s, 9H) 1.29 (br d, J=6.63 Hz, 3H) 1.11 (br d, J=6.01 Hz, 3H) 1.06 (d, J=6.84 Hz, 3H) 1.03 (d, J=6.63 Hz, 3H). $^{19}$F NMR (376 MHz, DMSO-$d_6$) δ ppm −128.25 (s, 1F). m/z (ESI, +ve): 545.2 (M+H)$^+$.

Step 5: (2R,5S,M)-tert-Butyl 4-(6-fluoro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate A dram vial with teflon screw cap was charged with KOAc (0.330 g, 3.36 mmol). The vial was sealed and evacuated/backfilled with nitrogen. A solution of tert-butyl (2R,5S,M)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate H, 0.366 g, 0.671 mmol) in dioxane (4.26 mL) was added followed by water (0.2 mL). The reaction was heated to 90° C. for 2 min. Dichloro[1,1'-bis(diphenylphosphino)ferrocene]palladium (II) dichloromethane adduct (0.049 g, 0.067 mmol, Strem Chemicals, Newburyport, Mass.), and (2-fluorophenyl)boronic acid (0.188 g, 1.343 mmol, Combi-Blocks, San Diego, Calif.) were added and the reaction was stirred at 90° C. for 3 h. The reaction was cooled to rt and diluted with water and EtOAc. The organic phase was washed with brine, dried over MgSO$_4$ and concentrated in vacuo. The crude residue was purified via silica gel flash chromatography (eluent: 0-60% EtOAc:EtOH (3:1)/heptane) to afford tert-butyl (2R,5S,M)-4-(6-fluoro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (0.336 g, 0.555 mmol, 83% yield) as a yellow solid. $^1$H NMR (400 MHz, DMSO-$d_6$) δ ppm 8.44 (d, J=4.98 Hz, 1H) 8.32 (d, J=9.54 Hz, 1H) 7.51-7.60 (m, 1H) 7.26-7.38 (m, 3H) 7.22 (d, J=4.98 Hz, 1H) 4.84 (br s, 1H) 4.25-4.42 (m, 1H) 4.12 (br d, J=13.89 Hz, 1H) 3.83 (br d, J=12.44 Hz, 1H) 3.65-3.75 (m, 1H) 3.46-3.63 (m, 1H) 2.70 (dt, J=13.48, 6.74 Hz, 1H) 1.95 (s, 3H) 1.46 (s, 9H) 1.33 (d, J=6.63 Hz, 3H) 1.16-1.20 (m, 3H) 1.08 (d, J=6.84 Hz, 3H) 0.98 (d, J=6.63 Hz, 3H). 19F NMR (376 MHz, DMSO-$d_6$) δ ppm −113.72 (m, 1F) −129.04 (m, 1F). m/z (ESI, +ve): 605.2 (M+H)$^+$.

Step 6: 4-((2S,5R,M)-4-Acryloyl-2,5-dimethylpiperazin-1-yl)-6-fluoro-7-(2-fluorophenyl)-1-(2-isopropyl-4-methylpyridin-3-yl)pyrido[2,3-d]pyrimidin-2 (1H)-one To a solution of tert-butyl (2R,5S,M)-4-(6-fluoro-7-(2-fluorophenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (0.335 g, 0.554 mmol) in DCM (11.1 mL) was added trifluoroacetic acid (1.65 mL, 22.2 mmol). The reaction mixture was stirred at rt for 1 h. The reaction mixture was concentrated in vacuo to provide crude 4-((2S,5R,M)-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one that was used without further purification.

The crude 4-((2S,5R,M)-2,5-dimethylpiperazin-1-yl)-6-fluoro-7-(2-fluorophenyl)-1-(2-isopropyl-4-methylpyridin- 3-yl)pyrido[2,3-d]pyrimidin-2(1H)-one was taken up in DCM (15 mL). DIPEA (0.484 mL, 2.77 mmol) was added followed by acryloyl chloride (1.1 M solution in DCM, 0.453 mL, 0.499 mmol). The reaction mixture was stirred for 5 min. The reaction mixture was concentrated in vacuo. The crude material was purified via silica gel chromatography (eluent: 20-80% EtOAc:EtOH (3:1)/heptane) to afford 4-((2S,5R,M)-4-acryloyl-2,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one (0.184 g, 0.329 mmol, 59.5% yield). $^1$H NMR (400 MHz, DMSO-d$_6$) δ ppm 8.44 (d, J=4.98 Hz, 1H) 8.33-8.39 (m, 1H) 7.52-7.60 (m, 1H) 7.25-7.39 (m, 3H) 7.23 (d, J=4.77 Hz, 1H) 6.77-6.93 (m, 1H) 6.14-6.26 (m, 1H) 5.71-5.81 (m, 1H) 4.11-4.97 (m, 4H) 3.48-3.93 (m, 2H) 2.71 (td, J=6.27, 3.63 Hz, 1H) 1.95 (s, 3H) 1.32 (br t, J=7.26 Hz, 3H) 1.17-1.28 (m, 3H) 1.08 (d, J=6.63 Hz, 3H) 0.98 (br d, J=6.63 Hz, 3H). $^{19}$F NMR (376 MHz, DMSO-d$_6$) δ ppm −113.88−−113.54 (m, 1F) −129.19−−128.86 (m, 1F). m/z (ESI, +ve): 559.2 (M+H)$^+$.

Example 5

4-((2S,5R,M)-4-Acryloyl-2,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one

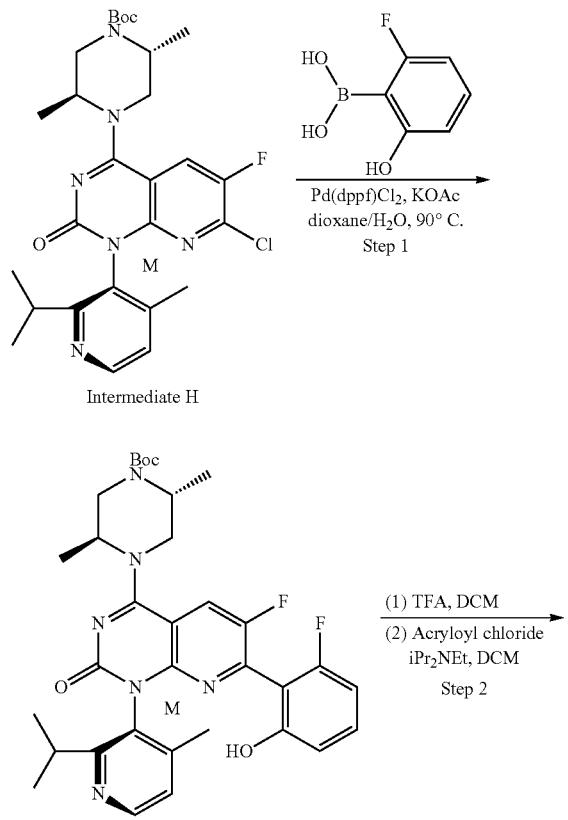

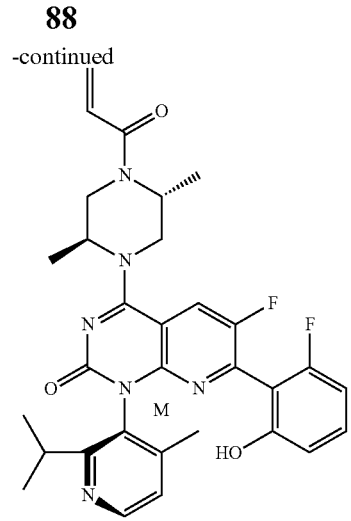

Step 1: (2R,5S,M)-tert-Butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-2,5-dimethylpiperazine-1-carboxylate A dram vial with teflon screw cap was charged with KOAc (0.315 g, 3.21 mmol). The vial was capped and evacuated/backfilled with nitrogen. A solution of tert-butyl (2R,5S,M)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate H, 0.35 g, 0.642 mmol) in dioxane (4.08 mL) was added followed by water (0.2 mL). The reaction mixture was heated to 90° C. for 2 min. Dichloro[1,1'-bis(diphenylphosphino)ferrocene]palladium (II) dichloromethane adduct (0.047 g, 0.064 mmol, Strem Chemicals, Newburyport, Mass.), and (2-fluoro-6-hydroxyphenyl)boronic acid (0.200 g, 1.28 mmol, Wuxi) were added and the reaction was stirred at 90° C. for 3 h. The reaction was cooled to rt and diluted with water and EtOAc. The organic phase was washed with brine, dried over MgSO$_4$ and concentrated in vacuo. The crude residue was purified by silica gel chromatography (eluent: 0-60% EtOAc-EtOH (3:1)/heptane) to afford tert-butyl (2R,5S,M)-4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-2,5-dimethylpiperazine-1-carboxylate (0.375 g, 0.604 mmol, 94% yield) as a yellow solid. $^1$H NMR (400 MHz, DMSO-d$_6$) δ ppm 10.19 (br s, 1H) 8.39 (d, J=4.77 Hz, 1H) 8.26 (d, J=8.91 Hz, 1H) 7.24-7.32 (m, 1H) 7.19 (d, J=4.77 Hz, 1H) 6.74 (d, J=8.50 Hz, 1H) 6.69 (t, J=8.81 Hz, 1H) 4.76-4.88 (m, 1H) 4.26-4.44 (m, 1H) 4.15 (br d, J=14.30 Hz, 1H) 3.76-3.84 (m, 1H) 3.71 (m, 1H) 3.41-3.66 (m, 1H) 2.69 (quin, J=6.63 Hz, 1H) 1.91 (s, 3H) 1.46 (s, 9H) 1.34 (d, J=6.43 Hz, 3H) 1.19 (m, 3H) 1.07 (d, J=6.43 Hz, 3H) 0.95 (d, J=6.84 Hz, 3H). 19F NMR (376 MHz, DMSO-d$_6$) δ ppm −115.55 (m, 1F) −128.46 (br s, 1F). m/z (ESI, +ve): 621.2 (M+H)$^+$.

Step 2: 4-((2S,5R,M)-4-Acryloyl-2,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one To a solution of tert-butyl (2R,5S,M)-4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-2,5- dimethylpiperazine-1-carboxylate (0.375 g, 0.604 mmol) in DCM (12.1 mL) was added trifluoroacetic acid (1.80 mL, 24.2 mmol). The reaction mixture was stirred at rt for 2 h. The reaction mixture was concentrated in vacuo to provide crude 4-((2S,5R,M)-2,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one that was used without purification.

The crude 4-((2S,5R,M)-2,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one was taken up in DCM (15 mL) and cooled to 0° C. N,N'-Diisopropylethylamine (0.528 mL, 3.02 mmol) was added followed by dropwise addition of acryloyl chloride (1.1 M solution in DCM, 0.549 mL, 0.604 mmol). The reaction mixture was stirred for 5 min. The reaction mixture was concentrated in vacuo and the crude material was purified by silica gel chromatography (eluent: 0-80% EtOAc-EtOH (3:1)/heptane). The obtained product contained a small amount of bis-acylated (acylation of the phenolic hydroxy group in addition to the piperazine nitrogen) impurity. The material was treated with THF (3 mL) and 1N NaOH (0.6 mL). The reaction mixture was stirred for 15 min. The reaction was quenched with saturated ammonium chloride and the mixture was diluted with water and EtOAc. The organic phase was separated and the aqueous was extracted with additional EtOAc. The organic phases were combined, washed with brine, dried over MgSO$_4$ and concentrated in vacuo to afford 4-((2S,5R,M)-4-acryloyl-2,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2 (1H)-one (0.17 g, 0.296 mmol, 49.0% yield). $^1$H NMR (400 MHz, DMSO-d$_6$) δ ppm 10.20 (br s, 1H) 8.39 (br d, J=4.35 Hz, 1H) 8.26-8.32 (m, 1H) 7.24-7.33 (m, 1H) 7.19 (br d, J=4.15 Hz, 1H) 6.78-6.94 (m, 1H) 6.65-6.77 (m, 2H) 6.16-6.25 (m, 1H) 5.73-5.82 (m, 1H) 4.10-4.94 (m, 4H) 3.45-3.93 (m, 2H) 2.65-2.75 (m, 1H) 1.91 (s, 3H) 1.33 (br t, J=6.01 Hz, 3H) 1.19-1.30 (m, 3H) 1.07 (br d, J=6.63 Hz, 3H) 0.95 (br d, J=5.80 Hz, 3H). $^{19}$F NMR (376 MHz, DMSO-d$_6$) δ ppm −115.59--115.51 (m, 1F) −128.49--128.38 (m, 1F). m/z (ESI, +ve): 575.2 (M+H)$^+$.

Example 6

4-((2S,5R,M)-4-Acryloyl-2,5-dimethylpiperazin-1-yl)-7-(2-amino-6-fluorophenyl)-6-fluoro-1-(2-isopropyl-4-methylpyridin-3-yl)pyrido[2,3-d]pyrimidin-2(1H)-one

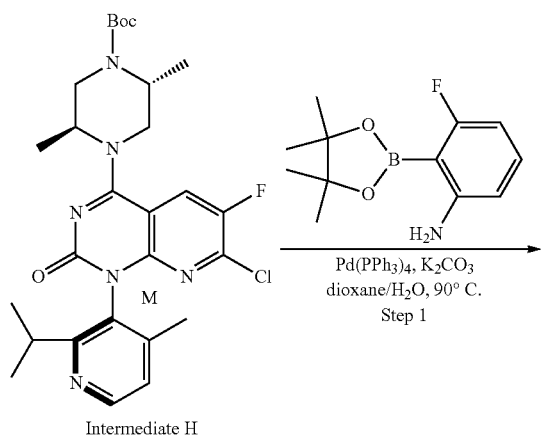

Intermediate H

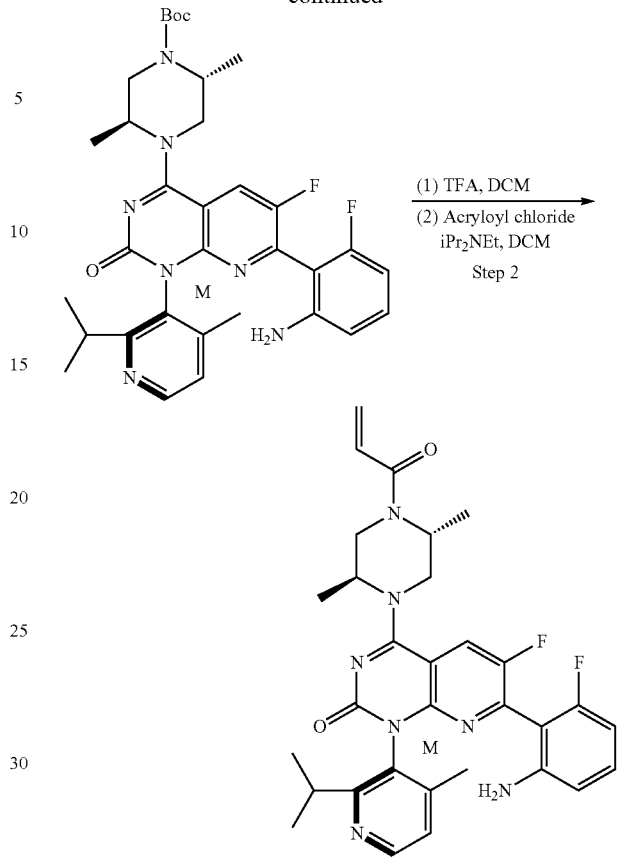

Step 1: (2R,5S,M)-tert-Butyl 4-(7-(2-amino-6-fluorophenyl)-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate A dram vial with teflon screw cap was charged with potassium carbonate (0.152 mL, 2.52 mmol), (2-amino-6-fluorophenyl)boronic acid pinacol ester (0.132 mL, 0.555 mmol, CombiPhos, Trenton, N.J.), tert-butyl (2R,5S,M)-4-(7-chloro-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (Intermediate H, 0.275 g, 0.505 mmol), and tetrakis(triphenylphosphine)palladium (0.058 g, 0.050 mmol, Strem Chemicals, Newburyport, Mass.). The vial was capped and evacuated/backfilled with nitrogen. 1,4-Dioxane (1.68 mL) was added followed by water (0.841 mL). The reaction mixture was stirred in a pre-heated 90° C. oil bath for 16 h. The reaction mixture was diluted with water and EtOAc. The phases were mixed and the organic layer was separated. The aqueous phase was extracted with additional EtOAc and the combined organic phases were washed with brine, dried over MgSO$_4$ and concentrated in vacuo. The crude residue was purified by silica gel chromatography (eluent: 20-100% EtOAc-EtOH (3:1)/heptane) to afford tert-butyl (2R,5S,M)-4-(7-(2-amino-6-fluorophenyl)-6-fluoro-1-(2-isopropyl-4-methylpyridin-3-yl)-2-oxo-1,2-dihydropyrido[2,3-d]pyrimidin-4-yl)-2,5-dimethylpiperazine-11-carboxylate (0.3 g, 0.484 mmol, 96% yield) as a yellow/orange solid. $^1$H NMR (400 MHz, DMSO-d$_6$) δ ppm 8.44 (d, J=4.98 Hz, 1H) 8.27 (d, J=9.54 Hz, 1H) 7.23 (d, J=4.98 Hz, 1H) 7.07-7.14 (m, 1H) 6.49 (d, J=8.29 Hz, 1H)

6.34-6.41 (m, 1H) 5.37 (s, 2H) 4.81 (br s, 1H) 4.25-4.44 (m, 1H) 4.13 (br d, J=13.89 Hz, 1H) 3.77-3.86 (m, 1H) 3.72 (br d, J=13.89 Hz, 1H) 3.48-3.64 (m, 1H) 2.66-2.79 (m, 1H) 1.94 (s, 3H) 1.46 (s, 8H) 1.43-1.49 (m, 1H) 1.34 (d, J=6.43 Hz, 3H) 1.20 (br dd, J=6.84, 2.90 Hz, 3H) 1.07 (d, J=6.63 Hz, 3H) 0.96 (d, J=6.63 Hz, 3H). $^{19}$F NMR (376 MHz, DMSO-$d_6$) δ ppm −114.23 (br d, J=28.61 Hz, 1F) −127.15 (br d, J=28.61 Hz, 1F). m/z (ESI, +ve): 620.3 (M+H)$^+$.

Step 2: 4-((2S,5R,M)-4-Acryloyl-2,5-dimethylpiperazin-1-yl)-7-(2-amino-6-fluorophenyl)-6-fluoro-1-(2-isopropyl-4-methylpyridin-3-yl)pyrido[2,3-d]pyrimidin-2(1H)-one To a solution of tert-butyl (2R,5S,M)-4-(7-(2-amino-6-fluorophenyl)-6-fluoro-1-(2-isopropyl-4-methylpyridin-3-yl)-2-oxo-1,2-dihydropyrido[2,3-d]pyrimidin-4-yl)-2,5-dimethylpiperazine-1-carboxylate (0.3 g, 0.484 mmol) in DCM (9.68 mL) was added trifluoroacetic acid (1.44 mL, 19.4 mmol). The reaction mixture was stirred at rt for 2 h. The reaction mixture was concentrated in vacuo to provide crude (M)-7-(2-amino-6-fluorophenyl)-4-((2S,5R)-2,5-dimethylpiperazin-1-yl)-6-fluoro-1-(2-isopropyl-4-methylpyridin-3-yl)pyrido[2,3-d]pyrimidin-2(1H)-one that was used without further purification.

To the crude (M)-7-(2-amino-6-fluorophenyl)-4-((2S,5R)-2,5-dimethylpiperazin-1-yl)-6-fluoro-1-(2-isopropyl-4-methylpyridin-3-yl)pyrido[2,3-d]pyrimidin-2(1H)-one was added DCM (10 mL). The solution was cooled to −20° C. DIPEA (0.423 mL, 2.42 mmol) was added followed by dropwise addition of acryloyl chloride (1.1 M solution in DCM, 0.396 mL, 0.436 mmol). The reaction mixture was stirred for 5 min. The reaction mixture was concentrated in vacuo and purified by silica gel chromatography (eluent: 0-80% EtOAc-EtOH (3:1)/heptane). The obtained yellow solid was taken up in EtOAc and washed sequentially with 1:1 saturated NaHCO$_3$:water and brine then dried over MgSO$_4$ and concentrated in vacuo to afford 4-((2S,5R,M)-4-acryloyl-2,5-dimethylpiperazin-1-yl)-7-(2-amino-6-fluorophenyl)-6-fluoro-1-(2-isopropyl-4-methylpyridin-3-yl)pyrido[2,3-d]pyrimidin-2(1H)-one (0.184 g, 0.321 mmol, 66.3% yield). $^1$H NMR (400 MHz, DMSO-$d_6$) δ ppm 8.44 (d, J=4.77 Hz, 1H) 8.27-8.32 (m, 1H) 7.21-7.24 (m, 1H) 7.07-7.14 (m, 1H) 6.78-6.92 (m, 1H) 6.48 (d, J=8.29 Hz, 1H) 6.34-6.41 (m, 1H) 6.20 (dd, J=16.59, 2.28 Hz, 1H) 5.73-5.79 (m, 1H) 5.37 (s, 2H) 4.12-4.91 (m, 4H) 3.47-3.89 (m, 2H) 2.66-2.78 (m, 1H) 1.94 (s, 3H) 1.33 (t, J=6.53 Hz, 3H) 1.18-1.29 (m, 3H) 1.07 (d, J=6.63 Hz, 3H) 0.96 (d, J=6.63 Hz, 3H). $^{19}$F NMR (376 MHz, DMSO-$d_6$) δ ppm −114.36--114.15 (m, 1F) −127.28--127.04 (m, 1F). m/z (ESI, +ve): 573.6 (M+H)$^+$.

Example 7

4-((2S,5R)-4-Acryloyl-2,5-dimethylpiperazin-1-yl)-6-chloro-1-(4,6-diisopropylpyrimidin-5-yl)-7-(2-fluorophenyl)pyrido[2,3-d]pyrimidin-2(1H)-one

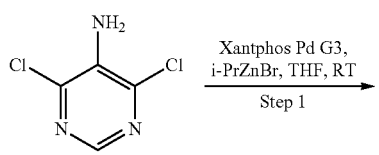

Xantphos Pd G3, i-PrZnBr, THF, RT

Step 1

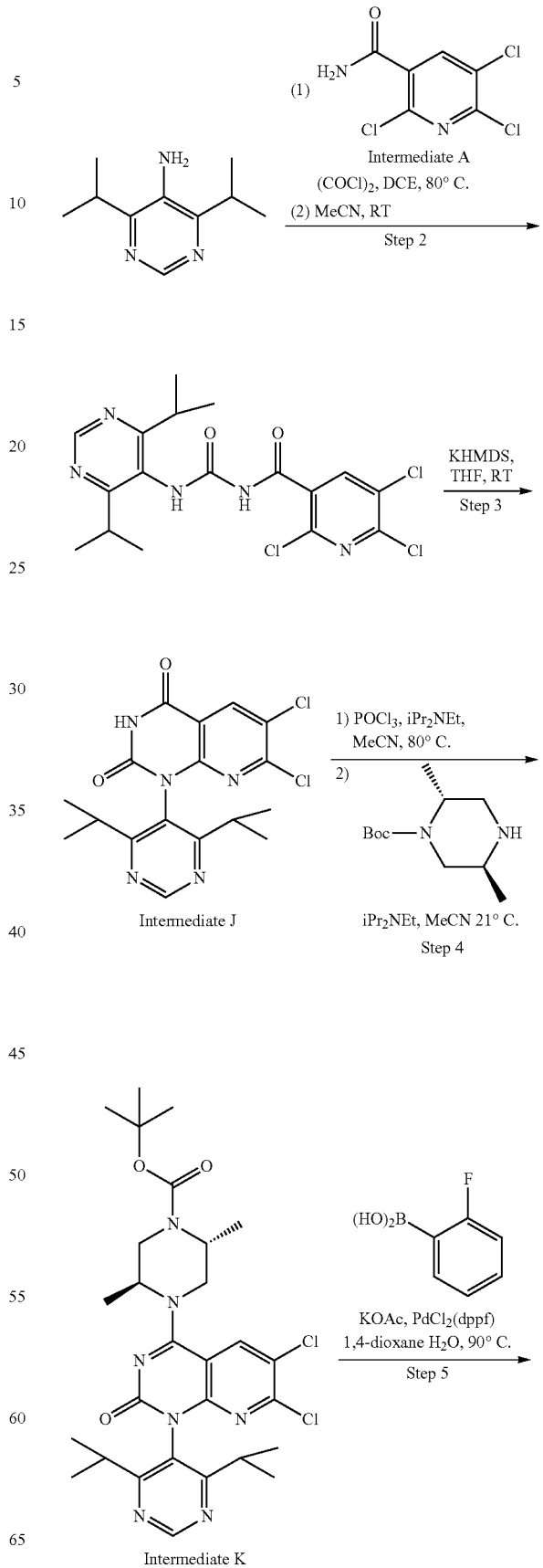

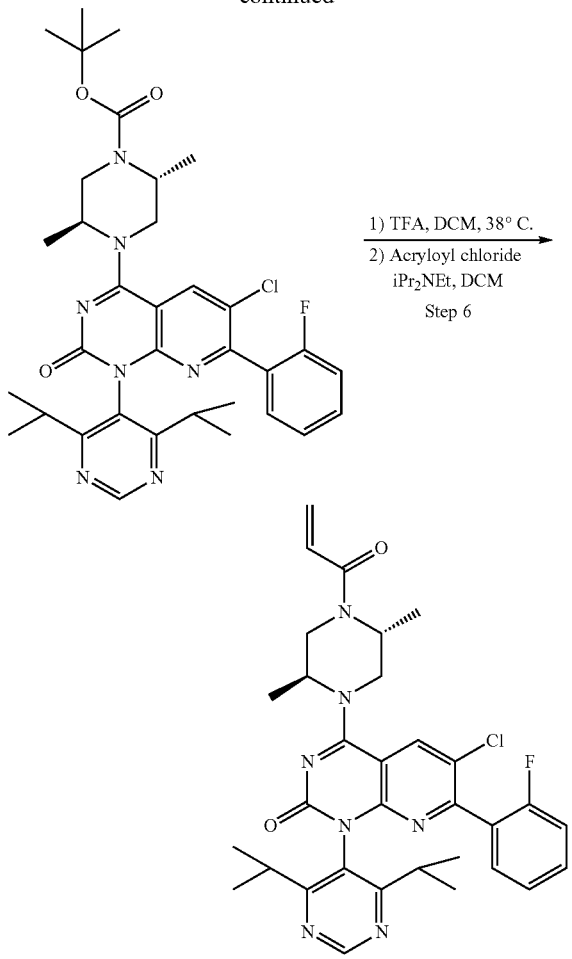

1) TFA, DCM, 38° C.
2) Acryloyl chloride
   iPr₂NEt, DCM

Step 6

Step 1: 4,6-Diisopropylpyrimidin-5-amine. A solution of 4,6-dichloro-5-aminopyrimidine (3.00 g, 18.29 mmol, Combi-Blocks Inc., San Diego, Calif.) in THF (18 mL) was degassed by bubbling argon into the mixture for 5 min. 2-Propylzinc bromide (0.5 M solution in THF, 91.0 mL, 45.5 mmol, Sigma-Aldrich, St. Louis, Mo.) was added via syringe followed by XantPhos Pd G3 (434 mg, 0.46 mmol, Sigma-Aldrich, St. Louis, Mo.). The resulting mixture was stirred at rt for 16 h and then was filtered through a pad of Celite. The filter cake was rinsed with EtOAc, and the filtrate was collected and concentrated in vacuo to afford 4,6-diisopropylpyrimidin-5-amine (3.45 g). This material was used without further purification in the following step. m/z (ESI, +ve ion): 180.2 (M+H)+.

Step 2: 2,5,6-Trichloro-N-((4,6-diisopropylpyrimidin-5-yl)carbamoyl)nicotinamide A solution of 2,5,6-trichloronicotinamide (Intermediate A, 3.30 g, 14.6 mmol) in 1,2-dichloroethane (49 mL) was treated with oxalyl chloride (2 M solution in DCM, 11.0 mL, 22.0 mmol). The mixture was heated at 80° C. for 45 min, then the heating was stopped and the reaction was concentrated in vacuo. The residue was dissolved in acetonitrile (49 mL), cooled to −10° C., and a solution of 4,6-diisopropylpyrimidin-5-amine (3.15 g, 17.6 mmol) in acetonitrile (5 mL) was added via cannula. The resulting mixture was stirred at rt overnight and was then concentrated in vacuo. The residue was suspended in warm 10:1 heptane/EtOAc (110 mL) and filtered. The filtrate was concentrated and the residue was purified by silica gel chromatography (eluent: 0-40% EtOAc/heptane) to provide 2,5,6-trichloro-N-((4,6-diisopropylpyrimidin-5-yl)carbamoyl)nicotinamide. $^1$H NMR (400 MHz, DMSO-$d_6$) δ ppm 11.30-11.46 (m, 1H), 9.66 (br s, 1H), 8.95-9.01 (m, 1H), 8.65-8.72 (m, 1H), 3.26 (s, 2H), 1.17 (d, J=6.6 Hz, 12H). m/z (ESI, +ve ion): 430.0 (M+H)$^+$.

Step 3: 6,7-Dichloro-1-(4,6-diisopropylpyrimidin-5-yl)pyrido[2,3-d]pyrimidine-2,4(1H,3H)-dione (Intermediate J)

To a −20° C. solution of 2,5,6-trichloro-N-((4,6-diisopropylpyrimidin-5-yl)carbamoyl)nicotinamide (2.10 g, 4.9 mmol) in THF (49 mL) was added KHMDS (1 M solution in THF, 12.2 mL, 12.2 mmol). The cooling bath was removed and the resulting mixture was stirred for 2 h at rt. The reaction mixture was quenched with saturated aqueous ammonium chloride (50 mL), diluted with brine, and extracted with 3:1 EtOAc/MeOH. The layers were separated and the aqueous layer was extracted with additional EtOAc. The combined organic layers were dried over anhydrous MgSO$_4$ and concentrated in vacuo. The residue was suspended in heptane/EtOAc and filtered. The filtrate was concentrated to provide 6,7-dichloro-1-(4,6-diisopropylpyrimidin-5-yl)pyrido[2,3-d]pyrimidine-2,4(1H,3H)-dione. $^1$H NMR (400 MHz, DMSO-$d_6$) δ ppm 12.33 (s, 1H), 9.18 (s, 1H), 8.61 (s, 1H), 2.90-3.02 (m, 2H), 1.10 (d, J=6.6 Hz, 6H), 0.99 (d, J=6.6 Hz, 6H). m/z (ESI, +ve ion): 394.1 (M+H)$^+$.

Step 4: (2R,5S)-tert-Butyl 4-(6,7-dichloro-1-(4,6-diisopropylpyrimidin-5-yl)-2-oxo-1,2-dihydropyrido[2,3-d]pyrimidin-4-yl)-2,5-dimethylpiperazine-1-carboxylate (Intermediate K). To a 150-mL round-bottomed flask was added 6,7-dichloro-1-(4,6-diisopropylpyrimidin-5-yl)pyrido[2,3-d]pyrimidine-2,4(1H,3H)-dione (Intermediate J, 0.400 g, 1.01 mmol) and N,N-diisopropylethylamine (0.230 mL, 1.32 mmol) in acetonitrile (5.07 mL). Then phosphorous oxychloride (0.113 mL, 1.22 mmol) was added slowly into the reaction mixture. The flask was fitted with an air-cooled condenser, then the mixture was stirred and heated at 80° C., while under an inert (N$_2$) atmosphere for 30 min. The reaction was stopped at this point and the mixture was removed from the heating bath and allowed to cool to rt. The reaction mixture was cooled to 0° C. DIPEA (0.5 mL) was added slowly into the mixture. Then a mixture of (2R,5S)-1-Boc-2,5-dimethylpiperazine (0.435 g, 2.03 mmol) in acetonitrile (5 mL) was added slowly into the reaction mixture. The ice bath was removed and the overall mixture was allowed to slowly warm to rt over 10 min. The reaction mixture was concentrated in vacuo. The crude material was adsorbed onto a plug of silica gel and purified by silica gel chromatography (eluent: 0-50% EtOAc/heptane) to afford (2R,5S)-tert-butyl-4-(6,7-dichloro-1-(4,6-diisopropylpyrimidin-5-yl)-2-oxo-1,2-dihydropyrido[2,3-d]pyrimidin-4-yl)-2,5-dimethylpiperazine-1-carboxylate (0.402 g, 0.681 mmol, 67.1% yield) as a light-yellow solid. m/z (ESI, +ve ion): 590.2 (M+H)$^+$.

Step 5: (2R,5S)-tert-Butyl 4-(6-chloro-1-(4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate. To a 100-mL round-bottomed flask was added tert-butyl (2R,5S)-4-(6,7-dichloro-1-(4,6-diisopropylpyrimidin-5-yl)-2-oxo-1,2-dihydropyrido[2,3-d]pyrimidin-4-yl)-2,5-dimethylpiperazine-1-carboxylate (Intermediate K, 0.250 g, 0.423 mmol) and KOAc (0.125 g, 1.27 mmol) in 1,4-dioxane (2.12 mL). The reaction mixture was degassed by bubbling $N_2$ into the mixture for 5 min. Then (1,1'-bis (diphenylphosphino)ferrocene)dichloropalladium (0.031 g, 0.042 mmol), followed by 2-fluorophenylboronic acid (0.118 g, 0.847 mmol) and water (0.3 mL) were added into the reaction mixture. The mixture was stirred and heated at 90° C. for 15 min. The reaction mixture was diluted with sat. aq. ammonium chloride and EtOAc. The layers were separated and the aqueous layer was extracted with EtOAc. The combined organic extracts were dried over $Mg_2SO_4$, filtered and concentrated in vacuo. The crude material was adsorbed onto a plug of silica gel and purified by silica gel chromatography (eluent: 0-100% EtOAc/heptane) to provide (2R, 5S)-tert-butyl-4-(6-chloro-1-(4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.245 g, 0.377 mmol, 89% yield) as a light-yellow solid. m/z (ESI, +ve ion): 650.3 (M+H)$^+$.

Step 6: 4-((2S,5R)-4-Acryloyl-2,5-dimethylpiperazin-1-yl)-6-chloro-1-(4,6-diisopropylpyrimidin-5-yl)-7-(2-fluorophenyl)pyrido[2,3-d]pyrimidin-2(1H)-one. To a 100-mL round-bottomed flask was added tert-butyl (2R,5S)-4-(6-chloro-1-(4,6-diisopropylpyrimidin-5-yl)-7-(2-fluorophenyl)-2-oxo-1,2-dihydropyrido[2,3-d]pyrimidin-4-yl)-2,5-dimethylpiperazine-1-carboxylate (0.235 g, 0.361 mmol) and trifluoroacetic acid (0.269 mL, 3.61 mmol) in DCM (3.61 mL). The reaction mixture was stirred and heated at 38° C. for 2.5 h, while under an inert ($N_2$) atmosphere. The reaction mixture was concentrated in vacuo to provide crude 6-chloro-1-(4,6-diisopropylpyrimidin-5-yl)-4-((2S,5R)-2,5-dimethylpiperazin-1-yl)-7-(2-fluorophenyl)pyrido[2,3-d]pyrimidin-2(1H)-one that was carried directly into the next step of the synthesis, without further purification.

6-Chloro-1-(4,6-diisopropylpyrimidin-5-yl)-4-((2S,5R)-2,5-dimethylpiperazin-1-yl)-7-(2-fluorophenyl)pyrido[2,3-d]pyrimidin-2(1H)-one was dissolved in dichloromethane (3.61 mL), and the mixture was cooled to 0° C. DIPEA (0.758 mL, 4.34 mmol) was added into the reaction mixture and the mixture was allowed to stir 2 min. Acryloyl chloride (0.029 mL, 0.361 mmol) was added dropwise into the mixture. The mixture was diluted with EtOAc and sat. aq. $NaHCO_3$, and the layers were separated. The aqueous layer was extracted with EtOAc. The combined organic extracts were dried over $MgSO_4$, filtered and concentrated in vacuo. The crude material was adsorbed onto a plug of silica gel and purified by silica gel chromatography (eluent: 0-5% MeOH/DCM) to afford 4-((2S,5R)-4-acryloyl-2,5-dimethylpiperazin-1-yl)-6-chloro-1-(4,6-diisopropylpyrimidin-5-yl)-7-(2-fluorophenyl)pyrido[2,3-d]pyrimidin-2(1H)-one (0.110 g, 0.182 mmol, 50.4% yield) as a white solid. $^1$H NMR (400 MHz, DMSO-$d_6$) δ ppm 9.07 (s, 1H) 8.50 (d, J=4.98 Hz, 1H) 7.49-7.56 (m, 1H) 7.26-7.35 (m, 2H) 7.20 (t, J=6.91 Hz, 1H) 6.78-6.91 (m, 1H) 6.20 (br d, J=17.21 Hz, 1H) 5.73-5.79 (m, 1H) 4.89 (br s, 1H) 4.79 (br s, 1H) 4.14-4.28 (m, 1H) 4.08 (br d, J=5.18 Hz, 1H) 3.88 (br t, J=13.58 Hz, 2H) 3.16-3.28 (m, 2H) 2.66-2.80 (m, 2H) 1.32-1.39 (m, 3H) 1.19-1.22 (m, 1H) 1.09 (dd, J=6.63, 2.70 Hz, 6H) 0.95 (br d, J=6.43 Hz, 6H). m/z (ESI, +ve ion): 604.4 (M+H)$^+$.

Example 8

4-((2S,5R)-4-Acryloyl-2,5-dimethylpiperazin-1-yl)-6-chloro-1-(4,6-diisopropylpyrimidin-5-yl)-7-(2-fluoro-6-hydroxyphenyl)pyrido[2,3-d]pyrimidin-2(1H)-one

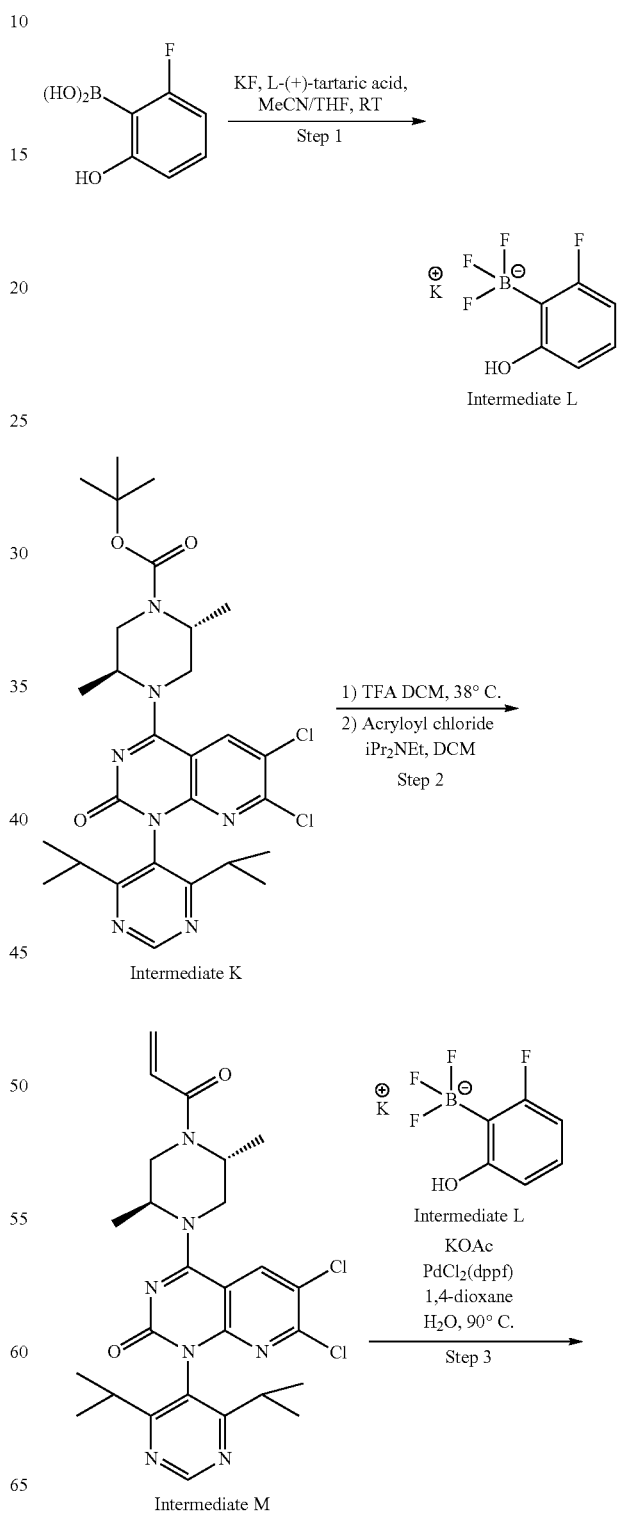

-continued

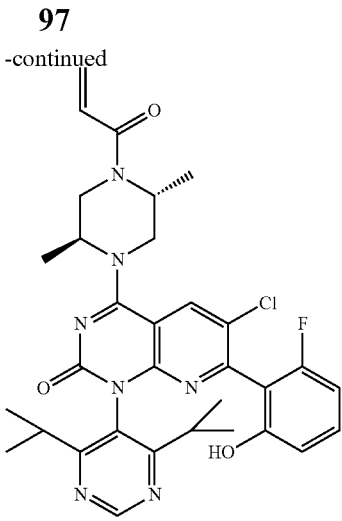

Step 1: (2-Fluoro-6-hydroxyphenyl)potassium trifluoroborate (Intermediate L)

A solution of potassium fluoride (44.7 g, 770 mmol) in water (75 mL) was added to a suspension of (2-fluoro-6-hydroxyphenyl)boronic acid (30 g, 192 mmol, Combi-Blocks, San Diego, Calif.) in acetonitrile (750 mL). The mixture was stirred for 2 min and then a solution of L-(+)-tartaric acid (72.2 g, 481 mmol) in THF (375 mL) was added over a 10 min period via addition funnel. The mixture was stirred vigorously with a mechanical stirrer for 1 h, and the resulting suspension was filtered, and the filtered solids were washed with a small amount of THF. The solids were discarded and the filtrate was partially concentrated until solids started to precipitate out of solution. The mixture was then cooled to −20° C. and stirred for 16 h. The reaction was slowly warmed and 2-propanol (20 mL) was added. The resulting suspension was filtered and the filtered solids were washed with 2-propanol. The filtrate was again partially concentrated until a suspension formed and then was cooled to −20° C. and stirred for an additional 20 min. The resulting suspension was diluted with 2-propanol and filtered, and the filtered solids were washed with 2-propanol. The two batches of solids were combined to provide 2-fluoro-6-hydroxyphenyl)potassium trifluoroborate. $^{1}$H NMR (400 MHz, DMSO-$d_6$) δ ppm 8.07 (q, J=14.7 Hz, 1H) 6.93 (q, J=7.5 Hz, 1H) 6.30-6.38 (m, 2H).

Step 2: 4-((2S,5R)-4-Acryloyl-2,5-dimethylpiperazin-1-yl)-6,7-dichloro-1-(4,6-diisopropylpyrimidin-5-yl)pyrido[2,3-d]pyrimidin-2(1H)-one (Intermediate M)

To a 100-mL round-bottomed flask was added tert-butyl (2R,5S)-4-(6,7-dichloro-1-(4,6-diisopropylpyrimidin-5-yl)-2-oxo-1,2-dihydropyrido[2,3-d]pyrimidin-4-yl)-2,5-dimethylpiperazine-1-carboxylate (Intermediate K, 0.479 g, 0.811 mmol) and trifluoroacetic acid (1.21 mL, 16.2 mmol) in 1,2-dichloroethane (4.06 mL). The reaction mixture was stirred and heated at 70° C. for 1 h, while under an inert (N$_2$) atmosphere. The reaction mixture was concentrated in vacuo to provide crude 6,7-dichloro-1-(4,6-diisopropylpyrimidin-5-yl)-4-((2S,5R)-2,5-dimethylpiperazin-1-yl)pyrido[2,3-d]pyrimidin-2(1H)-one that was carried directly into the next step of the synthesis, without further purification.

6,7-Dichloro-1-(4,6-diisopropylpyrimidin-5-yl)-4-((2S,5R)-2,5-dimethylpiperazin-1-yl)pyrido[2,3-d]pyrimidin-2(1H)-one was diluted with DCM (4 mL), then the reaction mixture was cooled to 0° C. DIPEA (1.70 mL, 9.73 mmol) was added into the reaction mixture and the mixture was allowed to stir for 2 min. Acryloyl chloride (0.066 mL, 0.811 mmol) was added dropwise into the reaction mixture. The mixture was diluted with DCM and sat. aq. NaHCO$_3$, then the layers were separated. The aqueous layer was extracted with DCM. The combined organic extracts were dried over MgSO$_4$, filtered and concentrated in vacuo. The crude material was adsorbed onto a plug of silica gel and purified by silica gel chromatography (eluent: 0-100% EtOAc/heptane, then with a gradient of 0-5% MeOH/DCM) to afford 4-((2S,5R)-4-acryloyl-2,5-dimethylpiperazin-1-yl)-6,7-dichloro-1-(4,6-diisopropylpyrimidin-5-yl)pyrido[2,3-d]pyrimidin-2(1H)-one (0.397 g, 0.729 mmol, 90% yield) as tan solid. m/z (ESI, +ve ion): 544.1 (M+H)$^{+}$.

Step 3: 4-((2S,5R)-4-Acryloyl-2,5-dimethylpiperazin-1-yl)-6-chloro-1-(4,6-diisopropylpyrimidin-5-yl)-7-(2-fluoro-6-hydroxyphenyl)pyrido[2,3-d]pyrimidin-2(1H)-one To a 100-mL round-bottomed flask was added 4-((2S,5R)-4-acryloyl-2,5-dimethylpiperazin-1-yl)-6,7-dichloro-1-(4,6-diisopropylpyrimidin-5-yl)pyrido[2,3-d]pyrimidin-2(1H)-one (Intermediate M, 0.152 g, 0.279 mmol) and KOAc (0.082 g, 0.837 mmol) in 1,4-dioxane (1.40 mL). The reaction mixture was de-gassed by bubbling argon into the mixture for 5 min. Then (1,1'-bis(diphenylphosphino)ferrocene)dichloropalladium (0.020 g, 0.028 mmol) was added into the mixture. The mixture was stirred and heated at 90° C. for 10 min. Then a mixture of potassium trifluoro(2-fluoro-6-hydroxyphenyl)borate (Intermediate L, 0.183 g, 0.837 mmol) in 1,4-dioxane (1 mL) was added slowly into the reaction mixture, followed by water (0.8 mL). The reaction mixture was stirred and heated at 90° C. for 1 h. The crude material was adsorbed onto a plug of silica gel and purified by silica gel chromatography (eluent: 0-5% MeOH/DCM) to provide 4-((2S,5R)-4-acryloyl-2,5-dimethylpiperazin-1-yl)-6-chloro-1-(4,6-diisopropylpyrimidin-5-yl)-7-(2-fluoro-6-hydroxyphenyl)pyrido[2,3-d]pyrimidin-2(1H)-one (0.115 g, 0.185 mmol, 66.4% yield) as an off-white solid. $^{1}$H NMR (400 MHz, DMSO-$d_6$) δ ppm 10.12 (br d, J=13.27 Hz, 1H) 9.05 (s, 1H) 8.48 (br s, 1H) 7.20-7.28 (m, 1H) 6.84 (td, J=17.52, 10.57 Hz, 1H) 6.64-6.75 (m, 2H) 6.20 (dd, J=16.69, 2.18 Hz, 1H) 5.73-5.80 (m, 1H) 4.75-4.98 (m, 2H) 4.14-4.30 (m, 1H) 3.80-3.95 (m, 2H) 3.39-3.54 (m, 1H) 2.56-2.78 (m, 2H) 1.19-1.39 (m, 6H) 1.03-1.15 (m, 6H) 0.95 (br s, 6H). m/z (ESI, +ve ion): 620.0 (M+H)$^{+}$.

Example 9

4-((2S,5R)-4-Acryloyl-2,5-dimethylpiperazin-1-yl)-7-(2-amino-6-fluorophenyl)-6-chloro-1-(4,6-diisopropylpyrimidin-5-yl)pyrido[2,3-d]pyrimidin-2(1H)-one

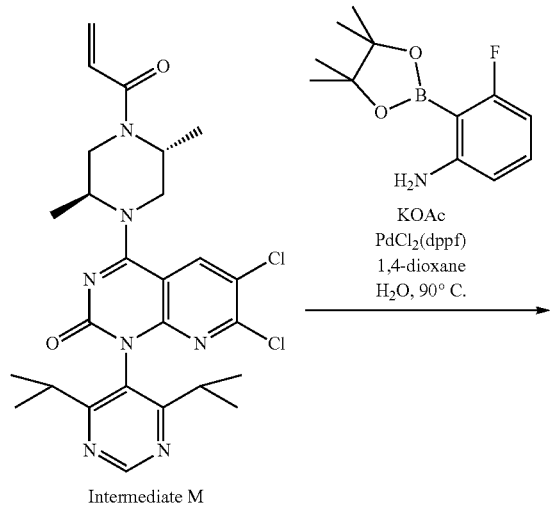

4-((2S,5R)-4-Acryloyl-2,5-dimethylpiperazin-1-yl)-7-(2-amino-6-fluorophenyl)-6-chloro-1-(4,6-diisopropylpyrimidin-5-yl)pyrido[2,3-d]pyrimidin-2(1H)-one. To a 100-mL round-bottomed flask was added 4-((2S,5R)-4-acryloyl-2,5-dimethylpiperazin-1-yl)-6,7-dichloro-1-(4,6-diisopropylpyrimidin-5-yl)pyrido[2,3-d]pyrimidin-2(1H)-one (Intermediate M, 0.230 g, 0.422 mmol) and KOAc (0.124 g, 1.27 mmol) in 1,4-dioxane (2.11 mL). The reaction mixture was de-gassed by bubbling argon into the mixture for 5 min. Then (1,1'-bis(diphenylphosphino)ferrocene)dichloropalladium (0.031 g, 0.042 mmol) was added into the mixture. The mixture was stirred and heated at 90° C. for 10 min. Then a mixture of (2-amino-6-fluorophenyl)boronic acid pinacol ester (0.200 g, 0.845 mmol, CombiPhos, Trenton, N.J.) in 1,4-dioxane (1 mL) was added slowly into the reaction mixture, followed by 6 drops of water. The overall reaction mixture was stirred and heated at 90° C. for 1 h. The crude material was adsorbed onto a plug of silica gel and purified by silica gel chromatography (eluent: 0-5% MeOH/DCM) to provide 4-((2S,5R)-4-acryloyl-2,5-dimethylpiperazin-1-yl)-7-(2-amino-6-fluorophenyl)-6-chloro-1-(4,6-diisopropylpyrimidin-5-yl)pyrido[2,3-d]pyrimidin-2(1H)-one (0.155 g, 0.250 mmol, 59.3% yield) as a yellow solid. $^1$H NMR (400 MHz, DMSO-$d_6$) δ ppm 9.05 (s, 1H) 8.45-8.49 (m, 1H) 7.00-7.09 (m, 1H) 6.78-6.91 (m, 1H) 6.44 (d, J=8.29 Hz, 1H) 6.31 (q, J=9.12 Hz, 1H) 6.19 (dd, J=16.59, 2.07 Hz, 1H) 5.72-5.79 (m, 1H) 5.11 (br d, J=11.40 Hz, 2H) 4.72-4.95 (m, 2H) 4.09-4.24 (m, 1H) 3.82-4.01 (m, 2H) 3.44-3.61 (m, 1H) 2.78-2.94 (m, 1H) 2.53-2.68 (m, 1H) 1.17-1.37 (m, 6H) 1.07 (s, 6H) 0.87-1.03 (m, 6H). m/z (ESI, +ve ion): 619.2 (M+H)$^+$.

Example 10

4-((2S,5R)-4-Acryloyl-2,5-dimethylpiperazin-1-yl)-1-(4,6-diisopropylpyrimidin-5-yl)-6-fluoro-7-(2-fluorophenyl)pyrido[2,3-d]pyrimidin-2(1H)-one

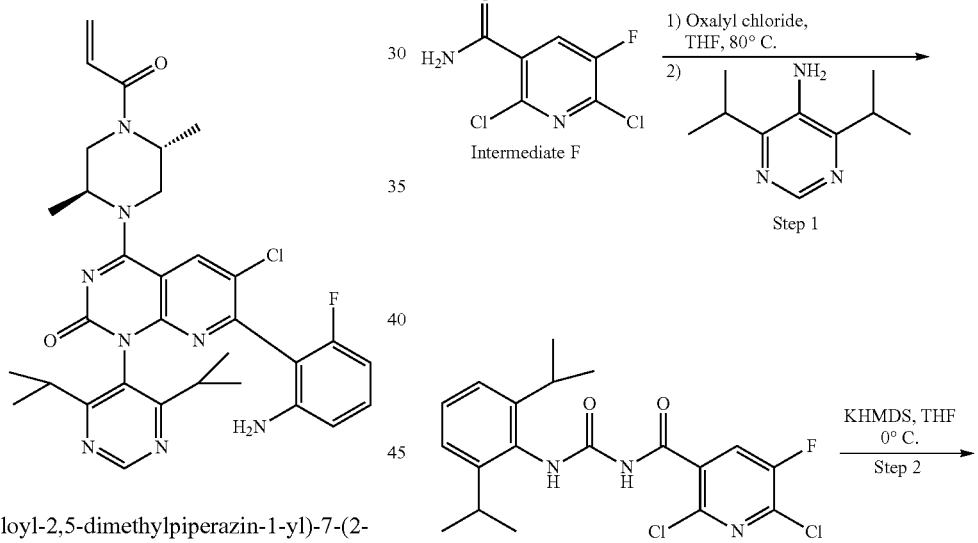

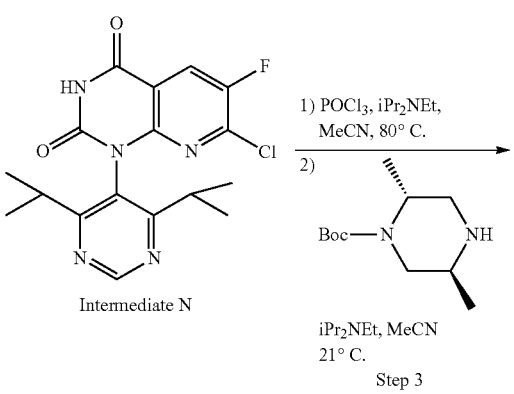

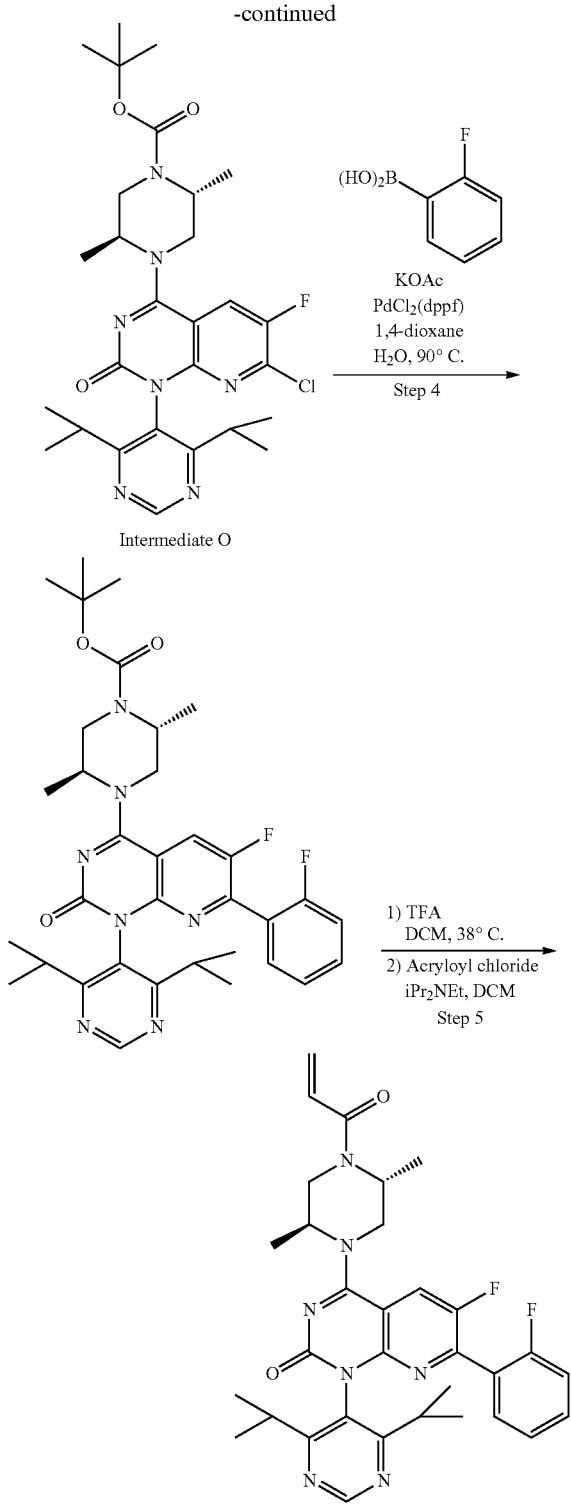

Step 1: 2,6-Dichloro-N-((4,6-diisopropylpyrimidin-5-yl)carbamoyl)-5-fluoronicotinamide To a 250-mL round-bottomed flask was added 2,6-dichloro-5-fluoronicotinamide (Intermediate F, 4.45 g, 21.3 mmol) and oxalyl chloride (16.0 mL, 31.9 mmol) in THF (71.0 mL). The flask was fitted with an air-cooled condenser, and the mixture was stirred and heated at 80° C. for 1 h. The reaction mixture was concentrated in vacuo to provide (2,6-dichloro-5-fluoronicotinoyl)carbamic chloride that was carried into the next step of the synthesis, without further purification.

To a 250-mL round-bottomed flask was added (2,6-dichloro-5-fluoronicotinoyl)carbamoyl isocyanate (crude material from previous step) in tetrahydrofuran (71.0 mL). Then a solution of 4,6-diisopropylpyrimidin-5-amine (4.01 g, 22.4 mmol) in THF (10 mL) was added dropwise into the reaction mixture. The mixture was allowed to stir under an inert (N₂) atmosphere, while at rt for 1.5 h. The reaction mixture was concentrated in vacuo. The crude material was adsorbed onto a plug of silica gel and purified by silica gel chromatography (eluent: 0-40% EtOAc/heptane) to afford 2,6-dichloro-N-((4,6-diisopropylpyrimidin-5-yl)carbamoyl)-5-fluoronicotinamide (7.74 g, 18.7 mmol, 88% yield) as a light-yellow solid. $^1$H NMR (400 MHz, DMSO-d₆) δ ppm 11.41 (br s, 1H) 9.66 (br s, 1H) 8.99 (s, 1H) 8.54 (br d, J=7.88 Hz, 1H) 3.20-3.28 (m, 2H) 1.17 (d, J=6.84 Hz, 12H). m/z (ESI, +ve ion): 414.0 (M+H)⁺.

Step 2: 7-Chloro-1-(4,6-diisopropylpyrimidin-5-yl)-6-fluoropyrido[2,3-d]pyrimidine-2,4(1H,3H)-dione (Intermediate N)

To a 250-mL round-bottomed flask was added 2,6-dichloro-N-((4,6-diisopropylpyrimidin-5-yl)carbamoyl)-5-fluoronicotinamide (4.00 g, 9.66 mmol) in THF (48.3 mL). The reaction mixture was cooled to 0° C. in a wet ice/water bath. Then potassium bis(trimethylsilyl)amide, 1 M solution in THF (12.1 mL, 12.1 mmol) was added via an addition funnel dropwise into the reaction mixture over 5 min. The ice bath was removed and the reaction mixture was allowed to slowly warm to rt, while stirring under an inert (N₂) atmosphere for 1 h. More KHMDS (0.5 equiv; 6 mL) was added dropwise into the reaction mixture, until the starting material was mostly consumed. The reaction mixture was quenched with sat. aq. ammonium chloride (50 mL), then the mixture was diluted with EtOAc-MeOH (3:1) and brine solution. The layers were separated and the aqueous layer was extracted with EtOAc. The combined organic extracts were dried over MgSO₄, filtered and concentrated in vacuo to afford 7-chloro-1-(4,6-diisopropylpyrimidin-5-yl)-6-fluoropyrido[2,3-d]pyrimidine-2,4(1H,3H)-dione (2.58 g, 6.84 mmol, 70.9% yield) as a tan solid. $^1$H NMR (400 MHz, DMSO-d₆) δ ppm 12.03-12.52 (m, 1H) 8.97-9.23 (m, 1H) 8.25-8.58 (m, 1H) 2.80 (dt, J=13.22, 6.56 Hz, 2H) 0.96 (d, J=6.63 Hz, 6H) 0.85 (d, J=6.63 Hz, 6H). m/z (ESI, +ve ion): 378.0 (M+H)⁺.

Step 3: (2R,5S)-tert-Butyl 4-(7-chloro-1-(4,6-diisopropylpyrimidin-5-yl)-6-fluoro-2-oxo-1,2-dihydropyrido[2,3-d]pyrimidin-4-yl)-2,5-dimethylpiperazine-1-carboxylate (Intermediate O)

To a 100-mL round-bottomed flask was added 7-chloro-1-(4,6-diisopropylpyrimidin-5-yl)-6-fluoropyrido[2,3-d]pyrimidine-2,4(1H,3H)-dione (Intermediate N, 0.300 g, 0.794 mmol) and DIPEA (0.180 mL, 1.03 mmol) in acetonitrile (7.94 mL). Then phosphorous oxychloride (0.089 mL, 0.953 mmol) was added slowly into the reaction mixture. The flask was fitted with an air-cooled condenser and the mixture was stirred and heated at 80° C., while under an inert (N₂) atmosphere for 45 min. The reaction mixture was removed from the heat bath and allowed to cool to rt. The reaction mixture was cooled to 0° C. Then DIPEA (0.5 mL) was added slowly into the reaction mixture. Then a mixture of (2R,5S)-1-Boc-2,5-dimethylpiperazine (0.213 g, 0.993 mmol) in acetonitrile (1 mL) was added slowly into the reaction mixture. The ice bath was removed and the overall mixture was allowed to slowly warm to rt over 1 h. The mixture was diluted with EtOAc and the layers were separated. The aqueous layer was extracted with EtOAc and brine. The combined organic extracts were dried over MgSO$_4$, filtered and concentrated in vacuo. The crude material was adsorbed onto a plug of silica gel and purified by silica gel chromatography (eluent: 0-100% EtOAc/heptane) to afford tert-butyl (2R,5S)-4-(7-chloro-1-(4,6-diisopropylpyrimidin-5-yl)-6-fluoro-2-oxo-1,2-dihydropyrido[2,3-d]pyrimidin-4-yl)-2,5-dimethylpiperazine-1-carboxylate (0.247 g, 0.430 mmol, 54.2% yield) as a tan solid. $^1$H NMR (400 MHz, DMSO-d$_6$) δ ppm 9.15 (s, 1H) 8.39 (d, J=8.29 Hz, 1H) 5.14 (t, J=5.81 Hz, 1H) 4.49 (d, J=5.80 Hz, 3H) 4.06 (br d, J=13.89 Hz, 1H) 3.66 (br s, 1H) 2.66-2.72 (m, 2H) 1.44 (s, 9H) 1.31 (d, J=6.63 Hz, 3H) 1.10-1.14 (m, 3H) 1.09 (s, 6H) 0.98-1.04 (m, 6H). m/z (ESI, +ve ion): 574.2 (M+H)$^+$.

Step 4: (2R,5S)-tert-Butyl 4-(1-(4,6-diisopropylpyrimidin-5-yl)-6-fluoro-7-(2-fluorophenyl)-2-oxo-1,2-dihydropyrido[2,3-d]pyrimidin-4-yl)-2,5-dimethylpiperazine-1-carboxylate To a 100-mL round-bottomed flask was added tert-butyl (2R,5S)-4-(7-chloro-1-(4,6-diisopropylpyrimidin-5-yl)-6-fluoro-2-oxo-1,2-dihydropyrido[2,3-d]pyrimidin-4-yl)-2,5-dimethylpiperazine-1-carboxylate (Intermediate O, 0.225 g, 0.392 mmol) and KOAc (0.115 g, 1.18 mmol) in 1,4-dioxane (2.54 mL). The reaction mixture was de-gassed by bubbling N$_2$ into the mixture for 5 min. Then (1,1'-bis(diphenylphosphino) ferrocene) dichloropalladium (0.029 g, 0.039 mmol), followed by 2-fluorophenylboronic acid (0.066 g, 0.470 mmol) and water (0.1 mL) were added into the reaction mixture. The mixture was stirred and heated at 80° C. for 45 min. The reaction mixture was diluted with sat. aq. ammonium chloride and EtOAc. The layers were separated and the aqueous layer was extracted with EtOAc. The combined organic extracts were dried over MgSO$_4$, filtered and concentrated in vacuo. The crude material was adsorbed onto a plug of silica gel and purified by silica gel chromatography (eluent: 0-100% EtOAc/heptane) to afford tert-butyl (2R,5S)-4-(1-(4,6-diisopropylpyrimidin-5-yl)-6-fluoro-7-(2-fluorophenyl)-2-oxo-1,2-dihydropyrido[2,3-d]pyrimidin-4-yl)-2,5-dimethylpiperazine-1-carboxylate (0.225 g, 0.355 mmol, 91% yield) as a tan solid. $^1$H NMR (400 MHz, DMSO-d$_6$) δ ppm 9.09 (s, 1H) 8.34 (d, J=9.54 Hz, 1H) 7.55 (br d, J=7.46 Hz, 1 H) 7.22-7.25 (m, 3H) 4.85 (br s, 1H) 4.27-4.40 (m, 1H) 4.16 (br d, J=14.10 Hz, 1H) 3.71 (br d, J=13.48 Hz, 2H) 3.46-3.61 (m, 1H) 2.68-2.77 (m, 2H) 1.45 (s, 9H) 1.34 (d, J=6.63 Hz, 3H) 1.18 (br d, J=6.22 Hz, 3H) 1.09 (s, 6H) 0.94 (d, J=6.63 Hz, 6H). m/z (ESI, +ve ion): 634.4 (M+H)$^+$.

Step 5: 4-((2S,5R)-4-Acryloyl-2,5-dimethylpiperazin-1-yl)-1-(4,6-diisopropylpyrimidin-5-yl)-6-fluoro-7-(2-fluorophenyl)pyrido[2,3-d]pyrimidin-2(1H)-one To a 100-mL round-bottomed flask was added tert-butyl (2R,5S)-4-(1-(4,6-diisopropylpyrimidin-5-yl)-6-fluoro-7-(2-fluorophenyl)-2-oxo-1,2-dihydropyrido[2,3-d]pyrimidin-4-yl)-2,5-dimethylpiperazine-1-carboxylate (0.225 g, 0.355 mmol) and trifluoroacetic acid (0.265 mL, 3.55 mmol) in DCM (3.37 mL). The reaction mixture was stirred and heated at 38° C. for 2.5 h, while under an inert (N$_2$) atmosphere. The reaction mixture was concentrated in vacuo to provide 1-(4,6-diisopropylpyrimidin-5-yl)-4-((2S,5R)-2,5-dimethylpiperazin-1-yl)-6-fluoro-7-(2-fluorophenyl)pyrido[2,3-d]pyrimidin-2(1H)-one. This material was carried directly into the next step of the synthesis, without further purification.

The crude 1-(4,6-diisopropylpyrimidin-5-yl)-4-((2S,5R)-2,5-dimethylpiperazin-1-yl)-6-fluoro-7-(2-fluorophenyl)pyrido[2,3-d]pyrimidin-2(1H)-one was diluted with dichloromethane (3.37 mL) and cooled to 0° C. Then N,N-diisopropylethylamine (0.744 mL, 4.26 mmol) was added into the reaction mixture, and the mixture was allowed to stir for 2 min. Acryloyl chloride (0.029 mL, 0.355 mmol) was added dropwise into the reaction mixture and it was allowed to stir under an inert (N$_2$) atmosphere for 30 min. The mixture was diluted with DCM and sat. aq. NaHCO$_3$, then the layers were separated. The aqueous layer was extracted with DCM. The combined organic extracts were dried over MgSO$_4$, filtered and concentrated in vacuo. The crude material was adsorbed onto a plug of silica gel and purified by silica gel chromatography (eluent: 0-5% MeOH/DCM) to afford 4-((2S,5R)-4-acryloyl-2,5-dimethylpiperazin-1-yl)-1-(4,6-diisopropylpyrimidin-5-yl)-6-fluoro-7-(2-fluorophenyl)pyrido[2,3-d]pyrimidin-2(1H)-one (0.070 g, 0.119 mmol, 33.5% yield) as a tan solid. 1H NMR (400 MHz, DMSO-d$_6$) δ ppm 9.03 (s, 1H) 8.30 (dd, J=9.43, 4.87 Hz, 1H) 7.48 (q, J=6.98 Hz, 1H) 7.16-7.30 (m, 3H) 6.71-6.84 (m, 1H) 6.12 (br d, J=17.00 Hz, 1H) 5.69 (br d, J=10.16 Hz, 1H) 4.67-4.89 (m, 2H) 4.06-4.19 (m, 1H) 3.74-3.85 (m, 2H) 2.65 (dq, J=12.75, 6.39 Hz, 2H) 1.27 (t, J=5.91 Hz, 3H) 1.19 (br d, J=6.63 Hz, 2H) 1.12 (d, J=6.63 Hz, 2H) 1.02 (dd, J=6.63, 1.87 Hz, 6H) 0.87 (d, J=6.63 Hz, 6H). m/z (ESI, +ve ion): 588.2 (M+H)$^+$.

Example 11

4-((2S,5R)-4-Acryloyl-2,5-dimethylpiperazin-1-yl)-1-(4,6-diisopropylpyrimidin-5-yl)-6-fluoro-7-(2-fluoro-6-hydroxyphenyl)pyrido[2,3-d]pyrimidin-2(1H)-one

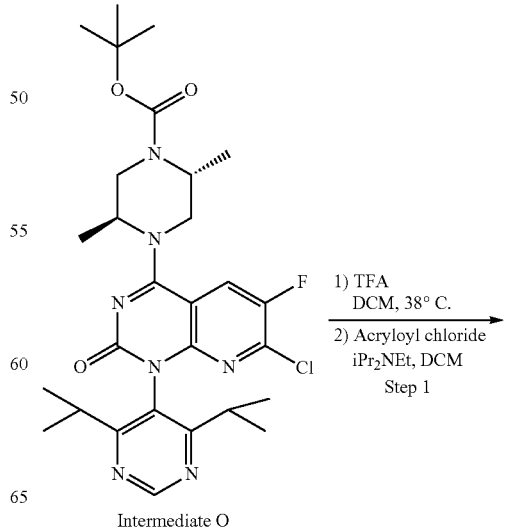

Intermediate O

-continued

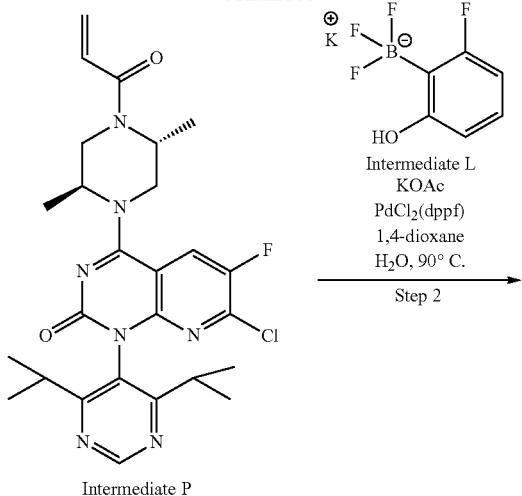

Intermediate P

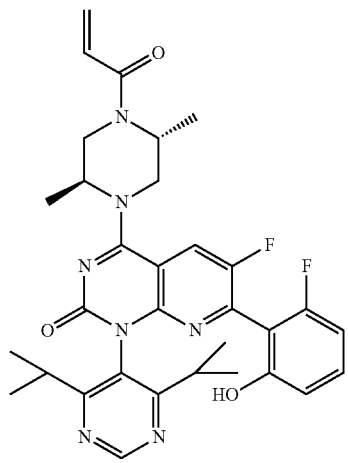

Step 1: 4-((2S,5R)-4-Acryloyl-2,5-dimethylpiperazin-1-yl)-7-chloro-1-(4,6-diisopropylpyrimidin-5-yl)-6-fluoropyrido[2,3-d]pyrimidin-2(1H)-one (Intermediate P)

To a 100-mL round-bottomed flask was added tert-butyl (2R,5S)-4-(7-chloro-1-(4,6-diisopropylpyrimidin-5-yl)-6-fluoro-2-oxo-1,2-dihydropyrido[2,3-d]pyrimidin-4-yl)-2,5-dimethylpiperazine-1-carboxylate (Intermediate O, 0.590 g, 1.03 mmol) and trifluoroacetic acid (1.53 mL, 20.5 mmol) in DCM (3.37 mL). The reaction mixture was stirred and heated at 38° C. for 16 h, while under an inert (N$_2$) atmosphere. The reaction mixture was concentrated in vacuo to provide 7-chloro-1-(4,6-diisopropylpyrimidin-5-yl)-4-((2S,5R)-2,5-dimethylpiperazin-1-yl)-6-fluoropyrido[2,3-d]pyrimidin-2(1H)-one. This material was carried directly into the next step of the synthesis without further purification.

The crude 7-chloro-1-(4,6-diisopropylpyrimidin-5-yl)-4-((2S,5R)-2,5-dimethylpiperazin-1-yl)-6-fluoropyrido[2,3-d]pyrimidin-2(1H)-one was diluted with DCM (3.37 mL), and the reaction mixture was cooled to 0° C. DIPEA (2.15 mL, 12.3 mmol) was added into the reaction mixture and the mixture was allowed to stir for 2 min. Acryloyl chloride (0.084 mL, 1.03 mmol) was added dropwise into the reaction mixture. The mixture was diluted with DCM and sat. aq. NaHCO$_3$, and the layers were separated. The aqueous layer was extracted with DCM. The combined organic extracts were dried over MgSO$_4$, filtered and concentrated in vacuo. The crude material was adsorbed onto a plug of silica gel and purified by silica gel chromatography (eluent: 0-100% EtOAc/heptane, followed by a gradient of 0-5% MeOH/DCM) to afford 4-((2S,5R)-4-acryloyl-2,5-dimethylpiperazin-1-yl)-7-chloro-1-(4,6-diisopropylpyrimidin-5-yl)-6-fluoropyrido[2,3-d]pyrimidin-2(1H)-one (0.472 g, 0.894 mmol, 87% yield) as a tan solid. m/z (ESI, +ve ion): 528.1 (M+H)$^+$.

Step 2: 4-((2S,5R)-4-Acryloyl-2,5-dimethylpiperazin-1-yl)-1-(4,6-diisopropylpyrimidin-5-yl)-6-fluoro-7-(2-fluoro-6-hydroxyphenyl)pyrido[2,3-d]pyrimidin-2(1H)-one To a 100-mL round-bottomed flask was added 4-((2S,5R)-4-acryloyl-2,5-dimethylpiperazin-1-yl)-7-chloro-1-(4,6-diisopropylpyrimidin-5-yl)-6-fluoropyrido[2,3-d]pyrimidin-2(1H)-one (Intermediate P, 0.210 g, 0.398 mmol) and KOAc (0.117 g, 1.19 mmol) in 1,4-dioxane (2.0 mL). The reaction mixture was de-gassed by bubbling argon into the mixture for 5 min. (1,1'-Bis(diphenylphosphino)ferrocene)dichloropalladium (0.029 g, 0.040 mmol) was added into the mixture. The mixture was stirred and heated at 90° C. for 10 min. Then potassium trifluoro(2-fluoro-6-hydroxyphenyl)borate (Intermediate L, 0.173 g, 0.795 mmol) in 1,4-dioxane (1 mL) was added slowly into the reaction mixture, followed by water (0.8 mL). The reaction mixture was stirred and heated at 90° C. for 1 h. The crude material was adsorbed onto a plug of silica gel and purified by silica gel chromatography (eluent: 0-5% MeOH in DCM) to afford 4-((2S,5R)-4-acryloyl-2,5-dimethylpiperazin-1-yl)-1-(4,6-diisopropylpyrimidin-5-yl)-6-fluoro-7-(2-fluoro-6-hydroxyphenyl)pyrido[2,3-d]pyrimidin-2(1H)-one (0.180 g, 0.298 mmol, 75.0% yield) as a light-yellow solid. $^1$H NMR (400 MHz, DMSO-d$_6$) δ ppm 10.20 (s, 1H) 9.05 (s, 1H) 8.32 (dd, J=8.91, 4.15 Hz, 1H) 7.22-7.30 (m, 1H) 6.65-6.90 (m, 3H) 6.18 (dd, J=16.59, 2.07 Hz, 1H) 5.72-5.78 (m, 1H) 4.73-4.96 (m, 2H) 4.13-4.22 (m, 1H) 3.85 (br s, 2H) 3.41-3.56 (m, 1H) 2.62-2.74 (m, 2H) 1.19-1.36 (m, 6H) 1.08 (dd, J=6.63, 1.45 Hz, 6H) 0.93 (br d, J=5.39 Hz, 6H). m/z (ESI, +ve ion): 604.1 (M+H)$^+$.

Example 12

4-((2S,5R)-4-Acryloyl-2,5-dimethylpiperazin-1-yl)-7-(2-amino-6-fluorophenyl)-1-(4,6-diisopropylpyrimidin-5-yl)-6-fluoropyrido[2,3-d]pyrimidin-2(1H)-one

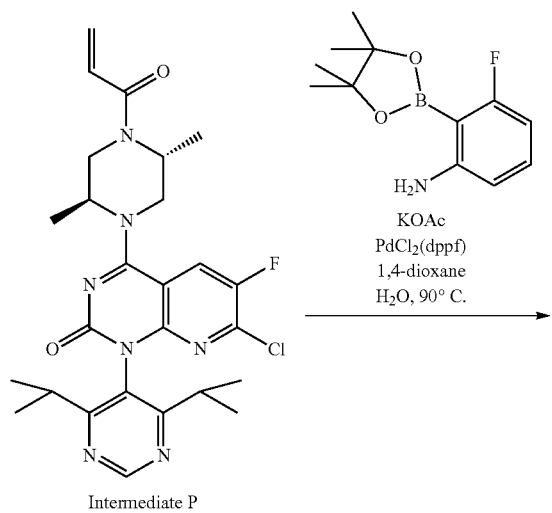

Intermediate P

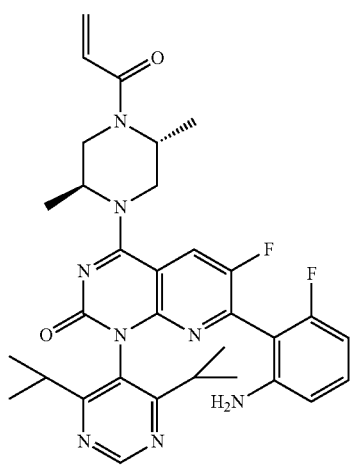

4-((2S,5R)-4-Acryloyl-2,5-dimethylpiperazin-1-yl)-7-(2-amino-6-fluorophenyl)-1-(4,6-diisopropylpyrimidin-5-yl)-6-fluoropyrido[2,3-d]pyrimidin-2(1H)-one. To a 100-mL round-bottomed flask was added 4-((2S,5R)-4-acryloyl-2,5-dimethylpiperazin-1-yl)-7-chloro-1-(4,6-diisopropylpyrimidin-5-yl)-6-fluoropyrido[2,3-d]pyrimidin-2(1H)-one (Intermediate P, 0.250 g, 0.473 mmol) and KOAc (0.139 g, 1.420 mmol) in 1,4-dioxane (2.37 mL). The reaction mixture was degassed by bubbling argon into the mixture for 5 min. Then (1,1'-bis(diphenylphosphino)ferrocene)dichloropalladium (0.035 g, 0.047 mmol) was added into the mixture. The mixture was stirred and heated at 90° C. for 10 min. Then a mixture of (2-amino-6-fluorophenyl)boronic acid pinacol ester (0.224 g, 0.947 mmol, CombiPhos, Trenton, N.J.) in 1,4-dioxane (1 mL) was added slowly into the reaction mixture, followed by 6 drops of water. The overall reaction mixture was stirred and heated at 90° C. for 1 h. The crude material was adsorbed onto a plug of silica gel and purified by silica gel chromatography (eluent: 0-5% MeOH/DCM) to afford 4-((2S,5R)-4-acryloyl-2,5-dimethylpiperazin-1-yl)-7-(2-amino-6-fluorophenyl)-1-(4,6-diisopropylpyrimidin-5-yl)-6-fluoropyrido[2,3-d]pyrimidin-2(1H)-one (0.138 g, 0.229 mmol, 48.4% yield) as a yellow solid. $^1$H NMR (400 MHz, DMSO-$d_6$) δ ppm 9.09 (s, 1H) 8.35 (br d, J=9.33 Hz, 1H) 7.07-7.14 (m, 1H) 6.78-6.92 (m, 1H) 6.48 (d, J=8.47 Hz, 1H) 6.36 (t, J=9.12 Hz, 1H) 6.20 (dd, J=16.69, 2.18 Hz, 1H) 5.73-5.80 (m, 1H) 5.31 (s, 2H) 4.76-4.94 (m, 2H) 4.15-4.22 (m, 1H) 3.82-3.91 (m, 2H) 3.45-3.57 (m, 1H) 2.67-2.79 (m, 2H) 1.30-1.37 (m, 3H) 1.18-1.29 (m, 3H) 1.05-1.09 (m, 6H) 0.95 (br d, J=6.63 Hz, 6H). m/z (ESI, +ve ion): 603.2 (M+H)$^+$.

Example 13

(M)-4-(4-Acryloyl-cis-3,5-dimethylpiperazin-1-yl)-6-chloro-7-(2-fluorophenyl)-1-(2-isopropyl-4-methylpyridin-3-yl)pyrido[2,3-d]pyrimidin-2(1H)-one

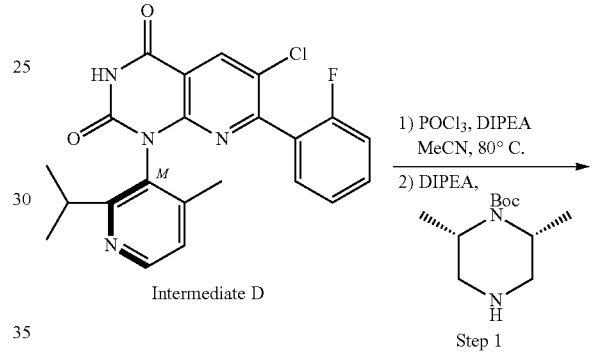

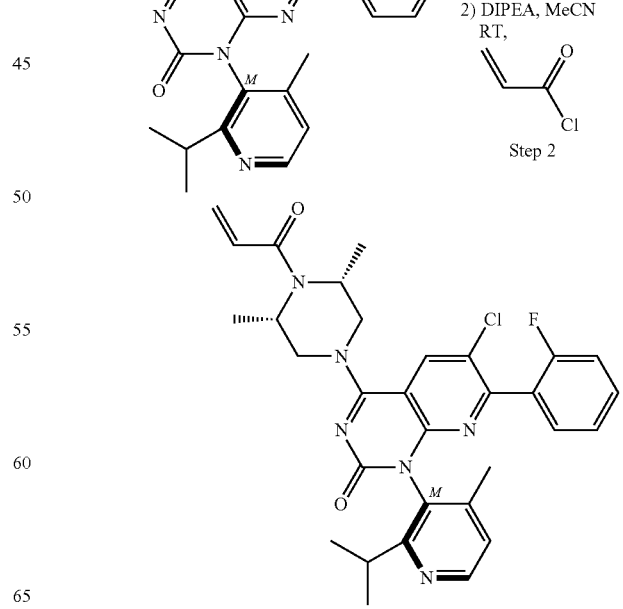

Step 1: tert-Butyl (M)-4-(6-chloro-7-(2-fluorophenyl)-1-(2-isopropyl-4-methylpyridin-3-yl)-2-oxo-1,2-dihydropyrido[2,3-d]pyrimidin-4-yl)-cis-2,6-dimethylpiperazine-1-carboxylate A solution of (M)-6-chloro-7-(2-fluorophenyl)-1-(2-isopropyl-4-methylpyridin-3-yl)pyrido[2,3-d]pyrimidine-2,4 (1H,3H)-dione (Intermediate D, 0.143 g, 0.337 mmol), phosphoryl trichloride (0.038 mL, 0.40 mmol), and DIPEA (0.176 mL, 1.01 mmol) in acetonitrile (0.8 mL) was stirred at 80° C. for 30 min. The reaction mixture was removed from the heating block, and tert-butyl cis-2,6-dimethylpiperazine-1-carboxylate (0.072 g, 0.337 mmol; Enamine, Monmouth Jct., N.J.) and DIPEA (0.176 mL, 1.01 mmol) were added. The reaction mixture was stirred at RT for 15 min. The reaction mixture was diluted with EtOAc (100 mL), added to a separatory funnel, and washed with saturated aqueous NaHCO$_3$(2×75 mL). The organic layer was separated, dried over anhydrous Na$_2$SO$_4$, and concentrated in vacuo. The crude product was adsorbed onto silica and was purified by silica gel chromatography (eluent: 0-70% EtOAc/EtOH (3:1)/heptane) to give tert-butyl (M)-4-(6-chloro-7-(2-fluorophenyl)-1-(2-isopropyl-4-methylpyridin-3-yl)-2-oxo-1,2-dihydropyrido[2,3-d]pyrimidin-4-yl)-cis-2,6-dimethylpiperazine-1-carboxylate as an amber oil. $^1$H NMR (400 MHz, CDCl$_3$) δ 8.45-8.52 (m, 1H) 8.34 (s, 1H) 7.41 (br d, J=6.6 Hz, 1H) 7.04-7.20 (m, 4H) 4.45 (br s, 2H) 4.31 (br d, J=13.3 Hz, 2H) 3.54 (br d, J=13.3 Hz, 2H) 2.74 (dt, J=13.1, 6.5 Hz, 1H) 2.04 (s, 3H) 1.53 (s, 9H) 1.25-1.32 (m, 6H) 1.23 (br d, J=6.8 Hz, 3H) 1.06 (br d, J=6.6 Hz, 3H). $^{19}$F NMR (377 MHz, CDCl$_3$) δ -112.61 (s, 1F). m/z (ESI, +ve ion): 621.0 (M+H)$^+$.

Step 2: (M)-4-(4-Acryloyl-cis-3,5-dimethylpiperazin-1-yl)-6-chloro-7-(2-fluorophenyl)-1-(2-isopropyl-4-methylpyridin-3-yl)pyrido[2,3-d]pyrimidin-2(1H)-one A solution of tert-butyl (M)-4-(6-chloro-7-(2-fluorophenyl)-1-(2-isopropyl-4-methylpyridin-3-yl)-2-oxo-1,2-dihydropyrido[2,3-d]pyrimidin-4-yl)-cis-2,6-dimethylpiperazine-1-carboxylate (0.209 g, 0.336 mmol) in trifluoroacetic acid (2.6 mL, 34 mmol) was stirred at rt for 15 min. The reaction mixture was concentrated in vacuo to provide crude (M)-6-chloro-4-(cis-3,5-dimethylpiperazin-1-yl)-7-(2-fluorophenyl)-1-(2-isopropyl-4-methylpyridin-3-yl)pyrido[2,3-d]pyrimidin-2(1H)-one as an oil.

A solution of the crude (M)-6-chloro-4-(cis-3,5-dimethylpiperazin-1-yl)-7-(2-fluorophenyl)-1-(2-isopropyl-4-methylpyridin-3-yl)pyrido[2,3-d]pyrimidin-2(1H)-one, DIPEA (0.176 mL, 1.01 mmol), and acryloyl chloride (0.5 M in DCM, 0.673 mL, 0.336 mmol) in DCM (1.7 mL) was stirred at rt for 15 min. The reaction mixture was diluted with EtOAc (100 mL), added to a separatory funnel, and washed with saturated aqueous NaHCO$_3$ (2×75 mL). The organic layer was separated, dried over anhydrous Na$_2$SO$_4$, and concentrated in vacuo. The crude product was adsorbed onto silica and was purified by silica gel chromatography (eluent: 0-100% EtOAc/EtOH (3:1)/heptane) to give (M)-4-(4-acryloyl-cis-3,5-dimethylpiperazin-1-yl)-6-chloro-7-(2-fluorophenyl)-1-(2-isopropyl-4-methylpyridin-3-yl) pyrido[2,3-d]pyrimidin-2(1H)-one (85 mg, 0.15 mmol, 44% yield) as an off-white waxy solid. $^1$H NMR (400 MHz, CDCl$_3$) δ 8.49 (br s, 1H) 8.33 (br s, 1H) 7.42 (br d, J=3.3 Hz, 1H) 7.03-7.21 (m, 4H) 6.58-6.72 (m, 1H) 6.44 (br d, J=15.8 Hz, 1H) 5.81 (br d, J=9.1 Hz, 1H) 4.73 (br s, 2H) 4.35 (br d, J=13.1 Hz, 2H) 3.62 (br d, J=11.8 Hz, 2H) 2.64-2.79 (m, 1H) 2.04 (br s, 3H) 1.58 (br s, 6H) 1.19-1.25 (m, 3H) 1.02-1.09 (m, 3H). $^{19}$F NMR (377 MHz, CDCl$_3$) δ -112.58 (s, 1F). m/z (ESI, +ve ion): 574.8 (M+H)$^+$.

Example 14

(M)-4-(4-Acryloyl-cis-3,5-dimethylpiperazin-1-yl)-6-chloro-7-(2-fluoro-6-hydroxyphenyl)-1-(2-isopropyl-4-methylpyridin-3-yl)pyrido[2,3-d]pyrimidin-2(1H)-one

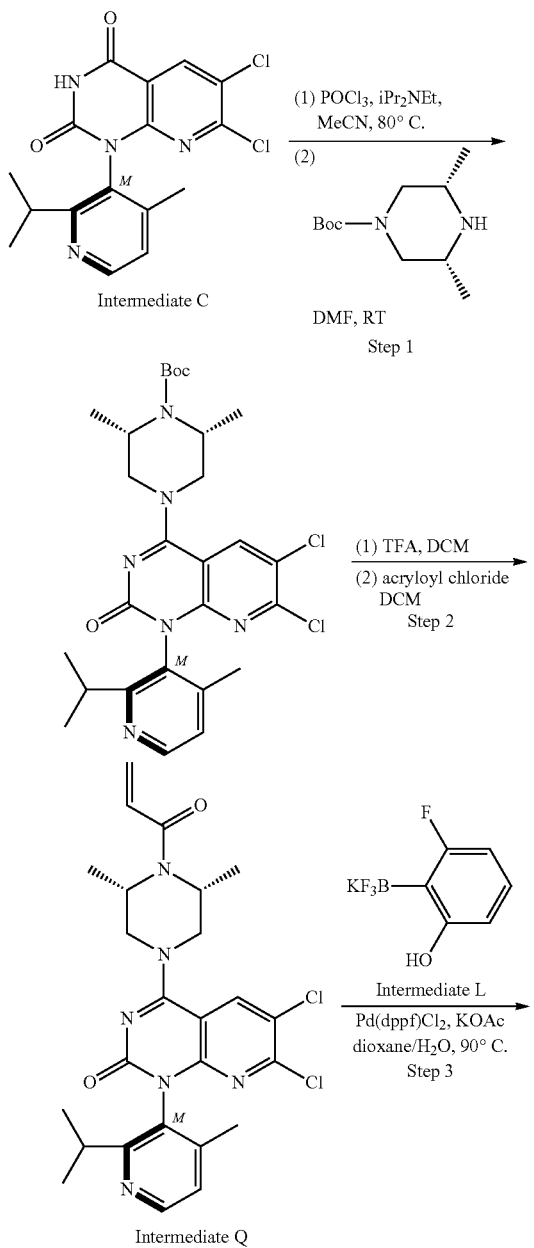

-continued

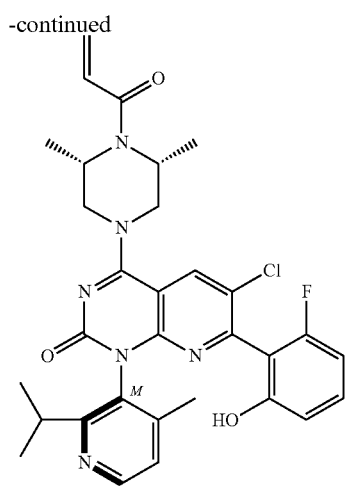

Step 1: tert-Butyl (M)-4-(6,7-dichloro-1-(2-isopropyl-4-methylpyridin-3-yl)-2-oxo-1,2-dihydropyrido[2,3-d]pyrimidin-4-yl)-cis-2,6-dimethylpiperazine-1-carboxylate Phosphorous oxychloride (0.37 mL, 3.92 mmol) was added dropwise to a solution of (M)-6,7-dichloro-1-(2-isopropyl-4-methylpyridin-3-yl)pyrido[2,3-d]pyrimidine-2,4(1H,3H)-dione (1.17 g, 3.20 mmol, Intermediate C) and DIPEA (0.74 mL, 4.25 mmol) in acetonitrile (3.27 mL). The mixture was heated to 80° C. for 1 h, then was cooled to 0° C. DIPEA (1.71 mL, 9.80 mmol) and t-butyl cis-2,6-dimethylpiperazine-1-carboxylate (0.70 g, 3.27 mmol, Enamine, San Diego, Calif.) were added. This mixture was warmed to rt, stirred for 1 h then poured into a cold solution of saturated NaHCO$_3$ and stirred vigorously for 10 min. The mixture was partitioned between EtOAc and brine, the layers were separated, the aqueous layer was back-extracted with EtOAc and the combined organic extracts were dried over MgSO$_4$, filtered, and concentrated in vacuo. The crude material was purified by silica gel chromatography (eluent: 0-40% EtOAc-EtOH (3:1)/heptanes) to provide tert-butyl (M)-4-(6,7-dichloro-1-(2-isopropyl-4-methylpyridin-3-yl)-2-oxo-1,2-dihydropyrido[2,3-d]pyrimidin-4-yl)-cis-2,6-dimethylpiperazine-1-carboxylate (1.65 g, 2.94 mmol, 90% yield) as a white solid. $^1$H NMR (400 MHz, DMSO-d$_6$) δ ppm 8.58-8.47 (m, 2H), 7.26 (m, 1H), 4.23 (m, 4H), 3.58 (m, 2H), 2.66-2.61 (m, 1H), 1.94 (s, 3H), 1.44 (s, 9H), 1.32-1.27 (m, 6H), 1.08-0.97 (m, 6H). m/z (ESI, +ve ion): 561.0 (M+H)$^+$.

Step 2: (M)-4-(4-Acryloyl-cis-3,5-dimethylpiperazin-1-yl)-6,7-dichloro-1-(2-isopropyl-4-methylpyridin-3-yl)pyrido[2,3-d]pyrimidin-2(1H)-one (Intermediate Q)

A vial was loaded with tert-butyl (M)-4-(6,7-dichloro-1-(2-isopropyl-4-methylpyridin-3-yl)-2-oxo-1,2-dihydropyrido[2,3-d]pyrimidin-4-yl)-cis-2,6-dimethylpiperazine-1-carboxylate (1.65 g, 2.94 mmol), dichloromethane (14.7 mL), and trifluoroacetic acid (4.4 mL, 58.8 mmol). The mixture was stirred for 1 h at rt, partitioned between EtOAc and/NaHCO$_3$, washed with NaHCO$_3$, washed with brine, dried over MgSO$_4$, and concentrated in vacuo to provide crude (M)-6,7-dichloro-4-(cis-3,5-dimethylpiperazin-1-yl)-1-(2-isopropyl-4-methylpyridin-3-yl)pyrido[2,3-d]pyrimidin-2(1H)-one.

The residue of (M)-6,7-dichloro-4-(cis-3,5-dimethylpiperazin-1-yl)-1-(2-isopropyl-4-methylpyridin-3-yl)pyrido[2,3-d]pyrimidin-2(1H)-one was re-dissolved in DCM (14.7 mL) followed by dropwise addition of acryloyl chloride (2.80 mL, 3.09 mmol). The reaction was stirred for 30 min at RT, partitioned between EtOAc and saturated NaHCO$_3$, washed with saturated NaHCO$_3$, washed with brine, dried over MgSO$_4$ and purified by silica gel chromatography (eluent: 30-100% tOAc-EtOH (3:1)/heptanes) to provide (M)-4-(4-acryloyl-cis-3,5-dimethylpiperazin-1-yl)-6,7-dichloro-1-(2-isopropyl-4-methylpyridin-3-yl)pyrido[2,3-d]pyrimidin-2(1H)-one (1.18 g, 78% yield) as a white solid that was used without further purification. m/z (ESI, +ve ion): 515.0 (M+H)$^+$.

Step 3: (M)-4-(4-Acryloyl-cis-3,5-dimethylpiperazin-1-yl)-6-chloro-7-(2-fluoro-6-hydroxyphenyl)-1-(2-isopropyl-4-methylpyridin-3-yl)pyrido[2,3-d]pyrimidin-2(1H)-one A vial was charged with (M)-4-(4-acryloyl-cis-3,5-dimethylpiperazin-1-yl)-6,7-dichloro-1-(2-isopropyl-4-methylpyridin-3-yl)pyrido[2,3-d]pyrimidin-2(1H)-one (Intermediate Q, 0.30 g, 0.57 mmol), potassium trifluoro(2-fluoro-6-hydroxyphenyl)borate (0.15 g, 0.69 mmol, Intermediate L), dichloro[1,1'-bis(diphenylphosphino)ferrocene]palladium (II) dichloromethane adduct (0.04 g, 0.06 mmol), and KOAc (0.28 g, 2.86 mmol). The flask was evacuated and backfilled with N$_2$ followed by addition of 1,4-dioxane (2.30 mL) and water (0.57 mL). The mixture was stirred at 90° C. for 18 h and purified by silica gel chromatography (eluent 30-100% EtOAc-EtOH (3:1)/heptanes) to provide 0.26 g of crude material which was further purified using preparatory SFC (eluent 20% MeOH) to provide (M)-4-(4-acryloyl-cis-3,5-dimethylpiperazin-1-yl)-6-chloro-7-(2-fluoro-6-hydroxyphenyl)-1-(2-isopropyl-4-methylpyridin-3-yl)pyrido[2,3-d]pyrimidin-2(1H)-one (0.12 g, 34.3% yield) as a yellow solid. $^1$H NMR (400 MHz, DMSO-d$_6$) δ ppm 10.13 (br s, 1H), 8.51 (s, 1H), 8.38 (d, J=5.0 Hz, 1H), 7.27-7.14 (m, 2H), 6.81 (dd, J=10.6, 16.6 Hz, 1H), 6.74-6.62 (m, 2H), 6.20 (dd, J=2.4, 16.7 Hz, 1H), 5.79-5.71 (m, 1H), 4.58 (br s, 2H), 4.32 (br t, J=15.7 Hz, 2H), 3.63 (m, 2H), 2.76-2.68 (m, 1H), 1.91 (m, 3H), 1.41 (m, 6H), 1.07 (d, J=6.8 Hz, 3H), 0.92 (br d, J=6.6 Hz, 3H). $^{19}$F NMR (376 MHz, DMSO-d$_6$) δ ppm −113.91 (s, 1F). m/z (ESI, +ve ion): 591.0 (M+H)$^+$.

Example 15

(M)-4-(4-Acryloyl-cis-3,5-dimethylpiperazin-1-yl)-7-(2-amino-6-fluorophenyl)-6-chloro-1-(2-isopropyl-4-methylpyridin-3-yl)pyrido[2,3-d]pyrimidin-2(1H)-one

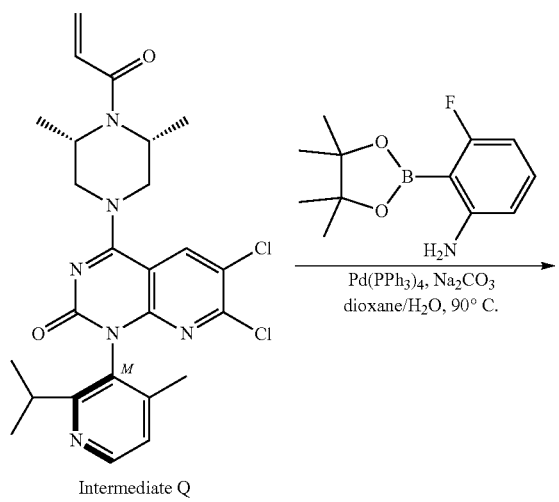

Intermediate Q

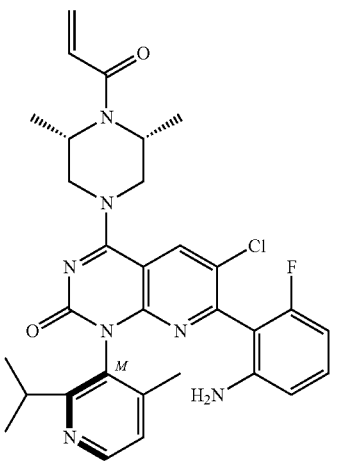

(M)-4-(4-Acryloyl-cis-3,5-dimethylpiperazin-1-yl)-7-(2-amino-6-fluorophenyl)-6-chloro-1-(2-isopropyl-4-methylpyridin-3-yl)pyrido[2,3-d]pyrimidin-2(1H)-one A vial was charged with (M)-4-(4-acryloyl-cis-3,5-dimethylpiperazin-1-yl)-6,7-dichloro-1-(2-isopropyl-4-methylpyridin-3-yl)pyrido[2,3-d]pyrimidin-2(1H)-one (Intermediate Q, 0.30 g, 0.57 mmol), (2-amino-6-fluorophenyl)boronic acid pinacol ester (0.15 g, 0.63 mmol, CombiPhos, Trenton, N.J.), tetrakis(triphenylphosphine)palladium(0) (0.07 g, 0.06 mmol), and KOAc (0.28 g, 2.86 mmol). The flask was evacuated and backfilled with $N_2$ followed by addition of 1,4-dioxane (2.30 mL) and water (0.57 mL). The mixture was stirred at 90° C. for 18 h and purified by silica gel chromatography (eluent: 30-100% EtOAc-EtOH (3:1)/heptane) to provide crude material which was further purified using preparatory SFC (eluent 15% MeOH) to provide (M)-4-(4-acryloyl-cis-3,5-dimethylpiperazin-1-yl)-7-(2-amino-6-fluorophenyl)-6-chloro-1-(2-isopropyl-4-methylpyridin-3-yl)pyrido[2,3-d]pyrimidin-2(1H)-one (0.17 g, 49% yield) as a yellow solid. $^1$H NMR (400 MHz, DMSO-$d_6$) δ ppm 8.50 (s, 1H), 8.39 (d, J=5.0 Hz, 1H), 7.19 (d, J=4.8 Hz, 1H), 7.09-7.02 (m, 1H), 6.81 (dd, J=10.5, 16.5 Hz, 1H), 6.44 (m 1H), 6.31 (t, J=8.9 Hz, 1H), 6.20 (dd, J=2.2, 16.5 Hz, 1H), 5.77-5.73 (m, 1H), 5.11 (br s, 2H), 4.60 (m, 2H), 4.37-4.24 (m, 2H), 3.64 (m, 2H), 2.91-2.68 (m, 1H), 1.99 (s, 3H), 1.39-1.41 (m 6H), 1.11-1.02 (m, 3H), 0.88 (d, J=6.6 Hz, 3H). $^{19}$F NMR (376 MHz, DMSO-$d_6$) δ ppm −115.73 (s, 1F). m/z (ESI, +ve ion): 591.0 (M+H)$^+$.

Example 16

(M)-4-(4-Acryloyl-cis-3,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one

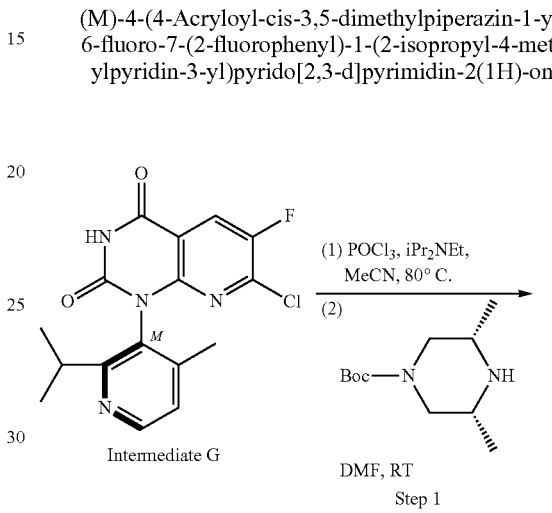

Intermediate G

Step 1

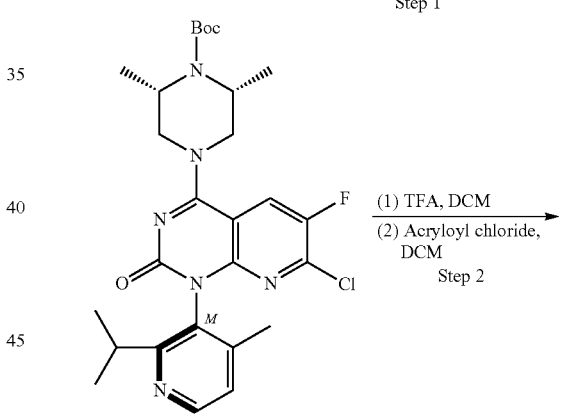

Step 2

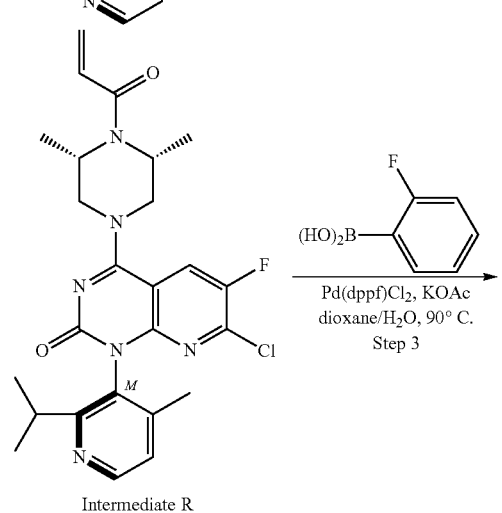

Intermediate R

-continued

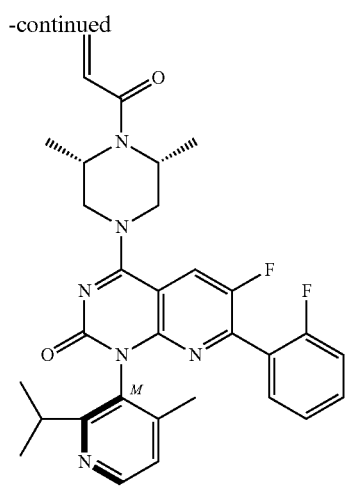

Step 1: tert-Butyl (M)-4-(7-chloro-6-fluoro-1-(2-isopropyl-4-methylpyridin-3-yl)-2-oxo-1,2-dihydropyrido[2,3-d]pyrimidin-4-yl)-cis-2,6-dimethylpiperazine-1-carboxylate Phosphorous oxychloride (0.34 mL, 3.63 mmol) was added dropwise to a solution of (M)-7-chloro-6-fluoro-1-(2-isopropyl-4-methylpyridin-3-yl)pyrido[2,3-d]pyrimidine-2,4(1H,3H)-dione (Intermediate G, 1.03 g, 2.96 mmol) and Hunig's base (0.69 mL, 3.93 mmol) in acetonitrile (3.02 mL). The mixture was heated to 80° C. for 1 h, then was cooled to 0° C. DIPEA (1.58 mL, 9.07 mmol) and t-butyl cis-2,6-dimethylpiperazine-1-carboxylate (0.64 g, 3.62 mmol, Enamine, San Diego, Calif.) were added. This mixture was warmed to rt, stirred for 1 h, then poured into a cold solution of saturated NaHCO$_3$ and stirred vigorously for 10 min. The mixture was partitioned between EtOAc and brine, the layers were separated, the aqueous layer was back-extracted with EtOAc and the combined organic extracts were dried over MgSO$_4$, filtered, and concentrated in vacuo. The crude material was purified by silica gel chromatography (eluent: 0-40% EtOAc-EtOH (3:1)/heptanes) to provide tert-butyl (M)-4-(7-chloro-6-fluoro-1-(2-isopropyl-4-methylpyridin-3-yl)-2-oxo-1,2-dihydropyrido[2,3-d]pyrimidin-4-yl)-cis-2,6-dimethylpiperazine-1-carboxylate (1.38 g, 84% yield) as a white solid. $^1$H NMR (400 MHz, DMSO-d$_6$) δ ppm 8.48 (d, J=4.8 Hz, 1H), 8.40 (d, J=8.5 Hz, 1H), 7.26 (d, J=4.8 Hz, 1H), 4.32-4.16 (m, 4H), 3.66-3.55 (m, 2H), 2.65-2.56 (m, 1H), 1.94 (s, 3H), 1.44 (s, 9H), 1.29 (dd, J=3.1, 6.6 Hz, 6H), 1.14-0.95 (m, 6H). $^{19}$F NMR (376 MHz, DMSO-d$_6$) δ ppm −128.10 (s, 1F); m/z (ESI, +ve ion): 545.2 (M+H)$^+$.

Step 2: (M)-4-(4-Acryloyl-cis-3,5-dimethylpiperazin-1-yl)-7-chloro-6-fluoro-1-(2-isopropyl-4-methylpyridin-3-yl)pyrido[2,3-d]pyrimidin-2(1H)-one (Intermediate R)

A vial was loaded with tert-butyl (M)-4-(7-chloro-6-fluoro-1-(2-isopropyl-4-methylpyridin-3-yl)-2-oxo-1,2-dihydropyrido[2,3-d]pyrimidin-4-yl)-cis-2,6-dimethylpiperazine-1-carboxylate (1.38 g, 2.53 mmol), DCM (12.7 mL), and trifluoroacetic acid (3.77 mL, 50.6 mmol). The mixture was stirred for 1 h at rt, partitioned between EtOAc and NaHCO$_3$, washed with NaHCO$_3$, washed with brine, dried over MgSO$_4$, and concentrated in vacuo to provide (M)-7-chloro-4-(cis-3,5-dimethylpiperazin-1-yl)-6-fluoro-1-(2-isopropyl-4-methylpyridin-3-yl)pyrido[2,3-d]pyrimidin-2(1H)-one as a crude residue.

The residue of (M)-7-chloro-4-(cis-3,5-dimethylpiperazin-1-yl)-6-fluoro-1-(2-isopropyl-4-methylpyridin-3-yl)pyrido[2,3-d]pyrimidin-2(1H)-one was re-dissolved in dichloromethane (12.7 mL) and acryloyl chloride (2.42 mL, 2.66 mmol) was added dropwise. The reaction was stirred for 30 min at rt, partitioned between EtOAc/NaHCO$_3$, washed with NaHCO$_3$, washed with brine, dried over MgSO$_4$, and purified by silica gel chromatography (eluent: 30-100% EtOAc-EtOH (3:1)/heptane) to provide (M)-4-(4-acryloyl-cis-3,5-dimethylpiperazin-1-yl)-7-chloro-6-fluoro-1-(2-isopropyl-4-methylpyridin-3-yl)pyrido[2,3-d]pyrimidin-2(1H)-one (0.88 g, 1.77 mmol, 70.0% yield) as a white solid that was used without further purification. m/z (ESI, +ve ion): 499.0 (M+H)$^+$.

Step 3: (M)-4-(4-Acryloyl-cis-3,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one A vial was charged with (M)-4-(4-acryloyl-cis-3,5-dimethylpiperazin-1-yl)-7-chloro-6-fluoro-1-(2-isopropyl-4-methylpyridin-3-yl)pyrido[2,3-d]pyrimidin-2(1H)-one (Intermediate R, 0.30 g, 0.59 mmol), (2-fluorophenyl)boronic acid (0.10 g, 0.71 mmol), dichloro[1,1'-bis(diphenylphosphino)ferrocene]palladium (II) dichloromethane adduct (0.04 g, 0.06 mmol), and KOAc (0.29 g, 2.96 mmol). The flask was evacuated and backfilled with N$_2$ followed by addition of 1,4-dioxane (2.37 mL) and water (0.59 mL). The mixture was stirred at 90° C. for 2 h, then was cooled to rt, and purified by silica gel chromatography (eluent: 30-100% EtOAc-EtOH (3:1)/heptane) to provide (M)-4-(4-acryloyl-cis-3,5-dimethylpiperazin-1-yl)-6-fluoro-7-(2-fluorophenyl)-1-(2-isopropyl-4-methylpyridin-3-yl)pyrido[2,3-d]pyrimidin-2(1H)-one (0.20 g, 63% yield) as an orange solid. $^1$H NMR (400 MHz, DMSO-d$_6$) δ ppm 8.43 (d, J=5.0 Hz, 1H), 8.39 (d, J=9.7 Hz, 1H), 7.60-7.45 (m, 1H), 7.37-7.21 (m, 4H), 6.80 (dd, J=10.6, 16.6 Hz, 1H), 6.19 (dd, J=2.4, 16.7 Hz, 1H), 5.77-5.73 (m, 1H), 4.57 (br s, 2H), 4.33 (m, 2H), 3.73-3.65 (m, 2H), 2.75-2.68 (m, 1H), 1.97-1.90 (m, 3H), 1.39 (t, J=6.5 Hz, 6H), 1.07 (d, J=6.6 Hz, 3H), 0.95 (d, J=6.8 Hz, 3H). $^{19}$F NMR (376 MHz, DMSO-d$_6$) δ ppm −113.83 (d, J=32 Hz, 1F), −128.96 (d, J=32 Hz, 1F). m/z (ESI, +ve ion): 559.0 (M+H)$^+$.

Example 17

(M)-4-(4-Acryloyl-cis-3,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one

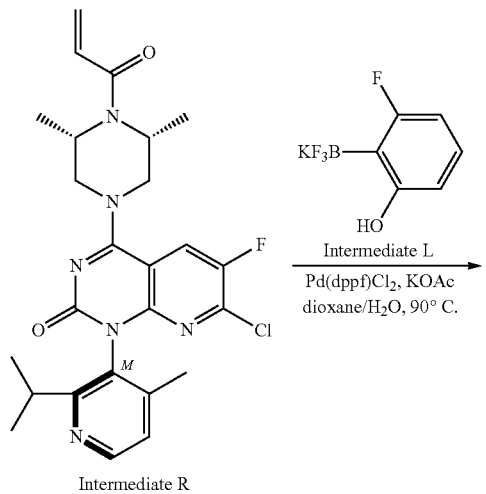

(M)-4-(4-Acryloyl-cis-3,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one

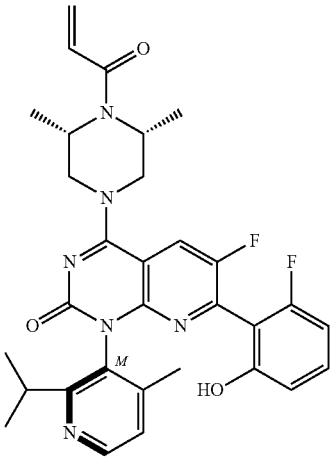

A vial was charged with (M)-4-(4-acryloyl-cis-3,5-dimethylpiperazin-1-yl)-7-chloro-6-fluoro-1-(2-isopropyl-4-methylpyridin-3-yl)pyrido[2,3-d]pyrimidin-2(1H)-one (Intermediate R, 0.30 g, 0.59 mmol), potassium trifluoro(2-fluoro-6-hydroxyphenyl)borate (0.15 g, 0.69 mmol, Intermediate L), dichloro[1,1'-bis(diphenylphosphino)ferrocene]palladium (II) dichloromethane adduct (0.04 g, 0.06 mmol), and KOAc (0.28 g, 2.86 mmol). The flask was evacuated and backfilled with $N_2$ followed by addition of 1,4-dioxane (2.30 mL) and water (0.57 mL). The mixture was stirred at 90° C. for 18 h and purified by silica gel chromatography (eluent: 30-100% EtOAc-EtOH (3:1)/heptanes) to provide (M)-4-(4-acryloyl-cis-3,5-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2 (1H)-one (0.21 g, 0.37 mmol) as an orange solid. $^1$H NMR (400 MHz, DMSO-$d_6$) δ ppm 10.20 (br s, 1H), 8.39 (d, J=5.0 Hz, 1H), 8.33 (d, J=9.1 Hz, 1H), 7.31-7.23 (m, 1H), 7.19 (d, J=4.8 Hz, 1H), 6.84-6.66 (m, 3H), 6.19 (dd, J=2.5, 16.6 Hz, 1H), 5.77-5.73 (m, 1H), 4.56 (br s, 2H), 4.42-4.21 (m, 2H), 3.66 (ddd, J=3.8, 4.0, 13.3 Hz, 2H), 2.74-2.68 (m, 1H), 1.99-1.88 (m, 3H), 1.41-1.39 (m, 6H), 1.09-1.03 (m, 3H), 0.92 (d, J=6.6 Hz, 3H). $^{19}$F NMR (377 MHz, DMSO-$d_6$) δ ppm −115.68 (s, 1F), −128.36 (s, 1F). m/z (ESI, +ve ion): 575.2 (M+H)$^+$.

Example 18

(M)-4-(4-Acryloyl-cis-3,5-dimethylpiperazin-1-yl)-7-(2-amino-6-fluorophenyl)-6-fluoro-1-(2-isopropyl-4-methylpyridin-3-yl)pyrido[2,3-d]pyrimidin-2(1H)-one

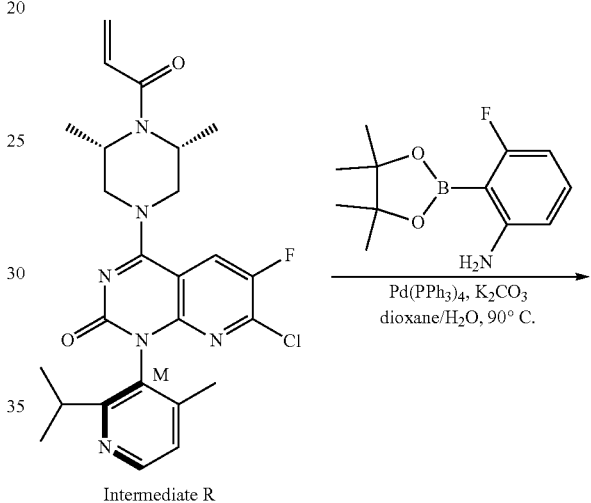

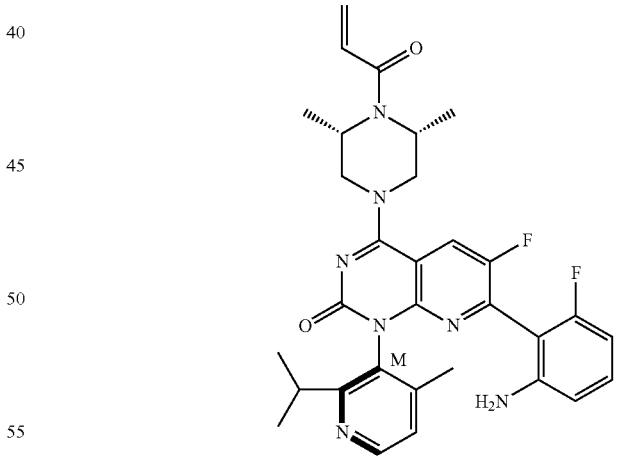

(M)-4-(4-Acryloyl-cis-3,5-dimethylpiperazin-1-yl)-7-(2-amino-6-fluorophenyl)-6-fluoro-1-(2-isopropyl-4-methylpyridin-3-yl)pyrido[2,3-d]pyrimidin-2(1H)-one A vial was charged with (M)-4-(4-acryloyl-cis-3,5-dimethylpiperazin-1-yl)-7-chloro-6-fluoro-1-(2-isopropyl-4-methylpyridin-3-yl)pyrido[2,3-d]pyrimidin-2(1H)-one (Intermediate R, 0.3 g, 0.59 mmol), potassium carbonate (178 mg, 2.96 mmol), (2-amino-6-fluorophenyl)boronic acid pinacol ester (0.15 g, 0.65 mmol, CombiPhos, Trenton, N.J.), tetrakis(triphenylphosphine)palladium(0) (68 mg, 0.06 mmol), and 1,4-dioxane (2.0 mL). The mixture was degassed with $N_2$, water (1.0 mL) was added, and the mixture was stirred at 90° C. for 2 h, then cooled to rt, adsorbed directly onto $SiO_2$, and purified by silica gel chromatography (eluent: 30%-100% EtOAc-EtOH (3:1)/heptane) to provide (M)-4-(4-acryloyl-cis-3,5-dimethylpiperazin-1-yl)-7-(2-amino-6-fluorophenyl)-6-fluoro-1-(2-isopropyl-4-methylpyridin-3-yl)pyrido[2,3-d]pyrimidin-2(1H)-one (0.30 g, 88% yield) as an orange solid. $^1$H NMR (400 MHz, DMSO-$d_6$) δ ppm 8.44 (d, J=4.8 Hz, 1H), 8.34 (d, J=9.5 Hz, 1H), 7.22 (d, J=4.8 Hz, 1H), 7.14-7.07 (m, 1H), 6.81 (dd, J=10.4, 16.6 Hz, 1H), 6.48 (d, J=8.3 Hz, 1H), 6.37 (t, J=8.8 Hz, 1H), 6.19 (dd, J=2.4, 16.7 Hz, 1H), 5.78-5.72 (m, 1H), 4.57 (br s, 2H), 4.33 (m, 2H), 4.27 (m, 2H), 3.73-3.64 (m, 2H), 2.77-2.68 (m, 1H), 1.99-1.90 (m, 3H), 1.39 (br d, J=14.1 Hz, 3H), 1.40 (br d, J=13.9 Hz, 3H), 1.06 (d, J=6.6 Hz, 3H), 0.94 (d, J=6.8 Hz, 3H). $^{19}$F NMR (376 MHz, DMSO-$d_6$) δ ppm −114.27 (d, J=32 Hz, 1F), −126.96 (d, J=32 Hz, 1F). m/z (ESI, +ve ion) 574.1 (M+H)$^+$.

Example 19

4-(4-Acryloyl-cis-3,5-dimethylpiperazin-1-yl)-6-chloro-1-(4,6-diisopropylpyrimidin-5-yl)-7-(2-fluorophenyl)pyrido[2,3-d]pyrimidin-2(1H)-one

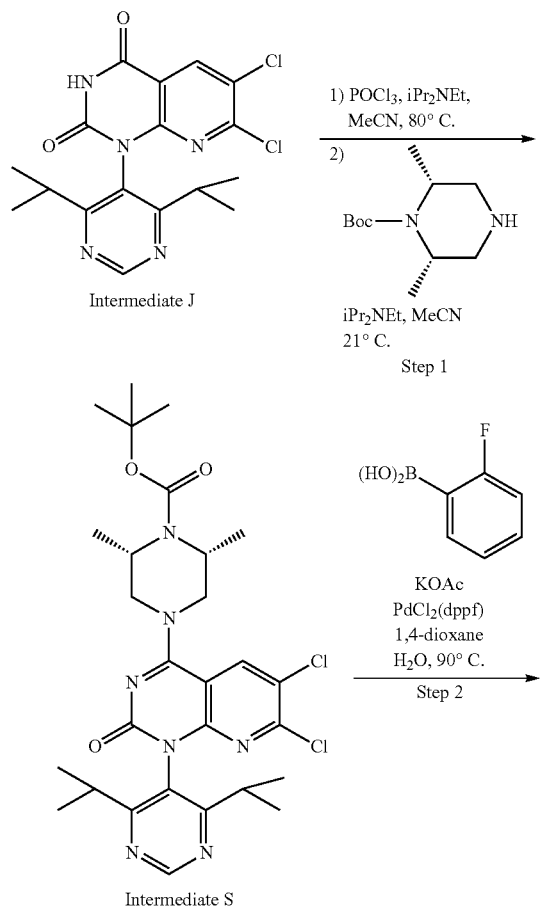

Intermediate S

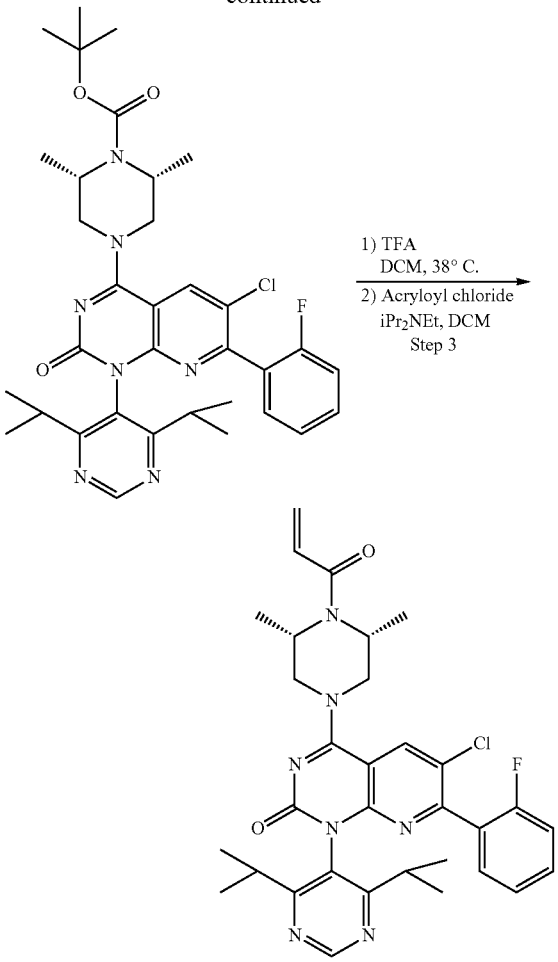

Step 1: tert-Butyl 4-(6,7-dichloro-1-(4,6-diisopropylpyrimidin-5-yl)-2-oxo-1,2-dihydropyrido[2,3-d]pyrimidin-4-yl)-cis-2,6-dimethylpiperazine-1-carboxylate (Intermediate S)

To a 100-mL round-bottomed flask was added 6,7-dichloro-1-(4,6-diisopropylpyrimidin-5-yl)pyrido[2,3-d]pyrimidine-2,4(1H,3H)-dione (Intermediate J, 0.300 g, 0.761 mmol) and DIPEA (0.173 mL, 0.989 mmol) in acetonitrile (3.80 mL). Then phosphorous oxychloride (0.085 mL, 0.913 mmol) was added slowly into the reaction mixture. The flask was fitted with an air-cooled condenser and the mixture was stirred and heated at 80° C., while under an inert ($N_2$) atmosphere for 30 min. The reaction mixture was removed from the heat bath and allowed to cool to rt. The reaction mixture was cooled to 0° C. DIPEA (0.5 mL) was added slowly into the mixture. A mixture of t-butyl cis-2,6-dimethylpiperazine-1-carboxylate (0.204 g, 0.951 mmol) in MeCN (5 mL) was added slowly into the reaction mixture. The ice bath was removed and the overall mixture was allowed to warm to rt over 10 min. The reaction mixture was concentrated in vacuo. The crude material was adsorbed onto a plug of silica gel and purified by silica gel chromatography (eluent: 0-50% EtOAc/heptane) to afford tert-butyl 4-(6,7-dichloro-1-(4,6-diisopropylpyrimidin-5-yl)-2-oxo-1,2-dihydropyrido[2,3-d]pyrimidin-4-yl)-cis-2,6-dimethylpiperazine-1-carboxylate (0.233 g, 0.395 mmol, 51.9% yield) as tan solid. $^1$H NMR (400 MHz, DMSO-$d_6$) δ ppm 9.15 (s, 1H) 8.55 (s, 1H) 4.21-4.30 (m, 4H) 3.61 (br dd, J=13.58, 4.46 Hz, 2H) 2.70 (quin, J=6.63 Hz, 2H) 1.45 (s, 9H) 1.30 (d, J=6.63 Hz, 6H) 1.09 (d, J=6.63 Hz, 6H) 1.01 (d, J=6.63 Hz, 6H). m/z (ESI, +ve ion): 590.1 (M+H)$^+$.

Step 2: tert-Butyl 4-(6-chloro-1-(4,6-diisopropylpyrimidin-5-yl)-7-(2-fluorophenyl)-2-oxo-1,2-dihydropyrido[2,3-d]pyrimidin-4-yl)-cis-2,6-dimethylpiperazine-1-carboxylate To a 100-mL round-bottomed flask was added tert-butyl 4-(6,7-dichloro-1-(4,6-diisopropylpyrimidin-5-yl)-2-oxo-1,2-dihydropyrido[2,3-d]pyrimidin-4-yl)-cis-2,6-dimethylpiperazine-1-carboxylate (Intermediate S, 0.225 g, 0.381 mmol) and KOAc (0.112 g, 1.143 mmol) in 1,4-dioxane (2.54 mL) and the reaction mixture was degassed by bubbling N$_2$ into the mixture for 5 min. (1,1'-bis(diphenylphosphino)ferrocene)dichloropalladium (0.028 g, 0.038 mmol), followed by 2-fluorophenylboronic acid (0.064 g, 0.457 mmol) and water (0.1 mL) were added into the reaction mixture. The mixture was stirred and heated at 80° C. for 45 min. The reaction mixture was diluted with sat. aq. ammonium chloride and EtOAc. The layers were separated and the aqueous layer was extracted with EtOAc. The combined organic extracts were dried over MgSO$_4$, filtered and concentrated in vacuo. The crude material was adsorbed onto a plug of silica gel and purified by silica gel chromatography (eluent: 0-100% EtOAc/heptane) to afford tert-butyl 4-(6-chloro-1-(4,6-diisopropylpyrimidin-5-yl)-7-(2-fluorophenyl)-2-oxo-1,2-dihydropyrido[2,3-d]pyrimidin-4-yl)-cis-2,6-dimethylpiperazine-1-carboxylate (0.219 g, 0.337 mmol, 88% yield) as light-yellow solid. m/z (ESI, +ve ion): 650.2 (M+H)$^+$.

Step 3: 4-(4-Acryloyl-cis-3,5-dimethylpiperazin-1-yl)-6-chloro-1-(4,6-diisopropylpyrimidin-5-yl)-7-(2-fluorophenyl)pyrido[2,3-d]pyrimidin-2(1H)-one To a 100-mL round-bottomed flask was added tert-butyl 4-(6-chloro-1-(4,6-diisopropylpyrimidin-5-yl)-7-(2-fluorophenyl)-2-oxo-1,2-dihydropyrido[2,3-d]pyrimidin-4-yl)-cis-2,6-dimethylpiperazine-1-carboxylate (0.219 g, 0.337 mmol) and trifluoroacetic acid (0.251 mL, 3.37 mmol) in DCM (3.37 mL). The reaction mixture was stirred and heated at 38° C. for 2.5 h, while under an inert (N$_2$) atmosphere. The reaction mixture was concentrated in vacuo to provide crude 6-chloro-1-(4,6-diisopropylpyrimidin-5-yl)-4-(cis-3,5-dimethylpiperazin-1-yl)-7-(2-fluorophenyl)pyrido[2,3-d]pyrimidin-2(1H)-one. This material was carried directly into the next step of the synthesis, without further purification.

The crude 6-chloro-1-(4,6-diisopropylpyrimidin-5-yl)-4-(cis-3,5-dimethylpiperazin-1-yl)-7-(2-fluorophenyl)pyrido[2,3-d]pyrimidin-2(1H)-one was diluted with dichloromethane (3.37 mL), then the reaction mixture was cooled to 0° C. DIPEA (0.706 mL, 4.04 mmol) was added into the reaction mixture and the mixture was allowed to stir 2 min. Acryloyl chloride (0.027 mL, 0.337 mmol) was added dropwise into the reaction mixture and the mixture was allowed to stir 30 min. The mixture was diluted with DCM and sat. aq. NaHCO$_3$, then the layers were separated. The aqueous layer was extracted with DCM. The combined organic extracts were dried over MgSO$_4$, filtered and concentrated in vacuo. The crude material was adsorbed onto a plug of silica gel and purified by silica gel chromatography (eluent: 0-5% MeOH/DCM) to afford 4-(4-acryloyl-cis-3,5-dimethylpiperazin-1-yl)-6-chloro-1-(4,6-diisopropylpyrimidin-5-yl)-7-(2-fluorophenyl)pyrido[2,3-d]pyrimidin-2(1H)-one (0.080 g, 0.132 mmol, 39.3% yield) as light-yellow solid. $^1$H NMR (400 MHz, DMSO-$d_6$) δ ppm 8.99 (s, 1H) 8.50 (s, 1H) 7.42-7.48 (m, 1H) 7.19-7.27 (m, 2H) 7.11 (t, J=7.07 Hz, 1H) 6.74 (dd, J=16.59, 10.57 Hz, 1H) 6.13 (dd, J=16.59, 2.28 Hz, 1H) 5.68 (dd, J=10.37, 2.28 Hz, 1H) 4.52 (br s, 2H) 4.27 (br d, J=13.68 Hz, 2H) 3.62 (dd, J=13.68, 4.56 Hz, 2H) 2.61-2.72 (m, 2H) 1.34 (br d, J=6.63 Hz, 6H) 1.02 (d, J=6.84 Hz, 6H) 0.86 (d, J=6.63 Hz, 6H). m/z (ESI, +ve ion): 604.0 (M+H)$^+$.

Example 20

4-(4-Acryloyl-cis-3,5-dimethylpiperazin-1-yl)-6-chloro-1-(4,6-diisopropylpyrimidin-5-yl)-7-(2-fluoro-6-hydroxyphenyl)pyrido[2,3-d]pyrimidin-2(1H)-one

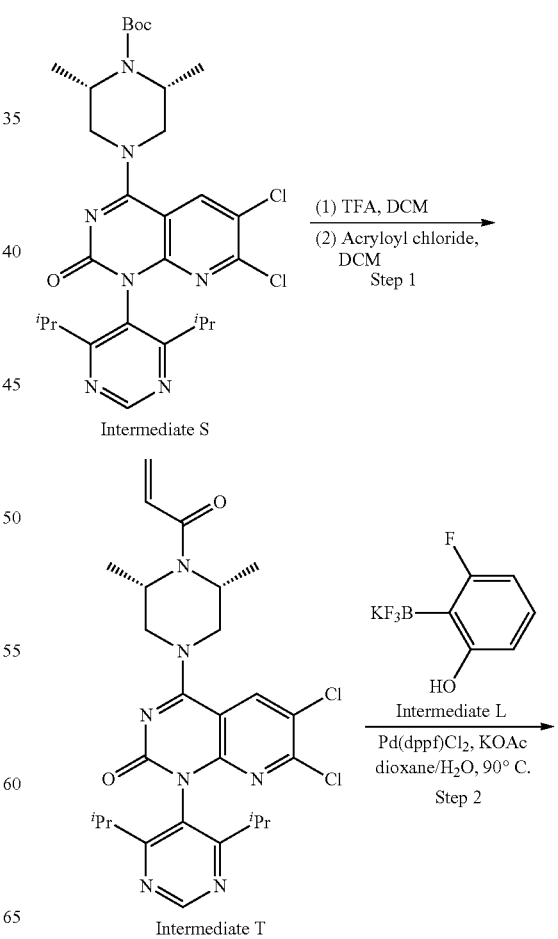

-continued

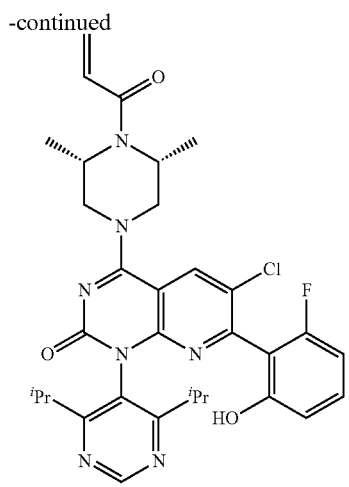

Step 1: 4-(4-Acryloyl-cis-3,5-dimethylpiperazin-1-yl)-6,7-dichloro-1-(4,6-diisopropylpyrimidin-5-yl)pyrido[2,3-d]pyrimidin-2(1H)-one (Intermediate T)

A vial was loaded with tert-butyl 4-(6,7-dichloro-1-(4,6-diisopropylpyrimidin-5-yl)-2-oxo-1,2-dihydropyrido[2,3-d]pyrimidin-4-yl)-cis-2,6-dimethylpiperazine-1-carboxylate (Intermediate S, 0.76 g, 1.28 mmol), DCM (6.4 mL), and trifluoroacetic acid (1.91 mL, 25.6 mmol). The mixture was stirred for 1 h at rt, partitioned between EtOAc and NaHCO$_3$, washed with NaHCO$_3$, washed with brine, dried over MgSO$_4$, and concentrated in vacuo to provide 6,7-dichloro-1-(4,6-diisopropylpyrimidin-5-yl)-4-(cis-3,5-dimethylpiperazin-1-yl)pyrido[2,3-d]pyrimidin-2(1H)-one as a crude residue.

The residue of 6,7-dichloro-1-(4,6-diisopropylpyrimidin-5-yl)-4-(cis-3,5-dimethylpiperazin-1-yl)pyrido[2,3-d]pyrimidin-2(1H)-one was re-dissolved in dichloromethane (6.4 mL) followed by dropwise addition of acryloyl chloride (1.74 mL, 1.92 mmol). The reaction was stirred for 30 min at RT, partitioned between EtOAc and NaHCO$_3$, washed with NaHCO$_3$, washed with brine, dried over MgSO$_4$, and purified by silica gel chromatography (eluent: 30-100% EtOAcEtOH (3:1)/heptanes) to provide (4-acryloyl-cis-3,5-dimethylpiperazin-1-yl)-6,7-dichloro-1-(4,6-diisopropylpyrimidin-5-yl)pyrido[2,3-d]pyrimidin-2(1H)-one (0.51 g, 73% yield) as a white solid. $^1$H NMR (400 MHz, DMSO-d$_6$) δ ppm 9.16 (s, 1H), 8.58 (s, 1H), 6.79 (dd, J=10.6, 16.6 Hz, 1H), 6.19 (dd, J=2.4, 16.7 Hz, 1H), 5.74 (dd, J=2.8, 10.1 Hz, 1H), 4.55 (br s, 2H), 4.30 (br d, J=13.3 Hz, 2H), 3.69 (dd, J=4.9, 13.6 Hz, 2H), 2.75-2.68 (m, 2H), 1.35 (d, J=6.8 Hz, 6H), 1.09 (d, J=6.6 Hz, 6H), 1.01 (d, J=6.6 Hz, 6H). m/z (ESI, +ve ion) 544.0 (M+H)$^+$.

Step 2: 4-(4-Acryloyl-cis-3,5-dimethylpiperazin-1-yl)-6-chloro-1-(4,6-diisopropylpyrimidin-5-yl)-7-(2-fluoro-6-hydroxyphenyl)pyrido[2,3-d]pyrimidin-2(1H)-one A vial was charged with 4-(4-acryloyl-cis-3,5-dimethylpiperazin-1-yl)-6,7-dichloro-1-(4,6-diisopropylpyrimidin-5-yl)pyrido[2,3-d]pyrimidin-2(1H)-one (Intermediate T, 0.26 g, 0.47 mmol), potassium trifluoro(2-fluoro-6-hydroxyphenyl)borate (0.12 g, 0.56 mmol, Intermediate L), dichloro[1,1'-bis(diphenylphosphino)ferrocene]palladium (II) dichloromethane adduct (0.03 g, 0.05 mmol), and KOAc (0.23 g, 2.34 mmol). The flask was evacuated and backfilled with N$_2$ followed by addition of 1,4-dioxane (1.8 mL) and water (0.47 mL). The mixture was stirred at 90° C. for 18 h and purified by silica gel chromatography (eluent: 30-60% EtOAc-EtOH (3:1)/heptanes) to provide 4-(4-acryloyl-cis-3,5-dimethylpiperazin-1-yl)-6-chloro-1-(4,6-diisopropylpyrimidin-5-yl)-7-(2-fluoro-6-hydroxyphenyl)pyrido[2,3-d]pyrimidin-2(1H)-one (0.13 g, 44.8% yield) as a yellow solid. $^1$H NMR (400 MHz, DMSO-d$_6$) δ ppm 10.13 (br s, 1H), 9.04 (s, 1H), 8.54 (s, 1H), 7.27-7.19 (m, 1H), 6.81 (dd, J=10.6, 16.6 Hz, 1H), 6.73-6.63 (m, 2H), 6.20 (dd, J=2.4, 16.7 Hz, 1H), 5.78-5.72 (m, 1H), 4.58 (br s, 2H), 4.34 (br d, J=13.7 Hz, 2H), 3.66 (dd, J=4.6, 13.7 Hz, 2H), 2.75-2.68 (m, 2H), 1.42 (br d, J=6.6 Hz, 6H), 1.08 (d, J=6.6 Hz, 6H), 0.97-0.90 (m, 6H). $^{19}$F NMR (376 MHz, DMSO-d$_6$) δ ppm −116.05 (s, 1F). m/z (ESI, +ve ion) 620.0 (M+H)$^+$.

Example 21

4-(4-Acryloyl-cis-3,5-dimethylpiperazin-1-yl)-7-(2-amino-6-fluorophenyl)-6-chloro-1-(4,6-diisopropylpyrimidin-5-yl)pyrido[2,3-d]pyrimidin-2(1H)-one

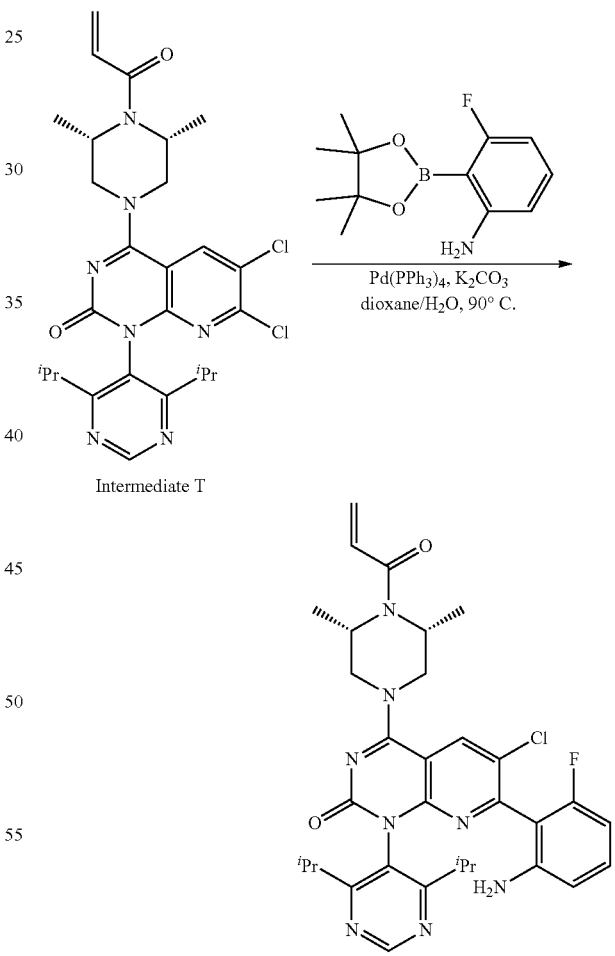

4-(4-Acryloyl-cis-3,5-dimethylpiperazin-1-yl)-7-(2-amino-6-fluorophenyl)-6-chloro-1-(4,6-diisopropylpyrimidin-5-yl)pyrido[2,3-d]pyrimidin-2(1H)-one A vial was charged with 4-(4-acryloyl-cis-3,5-dimethylpiperazin-1-yl)-6,7-dichloro-1-(4,6-diisopropylpyrimidin- 5-yl)pyrido[2,3-d]pyrimidin-2(1H)-one (Intermediate T, 0.26 g, 0.47 mmol), potassium carbonate (0.14 g, 2.31 mmol), (2-amino-6-fluorophenyl)boronic acid pinacol ester (0.12 g, 0.52 mmol, Enamine, San Diego, Calif.), tetrakis (triphenylphosphine)palladium(0) (54 mg, 0.05 mmol), and 1,4-dioxane (1.6 mL). The mixture was degassed with $N_2$, water (0.7 mL) was added, and the mixture was stirred at 90° C. for 2 h, then cooled to rt, adsorbed directly onto $SiO_2$, and purified by silica gel chromatography (eluent: 30%-60% EtOAc-EtOH (3:1)/heptane) to provide 4-(4-acryloyl-cis-3,5-dimethylpiperazin-1-yl)-7-(2-amino-6-fluorophenyl)-6-chloro-1-(4,6-diisopropylpyrimidin-5-yl)pyrido[2,3-d]pyrimidin-2(1H)-one (0.045 g, 0.073 mmol, 15.5% yield) as a yellow solid. $^1$H NMR (400 MHz, DMSO-$d_6$) δ ppm 9.05 (s, 1H), 8.53 (s, 1H), 7.11-6.97 (m, 1H), 6.82 (dd, J=10.5, 16.7 Hz, 1H), 6.44 (d, J=8.4 Hz, 1H), 6.31 (t, J=9.0 Hz, 1H), 6.20 (dd, J=2.4, 16.7 Hz, 1H), 5.78-5.73 (m, 1H), 5.09 (br s, 2H), 4.60 (br s, 2H), 4.32 (br d, J=13.3 Hz, 2H), 3.68 (ddd, J=4.8, 8.8, 13.6 Hz, 2H), 2.92-2.81 (m, 1H), 2.66-2.61 (m, 1H), 1.47-1.35 (m, 6H), 1.12-0.93 (m, 12H). $^{19}$F NMR (376 MHz, DMSO-$d_6$) δ ppm −116.31 (s, 1F). m/z (ESI, +ve ion) 619.6 (M+H)$^+$.

Example 22

4-(4-Acryloyl-cis-3,5-dimethylpiperazin-1-yl)-1-(4,6-diisopropylpyrimidin-5-yl)-6-fluoro-7-(2-fluorophenyl)pyrido[2,3-d]pyrimidin-2(1H)-one

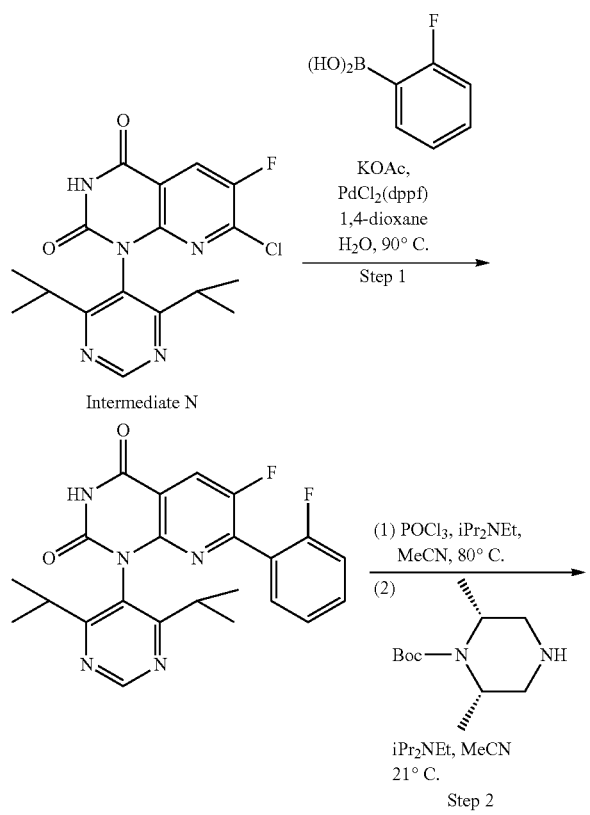

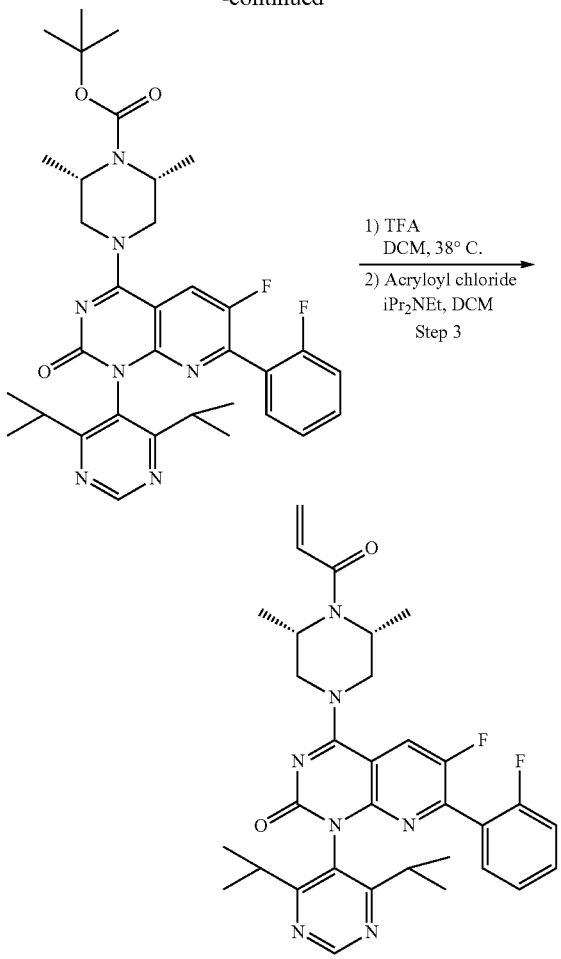

Step 1: 1-(4,6-Diisopropylpyrimidin-5-yl)-6-fluoro-7-(2-fluorophenyl)pyrido[2,3-d]pyrimidine-2,4(1H,3H)-dione To a 100-mL round-bottomed flask was added 7-chloro-1-(4,6-diisopropylpyrimidin-5-yl)-6-fluoropyrido[2,3-d]pyrimidine-2,4(1H,3H)-dione (Intermediate N, 0.420 g, 1.11 mmol) and KOAc (0.327 g, 3.34 mmol) in 1,4-dioxane (5.56 mL). The reaction mixture was degassed by bubbling ($N_2$) gas into the mixture for 5 min. Then (1,1'-bis(diphenylphosphino)ferrocene)dichloropalladium (0.081 g, 0.111 mmol) was added into the reaction mixture. The mixture was stirred and heated at 95° C. for 10 min. 2-Fluorophenylboronic acid (0.187 g, 1.33 mmol) and water (0.1 mL) were added into the reaction mixture. The overall mixture was allowed to stir at 95° C. for 16 h. The reaction mixture was diluted with sat. aq. ammonium chloride and EtOAc. The layers were separated and the aqueous layer was extracted with EtOAc. The combined organic extracts were dried over $MgSO_4$, filtered and concentrated in vacuo. The crude material was adsorbed onto a plug of silica gel and purified by silica gel chromatography (eluent: 0-100% EtOAc/heptane) to afford 1-(4,6-diisopropylpyrimidin-5-yl)-6-fluoro-7-(2-fluorophenyl)pyrido[2,3-d]pyrimidine-2,4(1H,3H)-dione (0.235 g, 0.537 mmol, 48.3% yield) as a light-yellow solid. $^1$H NMR (400 MHz, DMSO-$d_6$) δ ppm 12.27 (br s, 1H) 9.12 (s, 1H) 8.46 (d, J=8.50 Hz, 1H) 7.48-7.57 (m, 1H) 7.20-7.36 (m, 3H)

2.88-3.08 (m, 2H) 1.10 (d, J=6.63 Hz, 6H) 0.94 (d, J=6.63 Hz, 6H). m/z (ESI, +ve ion): 438.1 (M+H)⁺.

Step 2: tert-Butyl 4-(1-(4,6-diisopropylpyrimidin-5-yl)-6-fluoro-7-(2-fluorophenyl)-2-oxo-1,2-dihydro-pyrido[2,3-d]pyrimidin-4-yl)-cis-2,6-dimethylpipera-zine-1-carboxylate To a 100-mL round-bottomed flask was added 1-(4,6-diisopropylpyrimidin-5-yl)-6-fluoro-7-(2-fluorophenyl) pyrido[2,3-d]pyrimidine-2,4(1H,3H)-dione (0.105 g, 0.240 mmol) and DIPEA (0.054 mL, 0.312 mmol) in acetonitrile (1.20 mL). Then phosphorous oxychloride (0.027 mL, 0.288 mmol) was added slowly into the reaction mixture. The flask was fitted with an air-cooled condenser, then the mixture was stirred and heated at 80° C., while under an inert (N₂) atmosphere for 30 min. The reaction mixture was removed from the heating bath and allowed to cool to rt. The reaction mixture was cooled to 0° C. Then DIPEA (0.5 mL) was added slowly into the mixture. Then a mixture of (2R,6S)-tert-butyl 2,6-dimethylpiperazine-1-carboxylate (0.064 mL, 0.300 mmol) in acetonitrile (1 mL) was added slowly into the reaction mixture. The ice bath was removed and the overall mixture was allowed to warm to rt over 10 min. The reaction mixture was concentrated in vacuo. The crude material was adsorbed onto a plug of silica gel and purified by chromatography (eluent: 0-70% EtOAc/heptane) to afford tert-butyl 4-(1-(4,6-diisopropylpyrimidin-5-yl)-6-fluoro-7-(2-fluorophenyl)-2-oxo-1,2-dihydropyrido[2,3-d] pyrimidin-4-yl)-cis-2,6-dimethylpiperazine-1-carboxylate (0.105 g, 0.166 mmol, 69.0% yield) as a light-yellow solid. m/z (ESI, +ve ion): 634.3 (M+H)⁺.

Step 3: 4-(4-Acryloyl-cis-3,5-dimethylpiperazin-1-yl)-1-(4,6-diisopropylpyrimidin-5-yl)-6-fluoro-7-(2-fluorophenyl)pyrido[2,3-d]pyrimidin-2(1H)-one To a 100-mL round-bottomed flask was added tert-butyl 4-(1-(4,6-diisopropylpyrimidin-5-yl)-6-fluoro-7-(2-fluoro-phenyl)-2-oxo-1,2-dihydropyrido[2,3-d]pyrimidin-4-yl)-cis-2,6-dimethylpiperazine-1-carboxylate (0.100 g, 0.158 mmol) and trifluoroacetic acid (0.118 mL, 1.58 mmol) in DCM (1.97 mL). The reaction mixture was stirred and heated at 38° C. while under an inert (N₂) atmosphere for 2.5 h. The reaction mixture was concentrated in vacuo to provide 1-(4,6-diisopropylpyrimidin-5-yl)-4-(cis-3,5-dim-ethylpiperazin-1-yl)-6-fluoro-7-(2-fluorophenyl)pyrido[2,3-d]pyrimidin-2(1H)-one as a crude residue. This material was carried directly into the next step of the synthesis, without further purification.

The residue of 1-(4,6-diisopropylpyrimidin-5-yl)-4-(cis-3,5-dimethylpiperazin-1-yl)-6-fluoro-7-(2-fluorophenyl) pyrido[2,3-d]pyrimidin-2(1H)-one was diluted with dichloromethane (1.97 mL) and the reaction mixture was cooled to 0° C. Then DIPEA (0.331 mL, 1.89 mmol) was added into the reaction mixture and it was allowed to stir for 2 min. Acryloyl chloride (0.013 mL, 0.158 mmol) was added dropwise into the reaction mixture. The reaction mixture was allowed to stir 30 min. The mixture was diluted with DCM and sat. aq. NaHCO₃, then the layers were separated. The aqueous layer was extracted with DCM. The combined organic extracts were dried over MgSO₄, filtered and concentrated in vacuo. The crude material was adsorbed onto a plug of silica gel and purified by silica gel chromatography (eluent: 0-4% MeOH/DCM) to afford 4-(4-acryloyl-cis-3,5-dimethylpiperazin-1-yl)-1-(4,6-diisopropylpyrimidin-5-yl)-6-fluoro-7-(2-fluorophenyl)pyrido[2,3-d]pyrimidin-2(1H)-one (0.080 g, 0.136 mmol, 86% yield) as off-white solid. ¹H NMR (400 MHz, DMSO-d₆) δ ppm 9.10 (s, 1H) 8.43 (d, J=9.74 Hz, 1H) 7.56 (q, J=7.05 Hz, 1H) 7.23-7.38 (m, 3H) 6.81 (dd, J=16.48, 10.47 Hz, 1H) 6.20 (dd, J=16.69, 1.97 Hz, 1H) 5.73-5.79 (m, 1H) 4.57 (br s, 2H) 4.30-4.40 (m, 2H) 3.73 (dd, J=13.58, 4.66 Hz, 2H) 2.54-2.79 (m, 2H) 1.41 (br d, J=6.63 Hz, 6H) 1.10 (d, J=6.63 Hz, 6H) 0.94 (d, J=6.63 Hz, 6H). m/z (ESI, +ve ion): 588.2 (M+H)⁺.

Example 23

4-(4-Acryloyl-cis-3,5-dimethylpiperazin-1-yl)-1-(4,6-diisopropylpyrimidin-5-yl)-6-fluoro-7-(2-fluoro-6-hydroxyphenyl)pyrido[2,3-d]pyrimidin-2(1H)-one

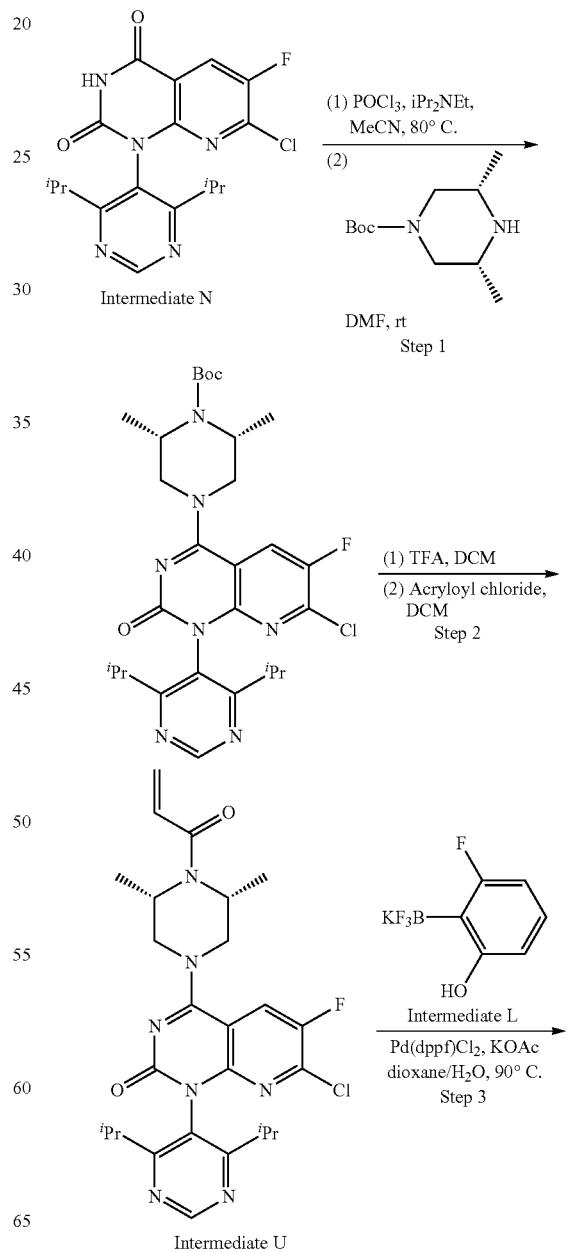

-continued

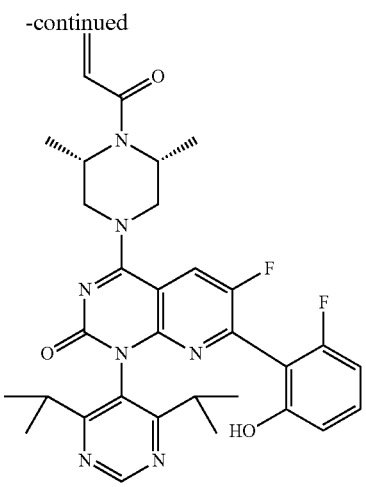

Step 1: tert-Butyl 4-(7-chloro-1-(4,6-diisopropylpyrimidin-5-yl)-6-fluoro-2-oxo-1,2-dihydropyrido[2,3-d]pyrimidin-4-yl)-cis-2,6-dimethylpiperazine-1-carboxylate Phosphorous oxychloride (0.34 mL, 3.63 mmol) was added dropwise to a solution of 7-chloro-1-(4,6-diisopropylpyrimidin-5-yl)-6-fluoropyrido[2,3-d]pyrimidine-2,4(1H,3H)-dione (Intermediate N, 0.5 g, 1.32 mmol) and DPIEA (0.69 mL, 3.93 mmol) in acetonitrile (1.3 mL). The mixture was heated to 80° C. for 1 h, then cooled to 0° C. DIPEA (1.58 mL, 9.07 mmol) and t-butyl cis-2,6-dimethylpiperazine-1-carboxylate (0.30 g, 1.39 mmol, Enamine, San Diego, Calif.) were added. The mixture was warmed to rt, stirred for 1 h then poured into a cold solution of saturated NaHCO$_3$ and stirred vigorously for 10 min. The mixture was partitioned between EtOAc and brine, the layers were separated, the aqueous layer was back-extracted with EtOAc, and the combined organic extracts were dried over MgSO$_4$, filtered, and concentrated in vacuo. The crude material was purified by silica gel chromatography (eluent: 0-40% EtOAc-EtOH (3:1)/heptanes) to provide tert-butyl 4-(7-chloro-1-(4,6-diisopropylpyrimidin-5-yl)-6-fluoro-2-oxo-1,2-dihydropyrido[2,3-d]pyrimidin-4-yl)-cis-2,6-dimethylpiperazine-1-carboxylate (0.59 g, 78% yield) as a white solid that was used without further purification. m/z (ESI, +ve ion) 574.0 (M+H)$^+$.

Step 2: 4-(4-Acryloyl-cis-3,5-dimethylpiperazin-1-yl)-7-chloro-1-(4,6-diisopropylpyrimidin-5-yl)-6-fluoropyrido[2,3-d]pyrimidin-2(1H)-one (Intermediate U)

A vial was loaded with tert-butyl 4-(7-chloro-1-(4,6-diisopropylpyrimidin-5-yl)-6-fluoro-2-oxo-1,2-dihydropyrido[2,3-d]pyrimidin-4-yl)-cis-2,6-dimethylpiperazine-1-carboxylate (0.59 g, 1.03 mmol), DCM (5.2 mL), and trifluoroacetic acid (1.53 mL, 20.5 mmol). The mixture was stirred for 1 h at rt and partitioned between EtOAc and NaHCO$_3$. The organic layer was washed with NaHCO$_3$, washed with brine, dried over MgSO$_4$, and concentrated in vacuo to provide 7-chloro-1-(4,6-diisopropylpyrimidin-5-yl)-4-(cis-3,5-dimethylpiperazin-1-yl)-6-fluoropyrido[2,3-d]pyrimidin-2(1H)-one as a crude residue.

The residue of 7-chloro-1-(4,6-diisopropylpyrimidin-5-yl)-4-(cis-3,5-dimethylpiperazin-1-yl)-6-fluoropyrido[2,3-d]pyrimidin-2(1H)-one was re-dissolved in dichloromethane (5.2 mL) and acryloyl chloride (2.42 mL, 2.66 mmol) was added dropwise. The reaction mixture was stirred for 30 min at rt, and partitioned between EtOAc and NaHCO$_3$. The organic layer was washed with NaHCO$_3$, washed with brine, dried over MgSO$_4$, and purified by silica gel chromatography (eluent: 30-100% EtOAc-EtOH (3:1)/heptanes) to provide 4-(4-acryloyl-cis-3,5-dimethylpiperazin-1-yl)-7-chloro-1-(4,6-diisopropylpyrimidin-5-yl)-6-fluoropyrido[2,3-d]pyrimidin-2(1H)-one (0.44 g, 82% yield) as a white solid. $^1$H NMR (400 MHz, DMSO-d$_6$) δ ppm 9.16 (s, 1H), 8.46 (d, J=8.5 Hz, 1H), 6.79 (dd, J=10.6, 16.6 Hz, 1H), 6.18 (dd, J=2.4, 16.7 Hz, 1H), 5.78-5.72 (m, 1H), 4.54 (br s, 2H), 4.30 (dd, J=2.5, 13.7 Hz, 2H), 3.71 (dd, J=4.8, 13.7 Hz, 2H), 2.73-2.65 (m, 2H), 1.34 (d, J=6.6 Hz, 6H), 1.09 (d, J=6.6 Hz, 6H), 1.00 (d, J=6.6 Hz, 6H). $^{19}$F NMR (376 MHz, DMSO-d$_6$) δ ppm −127.69 (s, 1F). m/z (ESI, +ve ion) 528.0 (M+H)$^+$.

Step 3: 4-(4-Acryloyl-cis-3,5-dimethylpiperazin-1-yl)-1-(4,6-diisopropylpyrimidin-5-yl)-6-fluoro-7-(2-fluoro-6-hydroxyphenyl)pyrido[2,3-d]pyrimidin-2(1H)-one A vial was charged with 4-(4-acryloyl-cis-3,5-dimethylpiperazin-1-yl)-7-chloro-1-(4,6-diisopropylpyrimidin-5-yl)-6-fluoropyrido[2,3-d]pyrimidin-2(1H)-one (Intermediate U, 0.22 g, 0.42 mmol), potassium trifluoro(2-fluoro-6-hydroxyphenyl)borate (0.11 g, 0.51 mmol, Intermediate L), dichloro[1,1'-bis(diphenylphosphino)ferrocene]palladium (II) dichloromethane adduct (0.03 g, 0.04 mmol), and KOAc (0.21 g, 2.10 mmol). The flask was evacuated and backfilled with N$_2$ followed by addition of 1,4-dioxane (1.7 mL) and water (0.4 mL). The mixture was stirred at 90° C. for 2 h, then cooled to rt, and purified by silica gel chromatography (eluent: 30%-60% EtOAc-EtOH (3:1)/heptane) to provide 4-(4-acryloyl-cis-3,5-dimethylpiperazin-1-yl)-1-(4,6-diisopropylpyrimidin-5-yl)-6-fluoro-7-(2-fluoro-6-hydroxyphenyl)pyrido[2,3-d]pyrimidin-2(1H)-one (0.13 g, 49% yield) as a yellow solid. $^1$H NMR (400 MHz, DMSO-d$_6$) δ ppm 10.21 (br s, 1H), 9.05 (s, 1H), 8.36 (d, J=9.3 Hz, 1H), 7.30-7.23 (m, 1H), 6.84-6.65 (m, 3H), 6.19 (dd, J=2.4, 16.7 Hz, 1H), 5.78-5.72 (m, 1H), 4.56 (br s, 2H), 4.33 (dd, J=2.4, 13.6 Hz, 2H), 3.69 (dd, J=4.7, 13.6 Hz, 2H), 2.74-2.64 (m, 2H), 1.41 (d, J=6.8 Hz, 6H), 1.08 (d, J=6.6 Hz, 6H), 0.93 (d, J=6.6 Hz, 6H). $^{19}$F NMR (376 MHz, DMSO-d$_6$) δ ppm −115.89 (s, 1F), −128.23 (s, 1F). m/z (ESI, +ve ion) 604.1 (M+H)$^+$.

Example 24

4-(4-Acryloyl-cis-3,5-dimethylpiperazin-1-yl)-7-(2-amino-6-fluorophenyl)-1-(4,6-diisopropylpyrimidin-5-yl)-6-fluoropyrido[2,3-d]pyrimidin-2(1H)-one

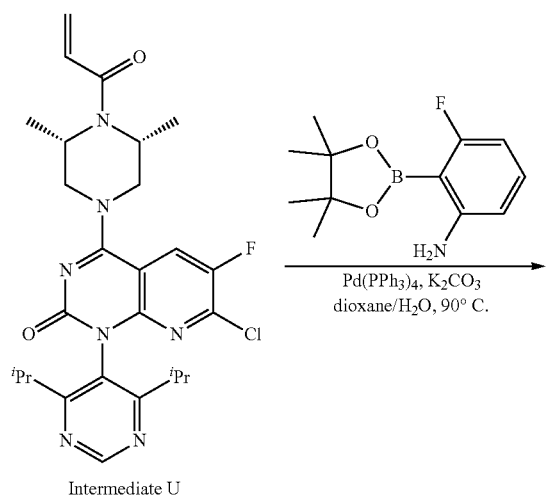

Intermediate U

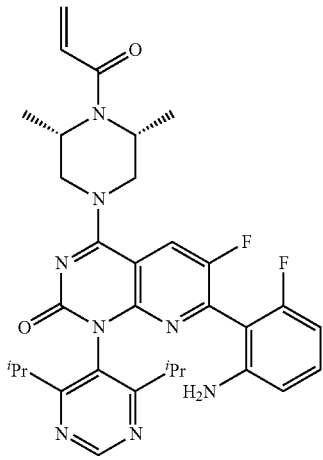

4-(4-Acryloyl-cis-3,5-dimethylpiperazin-1-yl)-7-(2-amino-6-fluorophenyl)-1-(4,6-diisopropylpyrimidin-5-yl)-6-fluoropyrido[2,3-d]pyrimidin-2(1H)-one. A vial was charged with 4-(4-acryloyl-cis-3,5-dimethylpiperazin-1-yl)-7-chloro-1-(4,6-diisopropylpyrimidin-5-yl)-6-fluoropyrido[2,3-d]pyrimidin-2(1H)-one (Intermediate U, 0.22 g, 0.42 mmol), potassium carbonate (0.29 g, 2.10 mmol), (2-amino-6-fluorophenyl)boronic acid pinacol ester (0.11 g, 0.46 mmol, CombiPhos, Trenton, N.J.), tetrakis(triphenylphosphine)palladium(0) (49 mg, 0.042 mmol), water (0.7 mL) and 1,4-dioxane (1.4 mL). The mixture was degassed with nitrogen, stirred at 90° C. for 2 h, then cooled to rt, and purified by silica gel chromatography (eluent: 30%-60% EtOAc-EtOH (3:1)/heptane) to provide 4-(4-acryloyl-cis-3,5-dimethylpiperazin-1-yl)-7-(2-amino-6-fluorophenyl)-1-(4,6-diisopropylpyrimidin-5-yl)-6-fluoropyrido[2,3-d]pyrimidin-2(1H)-one (0.10 g, 40% yield) as a yellow solid. $^1$H NMR (400 MHz, DMSO-$d_6$) δ ppm 9.09 (s, 1H), 8.37 (d, J=9.5 Hz, 1H), 7.13-7.06 (m, 1H), 6.81 (dd, J=10.6, 16.8 Hz, 1H), 6.47 (d, J=8.3 Hz, 1H), 6.36 (t, J=9.1 Hz, 1H), 6.20 (dd, J=2.5, 16.6 Hz, 1H), 5.78-5.73 (m, 1H), 5.29 (s, 2H), 4.58 (m, 2H), 4.34-4.30 (m, 2H), 3.71 (dd, J=4.8, 13.7 Hz, 2H), 2.78-2.68 (m, 2H), 1.41 (d, J=6.6 Hz, 6H), 1.08 (d, J=6.6 Hz, 6H), 0.94 (d, J=6.6 Hz, 6H). $^{19}$F NMR (376 MHz, DMSO-$d_6$) δ ppm −115.21 (d, J=22.5 Hz, 1F), −127.18 (d, J=22.5 Hz, 1F). m/z (ESI, +ve ion) 603.6 (M+H)$^+$.

Table 2: Biochemical and Cellular Activity of Compounds

For compounds in Table 2, the following assay conditions were employed: Coupled Nucleotide Exchange Assay: Purified GDP-bound KRAS protein (aa 1-169), containing both G12C and C118A amino acid substitutions and an N-terminal His-tag, was pre-incubated with a compound dose-response titration for 5 min in assay buffer (25 mM HEPES pH 7.4, 10 mM MgCl2, and 0.01% Triton X-100). Following compound pre-incubation, purified SOS protein (aa 564-1049) and GTP (Roche 10106399001) were added to the assay wells and incubated for an additional 30 min. To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 5 minutes. The assay plates were then read on a PerkinElmer EnVision Multilabel Reader, using AlphaScreen® technology, and data were analyzed using a 4-parameter logistic model to calculate IC$_{50}$ values.

Phospho-ERK1/2 MSD Assay: MIA PaCa-2 (ATCC® CRL-1420™) and A549 (ATCC® CCL-185™) cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, MIA PaCa-2 or A549 cells were seeded in 96-well cell culture plates at a density of 25,000 cells/well and incubated at 37° C., 5% CO2. A compound dose-response titration was diluted in growth media, added to appropriate wells of a cell culture plate, and then incubated at 37° C., 5% CO2 for 2 hours. Following compound treatment, cells were stimulated with 10 ng/mL EGF (Roche 11376454001) for 10 min, washed with ice-cold Dulbecco's phosphate-buffered saline, no Ca$^{2+}$ or Mg$^{2+}$ (ThermoFisher Scientific 14190144), and then lysed in RIPA buffer (50 mM Tris-HCl pH 7.5, 1% Igepal, 0.5% sodium deoxycholate, 150 mM NaCl, and 0.5% sodium dodecyl sulfate) containing protease inhibitors (Roche 4693132001) and phosphatase inhibitors (Roche 4906837001). Phosphorylation of ERK1/2 in compound-treated lysates was assayed using Phospho-ERK1/2 Whole Cell Lysate kits (Meso Scale Discovery K151DWD) according to the manufacturer's protocol. Assay plates were read on a Meso Scale Discovery Sector Imager 6000, and data were analyzed using a 4-parameter logistic model to calculate IC$_{50}$ values.

The "--" in Table 2 below denotes that no assay was conducted.

| Ex. # | Coupled exchange IC$_{50}$ (µM) | p-ERK IC$_{50}$ (MIA PaCa-2, µM) |
|---|---|---|
| 1 | 0.040 | 0.026 |
| 2 | 0.027 | 0.016 |
| 3 | 0.013 | 0.009 |
| 4 | 0.206 | 0.102 |
| 5 | 0.079 | 0.046 |
| 6 | 0.038 | 0.026 |
| 7 | 0.049 | 0.026 |
| 8 | 0.030 | 0.015 |
| 9 | 0.054 | 0.021 |
| 10 | 0.160 | 0.116 |

| Ex. # | Coupled exchange IC$_{50}$ (μM) | p-ERK IC$_{50}$ (MIA PaCa-2, μM) |
|---|---|---|
| 11 | 0.136 | 0.103 |
| 12 | 0.214 | 0.088 |
| 13 | 0.053 | 0.046 |
| 14 | 0.016 | 0.035 |
| 15 | 0.014 | 0.015 |
| 16 | 0.512 | — |
| 17 | 0.117 | 0.105 |
| 18 | 0.069 | 0.075 |
| 19 | 0.042 | 0.061 |
| 20 | 0.034 | 0.022 |
| 21 | 0.092 | 0.036 |
| 22 | 0.560 | — |
| 23 | 0.173 | 0.132 |
| 24 | 0.396 | — |

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. A method of treating cancer having a KRAS G12C mutation in a subject in need thereof, the method comprising administering to the subject a therapeutically effective amount of a compound having a structure of formula (I)

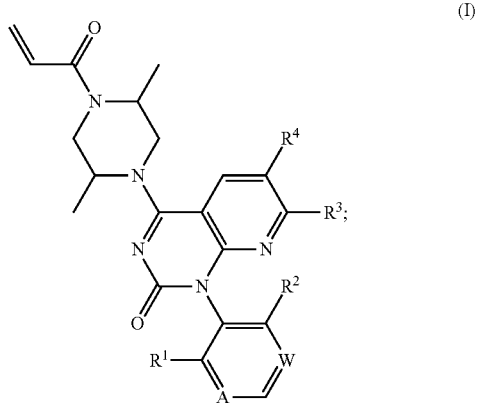

(I)

wherein
A is independently N or CH;
W is independently N or CH;
wherein one or both of A and W is N;
$R^1$ and $R^2$ are independently a branched or a linear $C_{1-6}$alkyl;
$R^3$ is phenyl substituted by 1 or 2 $R^5$ substituents;
$R^5$ is independently selected from one or more halo, —OH, or $NH_2$;
$R^4$ is halo; or
a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, wherein the cancer having a KRAS G12C mutation is non-small cell lung cancer, pancreatic cancer, colorectal cancer, appendix cancer, endometrial cancer, esophageal cancer, gastric cancer, small intestine cancer, nasal cavity cancer, paranasal sinus cancer, bile duct cancer, skin cancer, or intraocular melanoma.

2. The method of claim 1, wherein the compound is a compound having a structure of formula (Ia)

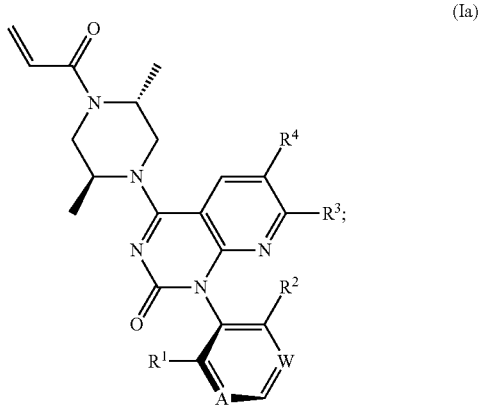

(Ia)

or
a pharmaceutically acceptable salt thereof.

3. The method of claim 1, wherein A is N.
4. The method of claim 1, wherein A is CH.
5. The method of claim 1, wherein W is N.
6. The method of claim 1, wherein W is CH.
7. The method of claim 1, wherein $R^1$ is $CH_3$.
8. The method of claim 1, wherein $R^1$ is $CH(CH_3)_2$.
9. The method of claim 1, wherein $R^2$ is $CH_3$.
10. The method of claim 1, wherein $R^2$ is $CH(CH_3)_2$.
11. The method of claim 1, wherein $R^5$ is halo.
12. The method of claim 11, wherein $R^5$ is F.
13. The method of claim 1, wherein $R^5$ is —OH.
14. The method of claim 1, wherein $R^5$ is —$NH_2$.
15. The method of claim 1, wherein $R^3$ is

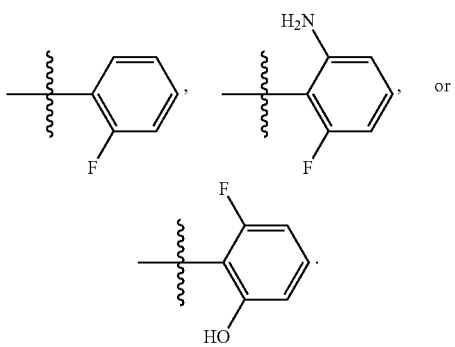

16. The method of claim 15, wherein $R^3$ is

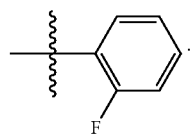 [SMILES: *c1ccccc1F]

17. The method of claim 15, wherein $R^3$ is

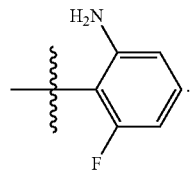 [SMILES: *c1c(N)cccc1F]

18. The method of claim 15, wherein $R^3$ is

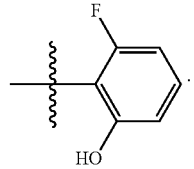 [SMILES: *c1c(O)cccc1F]

19. The method of claim 1, wherein $R^4$ is halo.
20. The method of claim 19, wherein $R^4$ is Cl.
21. The method of claim 19, wherein $R^4$ is F.
22. A method of treating cancer having a KRAS G12C mutation in a subject in need thereof, the method comprising administering to the subject a therapeutically effective amount of a compound having a structure of formula (II)

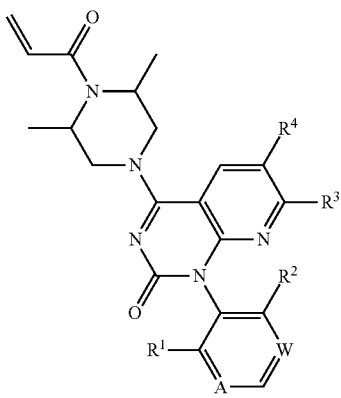

(II)

wherein
A is independently N or CH;
W is independently N or CH;
wherein one or both A and W is N;
R$^1$ and R$^2$ are independently a branched or a linear C$_{1-6}$alkyl;
R$^3$ is phenyl substituted by one or two R$^5$ substituents;
R$^5$ is independently selected from one or more halo, —OH, or NH$_2$; and
R$^4$ is halo; or
a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, wherein the cancer having a KRAS G12C mutation is non-small cell lung cancer, pancreatic cancer, colorectal cancer, appendix cancer, endometrial cancer, esophageal cancer, gastric cancer, small intestine cancer, nasal cavity cancer, paranasal sinus cancer, bile duct cancer, skin cancer, or intraocular melanoma.

23. The method of claim 22, wherein the compound is a compound having a structure of formula (IIa)

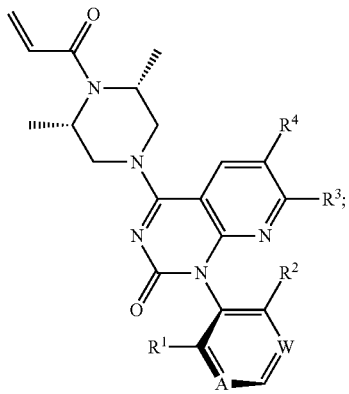

(IIa)

or
a pharmaceutically acceptable salt thereof.
24. The method of claim 22, wherein A is N.
25. The method of claim 22, wherein A is CH.
26. The method of claim 22, wherein W is N.
27. The method of claim 22, wherein W is CH.
28. The method of claim 22, wherein R$^1$ is CH$_3$.
29. The method of claim 22, wherein R$^1$ is CH(CH$_3$)$_2$.
30. The method of claim 22, wherein R$^2$ is CH$_3$.
31. The method of claim 22, wherein R$^2$ is CH(CH$_3$)$_2$.
32. The method of claim 22, wherein R$^5$ is halo.
33. The method of claim 32, wherein R$^5$ is F.
34. The method of claim 22, wherein R$^5$ is —OH.
35. The method of claim 22, wherein R$^5$ is —NH$_2$.
36. The method of claim 22, wherein R$^3$ is

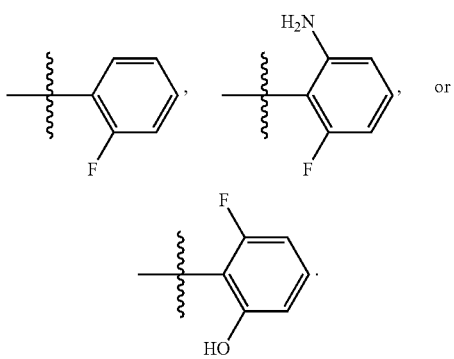

37. The method of claim 36, wherein R$^3$ is

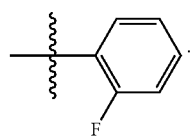 [SMILES: *c1ccccc1F]

38. The method of claim 36, wherein R$^3$ is

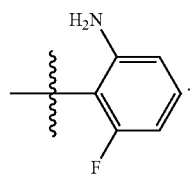 [SMILES: *c1c(N)cccc1F]

39. The method of claim 36, wherein R$^3$ is

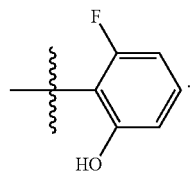 [SMILES: *c1c(O)cccc1F]

40. The method of claim 22, wherein R$^4$ is halo.
41. The method of claim 40, wherein R$^4$ is Cl.
42. The method of claim 40, wherein R$^4$ is F.
43. A method of treating cancer having a KRAS G12C mutation in a subject in need thereof, the method comprising administering to the subject a therapeutically effective amount of a compound having a structure selected from:

151
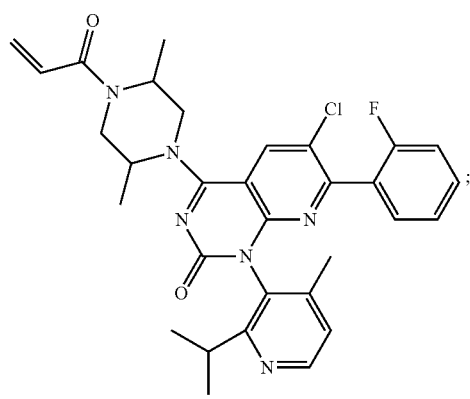
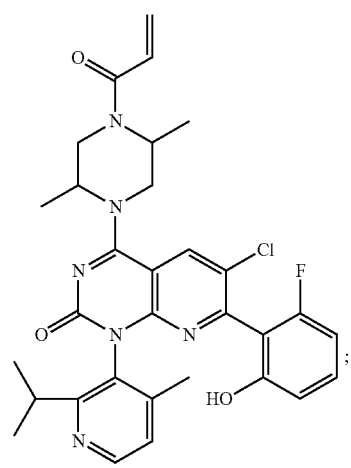
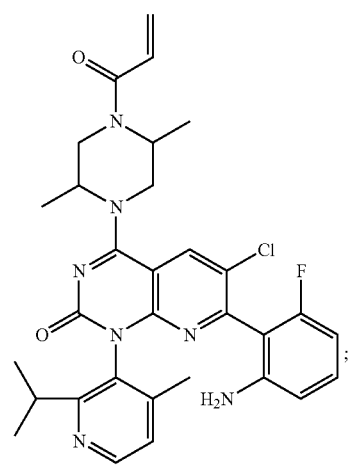
152
-continued
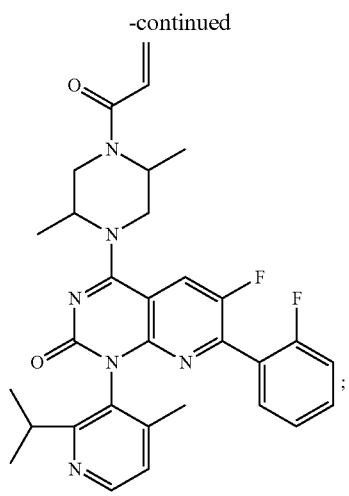
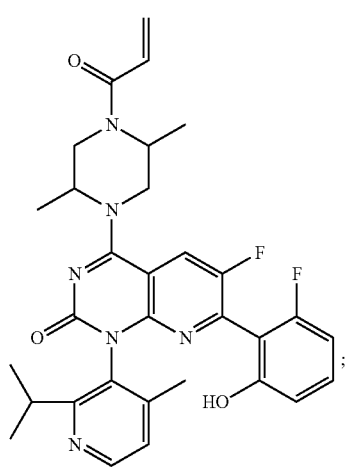
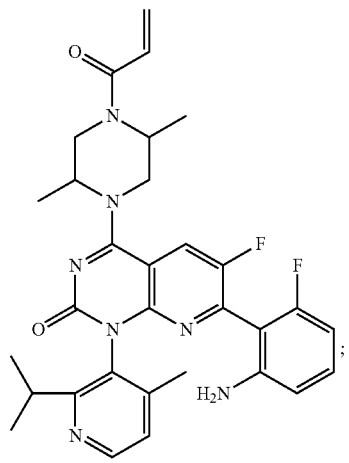

153
-continued
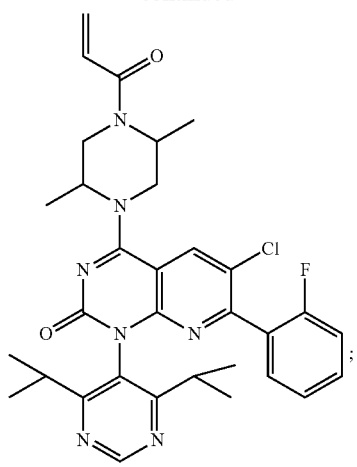
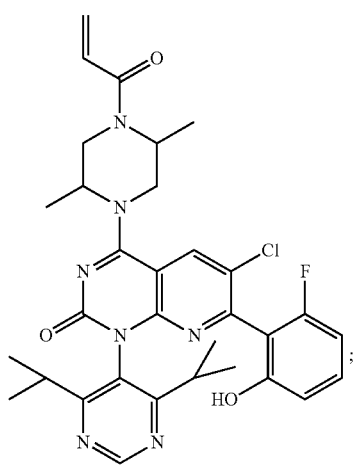
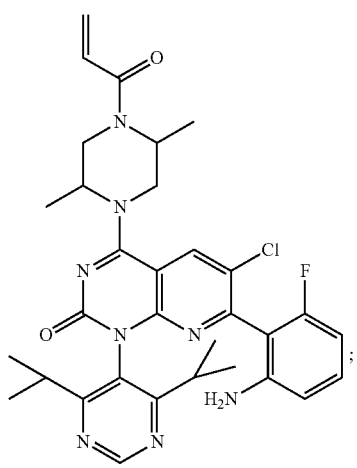
154
-continued
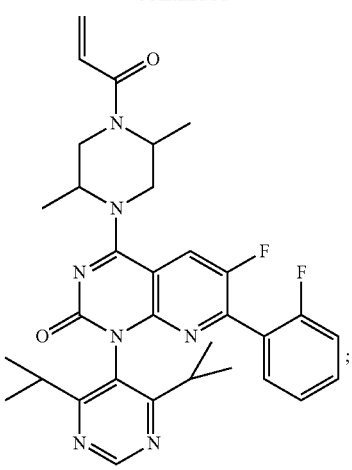
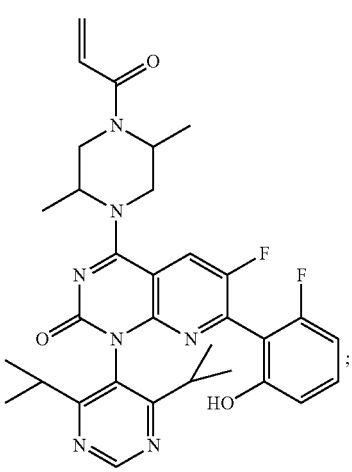
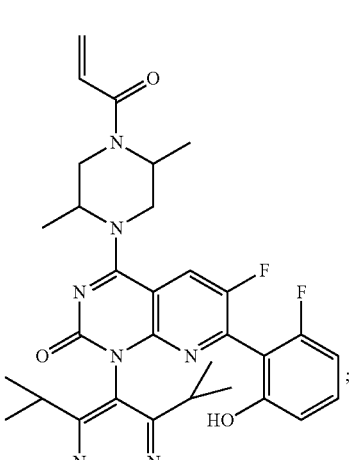

155
-continued
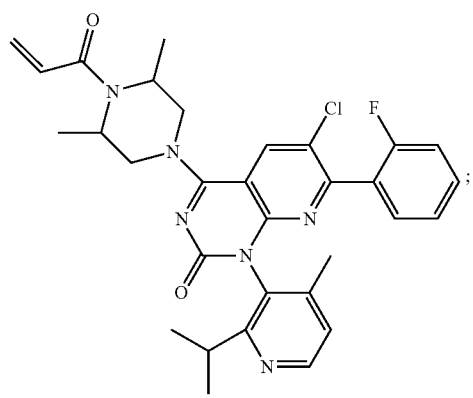
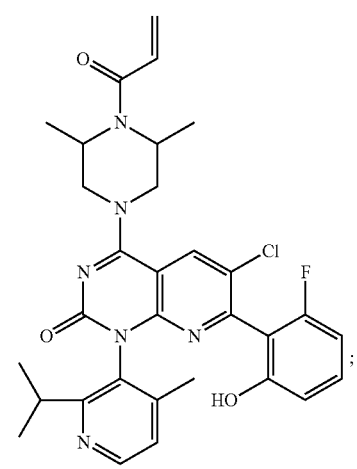
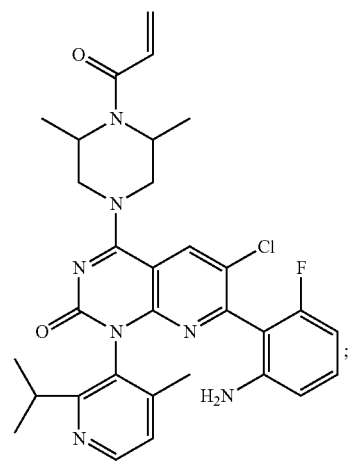
156
-continued
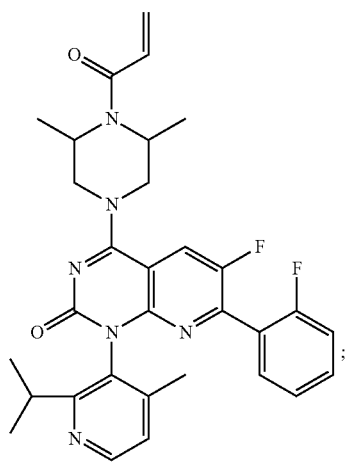
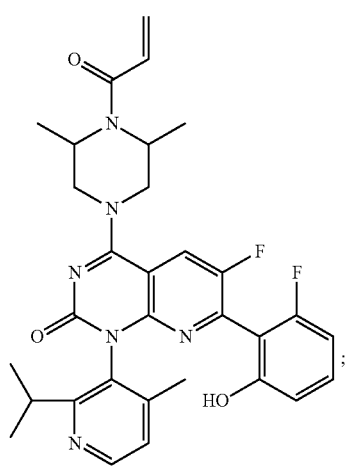
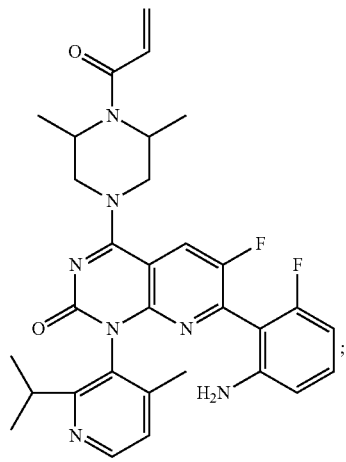

157
-continued

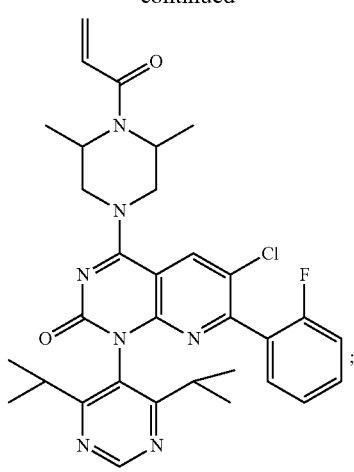

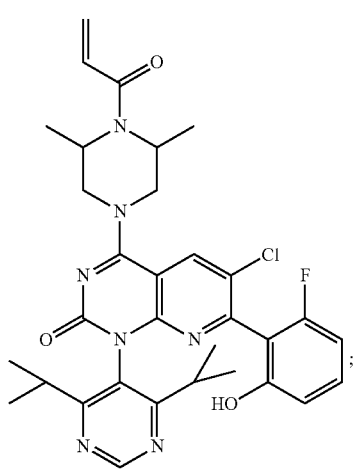

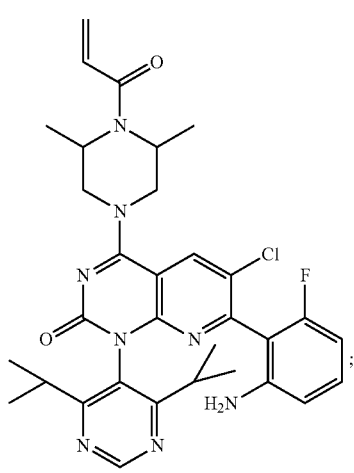

158
-continued

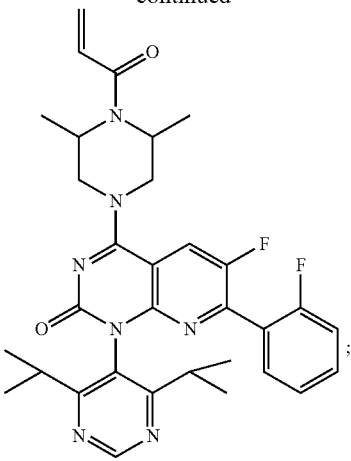

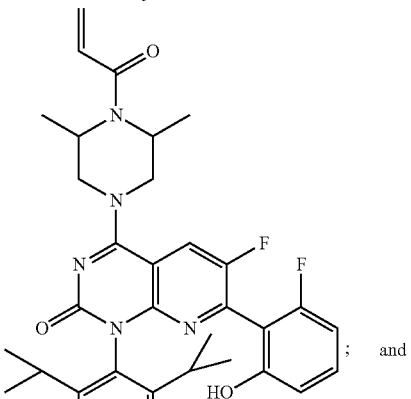

; and

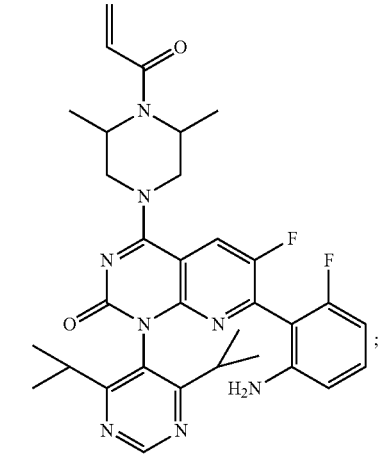

;

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof, wherein the cancer having a KRAS G12C mutation is non-small cell lung cancer, pancreatic cancer, colorectal cancer, appendix cancer, endometrial cancer, esophageal cancer, gastric cancer, small intestine cancer, nasal cavity cancer, paranasal sinus cancer, bile duct cancer, skin cancer, or intraocular melanoma.

44. A method of treating cancer having a KRAS G12C mutation in a subject in need thereof, the method comprising administering to the subject a therapeutically effective amount of a compound having a structure selected from:
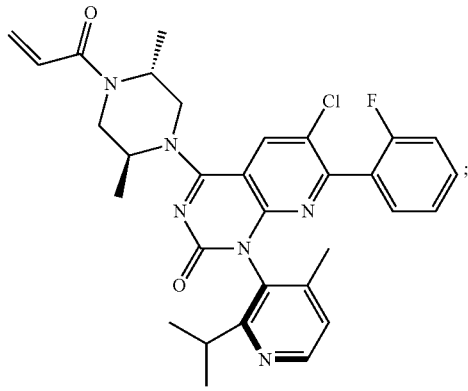
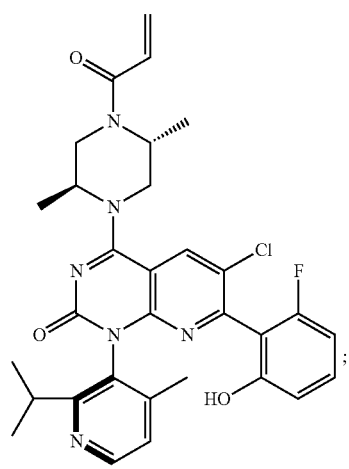
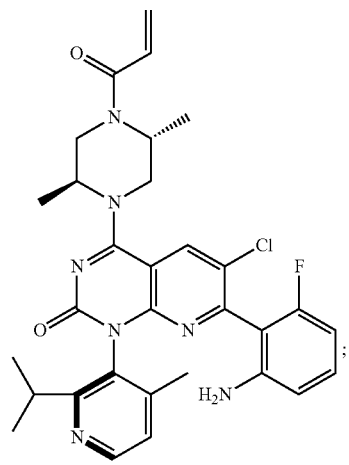
-continued
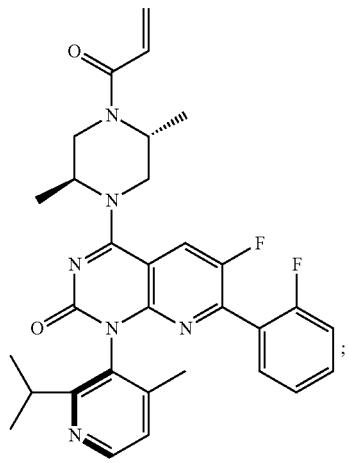
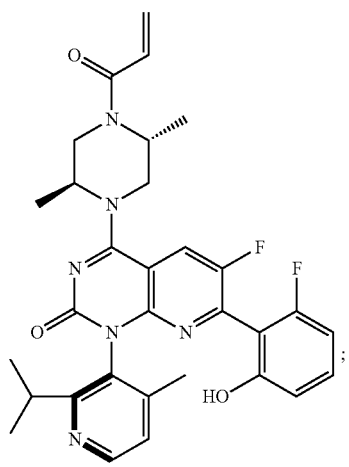
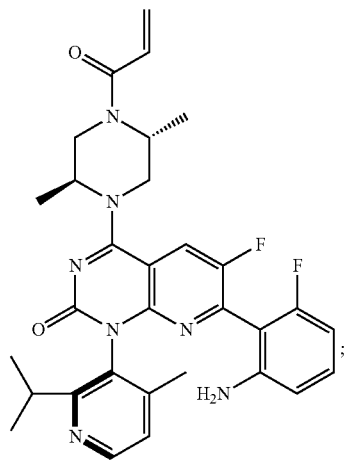

161
-continued
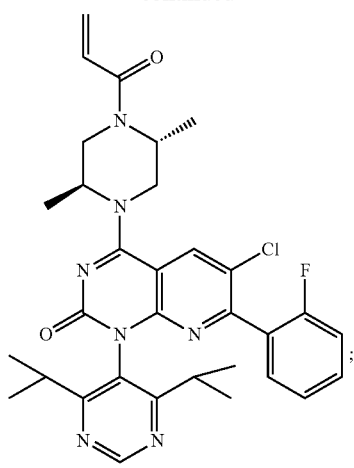
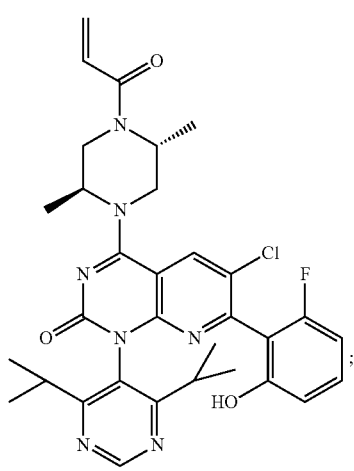
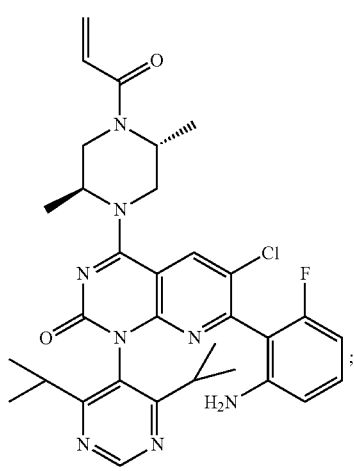
162
-continued
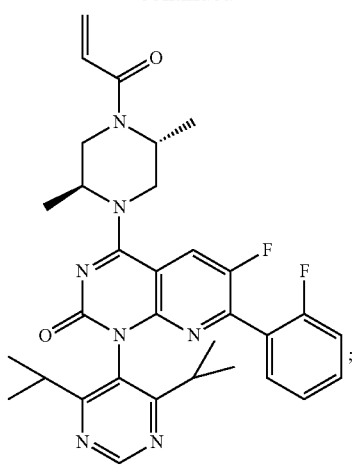
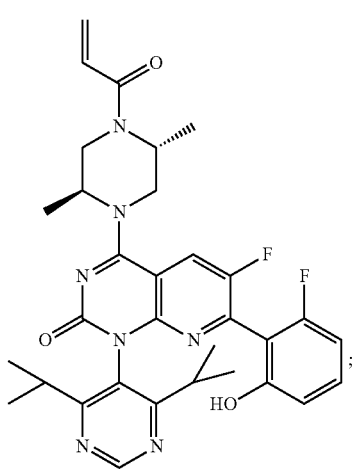
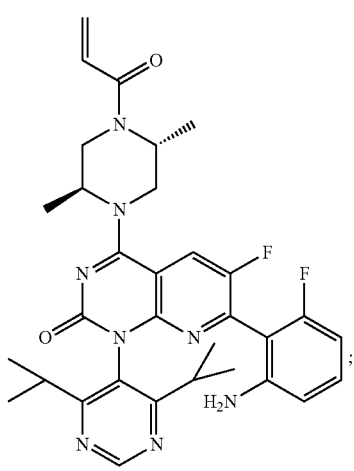

163
-continued
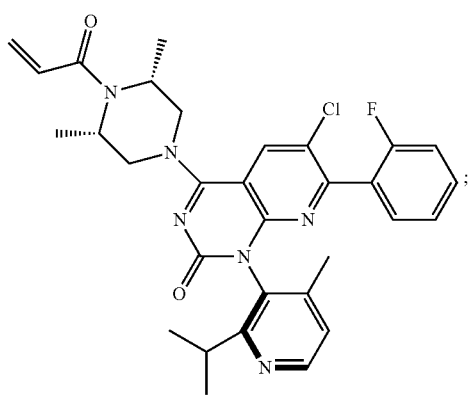
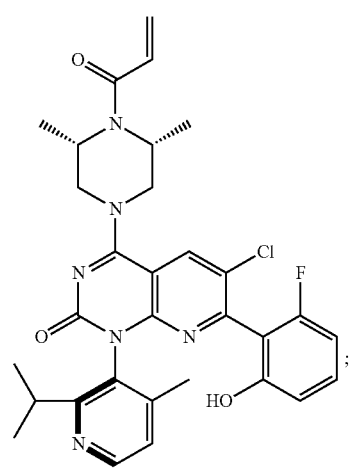
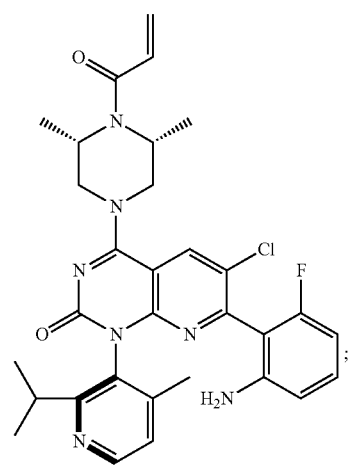
164
-continued
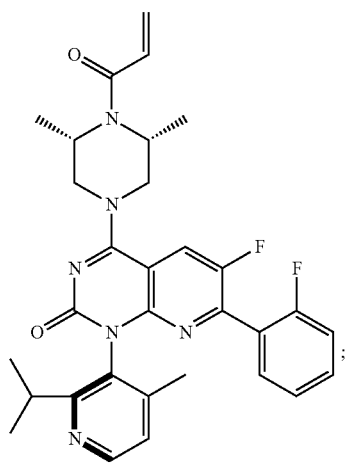
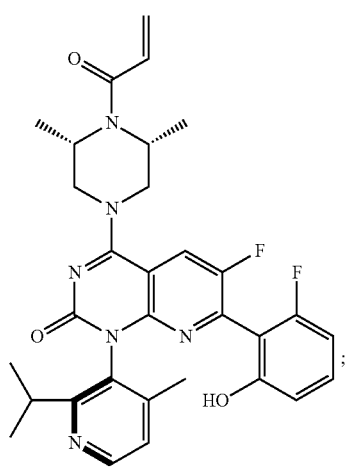
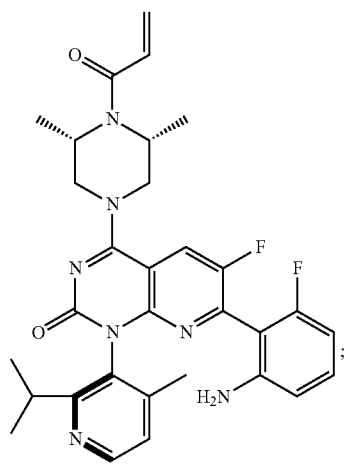

-continued

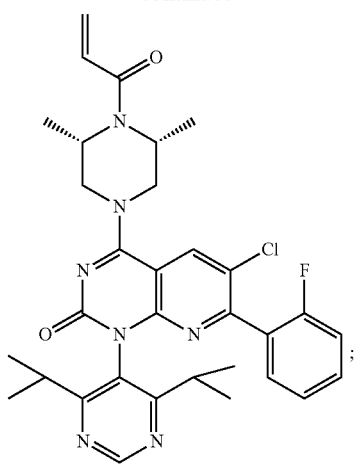

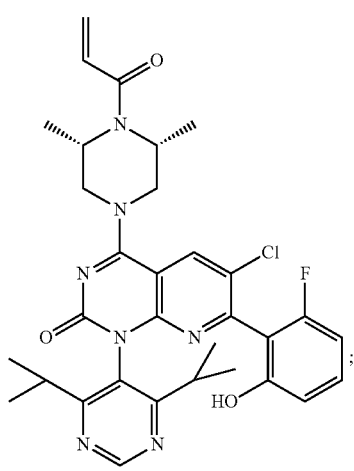

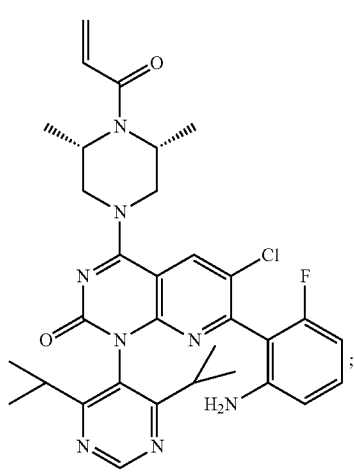

-continued

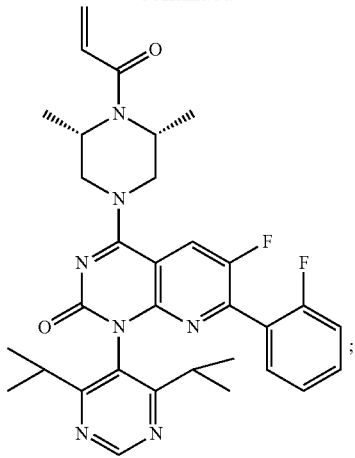

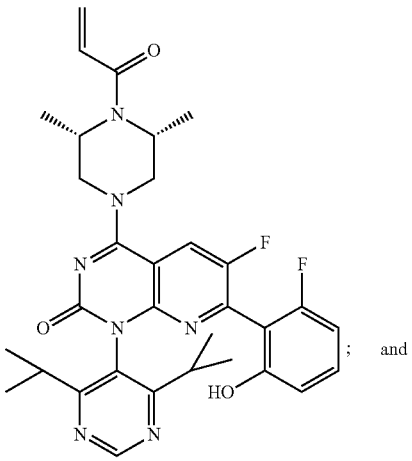; and

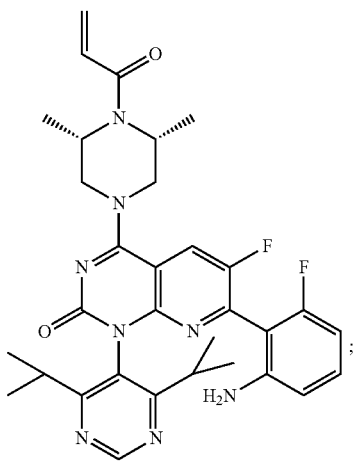;

or a pharmaceutically acceptable salt thereof, wherein the cancer having a KRAS G12C mutation is non-small cell lung cancer, pancreatic cancer, colorectal cancer, appendix cancer, endometrial cancer, esophageal cancer, gastric cancer, small intestine cancer, nasal cavity cancer, paranasal sinus cancer, bile duct cancer, skin cancer, or intraocular melanoma.

45. The method of claim 44, wherein the compound is a compound having a structure

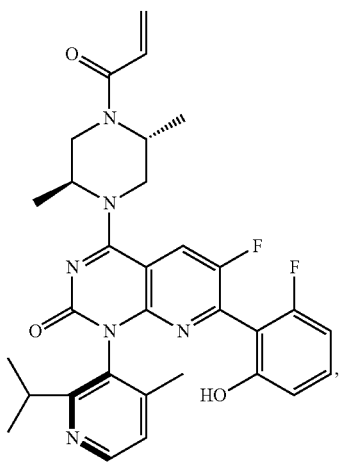

or the pharmaceutically acceptable salt thereof.

46. The method of claim 1, wherein the cancer having a KRAS G12C mutation is non-small cell lung cancer.

47. The method of claim 1, wherein the cancer having a KRAS G12C mutation is colorectal cancer.

48. The method of claim 22, wherein the cancer having a KRAS G12C mutation is non-small cell lung cancer.

49. The method of claim 22, wherein the cancer having a KRAS G12C mutation is colorectal cancer.

50. The method of claim 43, wherein the cancer having a KRAS G12C mutation is non-small cell lung cancer.

51. The method of claim 43, wherein the cancer having a KRAS G12C mutation is colorectal cancer.

52. The method of claim 44, wherein the cancer having a KRAS G12C mutation is non-small cell lung cancer.

53. The method of claim 44, wherein the cancer having a KRAS G12C mutation is colorectal cancer.

54. The method of claim 45, wherein the cancer having a KRAS G12C mutation is non-small cell lung cancer.

55. The method of claim 45, wherein the cancer having a KRAS G12C mutation is colorectal cancer.

* * * * *